(12) United States Patent
Brisander et al.

(10) Patent No.: US 9,827,230 B2
(45) Date of Patent: Nov. 28, 2017

(54) PHARMACEUTICAL COMPOSITIONS

(71) Applicant: XSPRAY MICROPARTICLES AB, Solna (SE)

(72) Inventors: Magnus Brisander, Ekerö (SE); Mustafa Demirbüker, Järfälla (SE); Gérald Jesson, Knivsta (SE); Martin Malmsten, Höllviken (SE); Helene Dérand, Höllviken (SE)

(73) Assignee: XSPRAY MICROPARTICLES AB, Solna (SE)

( * ) Notice: Subject to any disclaimer, the term of this patent is extended or adjusted under 35 U.S.C. 154(b) by 0 days.

(21) Appl. No.: 15/248,107

(22) Filed: Aug. 26, 2016

(65) Prior Publication Data

US 2016/0361313 A1   Dec. 15, 2016

Related U.S. Application Data

(63) Continuation of application No. 14/371,875, filed as application No. PCT/SE2013/050016 on Jan. 11, 2013, now Pat. No. 9,456,992.

(60) Provisional application No. 61/713,120, filed on Oct. 12, 2012, provisional application No. 61/586,187, filed on Jan. 13, 2012.

(30) Foreign Application Priority Data

| Jan. 13, 2012 | (SE) | 1250015 |
| Oct. 12, 2012 | (SE) | 1251160 |

(51) Int. Cl.

| A61K 9/14 | (2006.01) |
| A61K 9/48 | (2006.01) |
| A61K 38/00 | (2006.01) |
| A61K 31/497 | (2006.01) |
| A61K 31/505 | (2006.01) |
| B01F 3/00 | (2006.01) |
| A61K 31/44 | (2006.01) |
| A61K 31/506 | (2006.01) |
| A61K 31/517 | (2006.01) |
| A61K 9/51 | (2006.01) |
| A61K 31/437 | (2006.01) |
| A61K 31/4439 | (2006.01) |
| A61K 31/4545 | (2006.01) |
| A61K 31/5377 | (2006.01) |
| A61K 47/32 | (2006.01) |
| A61K 47/38 | (2006.01) |
| A61K 31/444 | (2006.01) |
| A61K 9/16 | (2006.01) |
| A61K 9/00 | (2006.01) |

(52) U.S. Cl.
CPC ........... *A61K 31/44* (2013.01); *A61K 9/0053* (2013.01); *A61K 9/14* (2013.01); *A61K 9/1641* (2013.01); *A61K 9/1652* (2013.01); *A61K 9/5138* (2013.01); *A61K 9/5146* (2013.01); *A61K 9/5161* (2013.01); *A61K 9/5192* (2013.01); *A61K 31/437* (2013.01); *A61K 31/444* (2013.01); *A61K 31/4439* (2013.01); *A61K 31/4545* (2013.01); *A61K 31/506* (2013.01); *A61K 31/517* (2013.01); *A61K 31/5377* (2013.01); *A61K 47/32* (2013.01); *A61K 47/38* (2013.01)

(58) Field of Classification Search
None
See application file for complete search history.

(56) References Cited

U.S. PATENT DOCUMENTS

| 9,456,992 B2 * | 10/2016 | Brisander ........... A61K 31/437 |
| 2006/0154941 A1 | 7/2006 | Huang |
| 2009/0203709 A1 | 8/2009 | Steinberg et al. |
| 2010/0143459 A1 | 6/2010 | Liepold et al. |

FOREIGN PATENT DOCUMENTS

| EP | 2105130 A1 | 9/2009 |
| WO | 2007133750 A2 | 11/2007 |
| WO | 2007146943 A2 | 12/2007 |
| WO | 2008008733 A2 | 1/2008 |
| WO | 2008055966 A1 | 5/2008 |
| WO | 2005061090 A1 | 6/2009 |
| WO | 2009072950 A1 | 6/2009 |
| WO | 2009072953 A1 | 6/2009 |
| WO | 2011159218 A1 | 12/2011 |

OTHER PUBLICATIONS

Varma et al.; Eur. J. Pharm. Sci 25 (2005), pp. 445-453; available online May 10, 2005.*
Written Opinion for PCT/SE2013/050015, ISA/SE, dated Jul. 15, 2014.
Lowery A. et al, Front Biosci. Jun. 1, 2011; 17:1996-2007.
Herve J. et al., Parm. Dev. Technol. Jun. 2011; 16 (3): 278-86.
Budha NR et al., Clin Pharmacon Ther. Aug. 2012; 92 (2): 203-13.
Saleki-Gerhardt A. et al. Int J. Pharm. 1994; 101: 237-247.
Dash AK et al. J. Pharm Sci. Apr. 2002; 91 (4) 983-990.
Wu K. et al. J. Pharm Sci. Jul. 2009: 98 (7) 2422-3.
Jantraid, E and Dressman, J. Dissolut. Technol. Apr. 2009; 21-25.
Persson, E. M. et al. Pharm Res. 2005, 22, 2041-2151.
Min-Soo Kim et al., Int. Journal Nanomedicine, 2011 :6, 2997-3009.
International Search Report for PCT/SE2013/050016, ISNSE, dated May 6, 2013.

(Continued)

*Primary Examiner* — Jeffrey T. Palenik
(74) *Attorney, Agent, or Firm* — Daniel R. Evans

(57) ABSTRACT

The present invention relates to the field of methods for providing pharmaceutical compositions comprising poorly water-soluble drugs. In particular the present invention relates to compositions comprising stable, amorphous hybrid nanoparticles, comprising at least one protein kinase inhibitor and at least one polymeric stabilizing and matrix-forming component, useful in pharmaceutical compositions and in therapy.

23 Claims, 14 Drawing Sheets

(56) References Cited

OTHER PUBLICATIONS

Extended European Search Report issued in Application No. 17155688.9-1468 dated May 15, 2017, 11 pages.
Extended European Search Report issued in Application No. 17155689.7-1468 dated May 15, 2017, 9 pages.
Extended European Search Report issued in Application No. 17155686.3-1468 dated May 15, 2017, 9 pages.
Arasali Sulaiman Zarena et al. "Design of submicron and nanoparticle delivery systems using supercritical carbon dioxide-mediated procesesses: an overview", Therapeutic Delivery, 2011:2(1) 259-277, 19 pages.
Fine Chemicals (2010) 39(7): 13-18.

* cited by examiner

Apparent solubility of different pazopanib powders in FaSSIF (pH

Apparent solubility of different lapatinib powders in FaSSIF (pH 6.5)

PHARMACEUTICAL COMPOSITIONS

This application is a continuation of U.S. patent application Ser. No. 14/371,875, filed on Jul. 11, 2014, now U.S. Pat. No. 9,456,992, which is a U.S. National Stage Application of PCT/SE2013/050016, filed on Jan. 11, 2013. Priority is claimed to Swedish Patent Application Nos. 1250015-3, filed on Jan. 13, 2012 and 1251160-6, filed on Oct. 12, 2012. Priority is also claimed to U.S. Provisional Patent Application Nos. 61/586,187, filed on Jan. 13, 2012 and 61/713,120, filed on Oct. 12, 2012. The subject matter disclosed in each of the above-mentioned applications is incorporated herein by reference.

FIELD OF THE INVENTION

The present invention relates to the field of pharmaceutical compositions comprising poorly water-soluble drugs. In particular the present invention relates to pharmaceutical compositions comprising stable, amorphous hybrid nanoparticles of protein kinase inhibitors (PKIs) and polymeric stabilizing and matrix-forming components. Furthermore, the present invention relates to a method of treating proliferative disorders in a patient in need thereof, comprising administering a therapeutically effective amount of said compositions.

BACKGROUND OF THE AND INVENTION

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties.

Many proliferative disorders, such as tumors and cancers, have been shown to involve overexpresion or upregulation of protein kinase activity. Protein kinases are kinase enzymes that modify proteins by chemically adding phosphate groups (phosphorylation). Phosphorylation usually results in a functional change of the target protein by changing enzyme activity, cellular location, or association with other proteins. Protein kinases can be subdivided or characterised by the amino acids of the target protein whose phosphorylation they control: most kinases act on both serine and threonine, the tyrosine kinases act on tyrosine, and a number (dual-specificity kinases) act on all three. There are also protein kinases that phosphorylate other amino acids, including histidine kinases that phosphorylate histidine residues. The human genome contains about 500 protein kinase genes and up to 30% of all human proteins may be modified by protein kinases. Kinases are known to regulate the majority of cellular pathways, especially those involved in signal transduction. Dysregulation of protein kinases by mutation, gene rearrangement, gene amplification, and overexpression of both receptor and ligand has been implicated in the development and progression of human cancers. Protein kinase inhibiting compounds or protein kinase inhibitors (PKIs) are therefore useful for treating diseases caused by or exacerbated by overexpression or upregulation of protein kinases. For example, tyrosine kinase inhibitors (TKIs also known as tyrphostins) have been shown be effective anti-tumor agents and anti-leukemic agents (Lowery A et. al., Front Biosci. 2011 Jun. 1; 17:1996-2007).

A major objective of formulation chemistry is to improve drug efficiency and safety, by e.g. improving bioavailability and stability as well as convenience to the patient. Bioavailability means the rate and extent to which an active substance or therapeutic is absorbed from a pharmaceutical form and becomes available at the site of action. The most common and preferred method of delivery due to convenience, ease of ingestion, and high patient compliance to treatment is the oral route of drug delivery. However, for certain drugs, drug absorption from the gastrointestinal tract is limited by poor aqueous solubility and/or poor membrane permeability of the drug molecules.

PKIs are generally weak bases that dissolve only slightly at low pH (e.g. 100-1000 mg/L) and are practically insoluble at neutral pH (e.g. 0.1-10 mg/L). Therefore, enhancing the solubility and dissolution rate of PKI-based drugs is important for improving the bioavailability and efficacy of most of these drugs. Typical PKIs exhibit non-polypetide structure and have relatively low molecular weights, such as ≤10000 dalton or ≤5000 dalton.

Several methods to improve the dissolution characteristics of poorly water soluble drugs have been reported, including micronisation, formation of salts or solvates, complexes and microspheres. Additionally, attempts have been made to improve bioavailability provided by solid dosage forms by forming particles comprising the drug or by mixing the poorly water soluble drug with hydrophilic excipients. Traditionally, however, these methods carry inherent limitations concerning physical stabilities of the particles on storage, problems with grinding or difficulty of removal of the frequently toxic solvent. Furthermore, it is important that the drug released from the solid phase does not precititpitate in the gastrointestinal tract, or precipitates as little as possible, but remains water-soluble in the aqueous fluids of the gastrointestinal tract, since such precipitation results in low bioavailability (see e.g. Hervé J. et al. Pharm Dev Technol. 2011 Jun.; 16(3):278-86).

pH-dependent solubility is a well-known issue for many oral formulations of poorly water-soluble substances, such as PKIs, since most of the absorption of the drug occurs in the small and large intestine, where pH is close to neutral. There is thus a continuing need to develop and improve the dissolution characteristics of oral solid dosage forms of PKI-based drugs. (Budha N R, Frymoyer A, Smelick G S, Jin J Y, Yago M R, Dresser M J, Holden S N, Benet L Z, Ware J A. Clin Pharmacol Ther. 2012 August; 92(2):203-13). Therefore, methods for improving dissolution of PKI-based drugs, as well as of other poorly water-soluble drugs, at neutral (intestinal) pH are highly desirable.

US20090203709 discloses a pharmaceutical dosage form comprising a solid dispersion product of at least one tyrosine kinase inhibitor, at least one pharmaceutically acceptable polymer and at least one pharmaceutically acceptable solubilizer. Further the reference discloses methods for preparing the above-mentioned pharmaceutical dosage form, comprising preparing the homogenous melt of at least one tyrosine kinase inhibitor, at least one pharmaceutically acceptable polymer and at least one pharmaceutically acceptable solubilizer, and allowing the melt to solidify to obtain a solid dispersion product.

EP2105130 discloses pharmaceutical formulations comprising a solid dispersion or solid solution, containing a polymer and an active agent in amorphous form. Further, the formulation comprises an external polymer to stabilize the solution, such that the % by weight of the external polymer is less than 20% of the total weight of the pharmaceutical formulation. Additionally, the reference discloses a hot melt extrusion method for production of the above-mentioned formulation.

SUMMARY OF THE INVENTION

The present invention relates pharmaceutical compositions comprising stable, amorphous hybrid nanoparticles, comprising at least one protein kinase inhibitor and at least one polymeric stabilizing and matrix-forming component. Optionally, one or more solubilizers may be added to the particles, present separately from the particles, or within the particles.

Experiment 137 represents stable, amorphous hybrid nanoparticles of gefitinib and HPMCP HP55 wherein the solubilizer polyvinyl caprolactam-polyvinyl acetate-polyethylene glycol copolymer is present separately from the stable, amorphous hybrid nanoparticles. The experiments illustrated in the graphs were carried out at pH 6.5 in FaSSIF.

Figure 1:
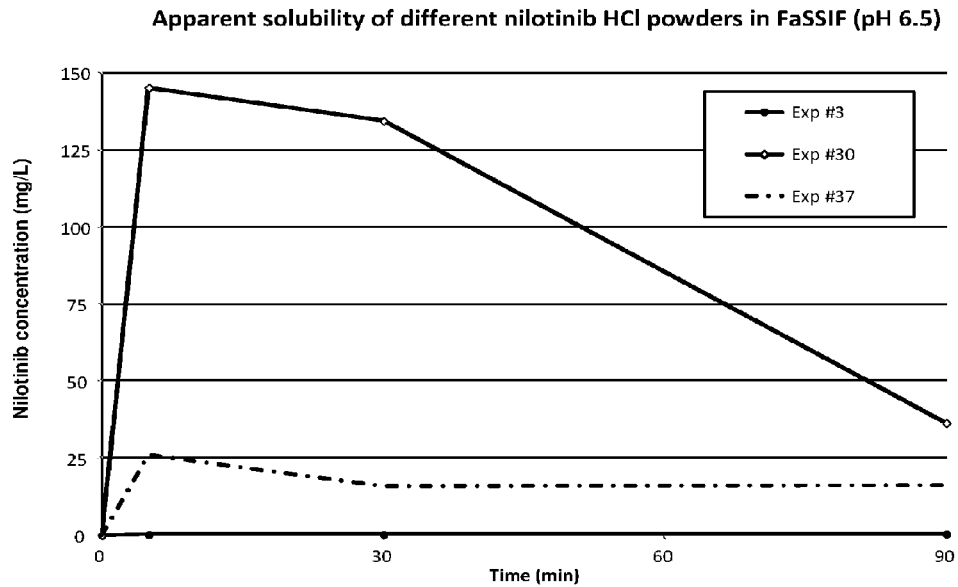
FIG. 1 provides a graph showing the apparent solubility for nilotinib in representative compositions of the invention. Further experimentation with both nilotinib base and nilotinib HCl is found in Example 1. The details of the particles are described in Example 1, Table 1, for experiment 3, 30 and 37, respectively. Briefly, experiment 30 represents stable, amorphous hybrid nanoparticles comprising nilotinib HCl and HPMCP HP55 and wherein the solubilizer polyvinyl caprolactam-polyvinyl acetate-polyethylene glycol copolymer is present separately from the hybrid nanoparticles. Experiment 3 represents raw, crystalline nilotinib HCl and experiment 37 represents hybrid nanoparticles of nilotinib HCl, HPMCP HP55 and the solubilizer polyvinyl caprolactam-polyvinyl acetate-polyethylene glycol copolymer, present within the hybrid nanoparticles. The experiments illustrated in the graphs were carried out at pH 6.5, in FaSSIF.
Figure 2:
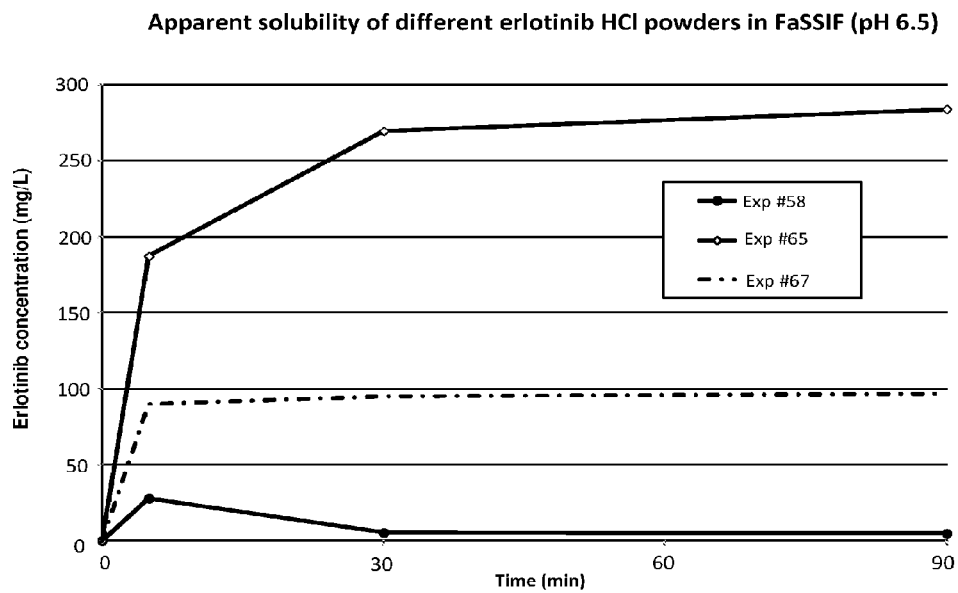
FIG. 2 provides a graph showing the apparent solubility for erlotinib in representative compositions of the invention. Further experimentation with erlotinib is found in Example 2. The details of the stable, amorphous hybrid nanoparticles are described in Example 2, Table 7, for experiment 58, 65 and 67, respectively. Briefly, experiment 65 represents stable, amorphous hybrid nanoparticles with erlotinib HCl and HPMC-AS, wherein the solubilizer polyvinyl caprolactam-polyvinyl acetate-polyethylene glycol copolymer is present separately from the stable, amorphous hybrid nanoparticles. Experiment 58 represents raw, crystalline erlotinib HCl and experiment 67 represents stable, amorphous hybrid nanoparticles of erlotinib HCl, HPMC-AS and the solubilizer polyvinyl caprolactam-polyvinyl acetate-polyethylene glycol copolymer present within the hybrid nanoparticles. The experiments illustrated in the graphs were carried out at pH 6.5 in FaSSIF.
Figure 3:
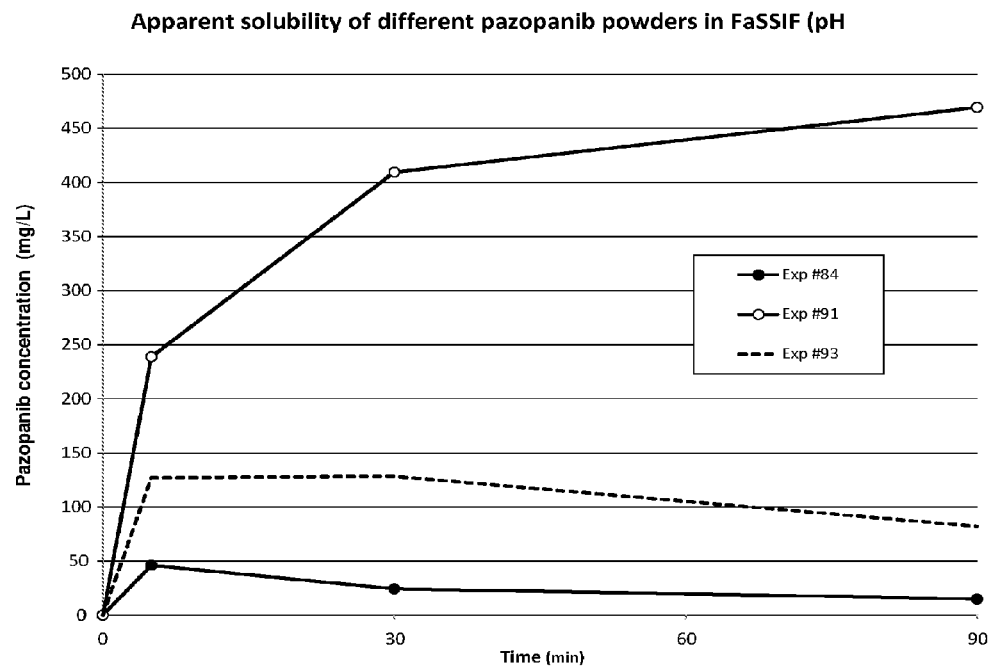
FIG. 3 provides a graph showing the apparent solubility for pazopanib in representative compositions of the invention. Further experimentation with pazopanib is found in Example 3. The details of the stable, amorphous hybrid nanoparticles are described in Example 3, Table 13, for experiment 84, 91 and 93, respectively. Briefly, experiment 91 represents stable, amorphous hybrid nanoparticles comprising pazopanib and PVP 90K and wherein the solubilizer polyvinyl caprolactam-polyvinyl acetate-polyethylene glycol copolymer is present separately from the stable, amorphous hybrid nanoparticles, experiment 93 represents hybrid nanoparticles comprising pazopanib, PVP 90K and the solubilizer polyvinyl caprolactam-polyvinyl acetate-polyethylene glycol copolymer, present within the stable, amorphous hybrid nanoparticles. Experiment 84 represents raw, crystalline pazopanib. The experiments illustrated in the graphs were carried out at pH 6.5, in FaSSIF.
Figure 4:
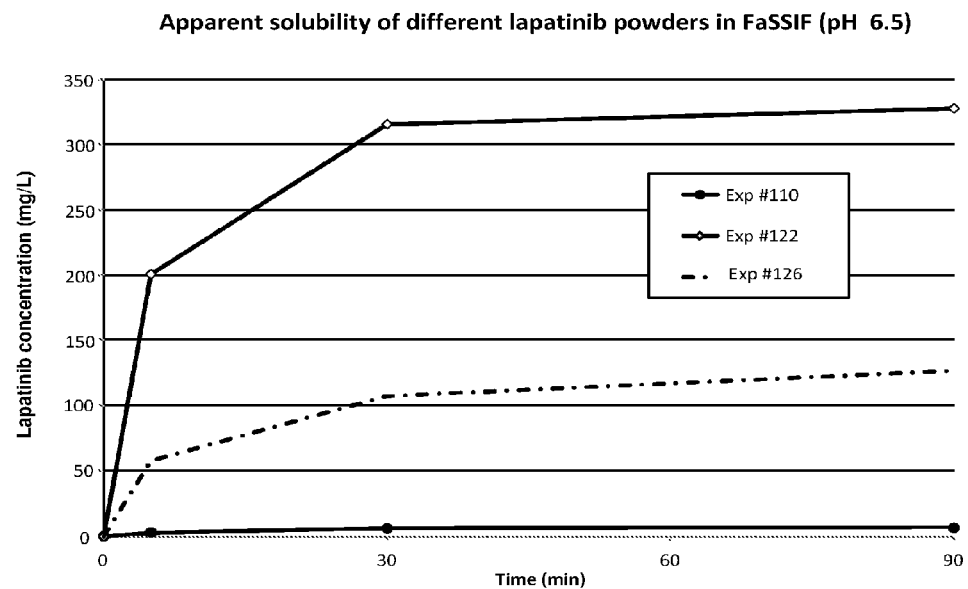
FIG. 4 provides a graph showing the apparent solubility for lapatinib in representative compositions of the invention. Further experimentation with both lapatinib base and lapatinib ditosylate salt is found in Example 4. The details of the stable, amorphous hybrid nanoparticles are described in Example 4, Table 19, for experiment 110, 122 and 126, respectively. Briefly, experiment 122 represents stable, amorphous hybrid nanoparticles comprising lapatinib base and HPC EF, wherein the solubilizer polyvinyl caprolactam-polyvinyl acetate-polyethylene glycol copolymer is present separately from the stable, amorphous hybrid nanoparticles. Experiment 110 represents raw, lapatinib base and experiment 126 represents stable, amorphous hybrid nanoparticles of lapatinib base, HPC LF and the solubilizer polyvinyl caprolactam-polyvinyl acetate-polyethylene glycol copolymer present within the hybrid nanoparticles. The experiments illustrated in the graphs were carried out at pH 6.5 in FaSSIF.
Figure 5:
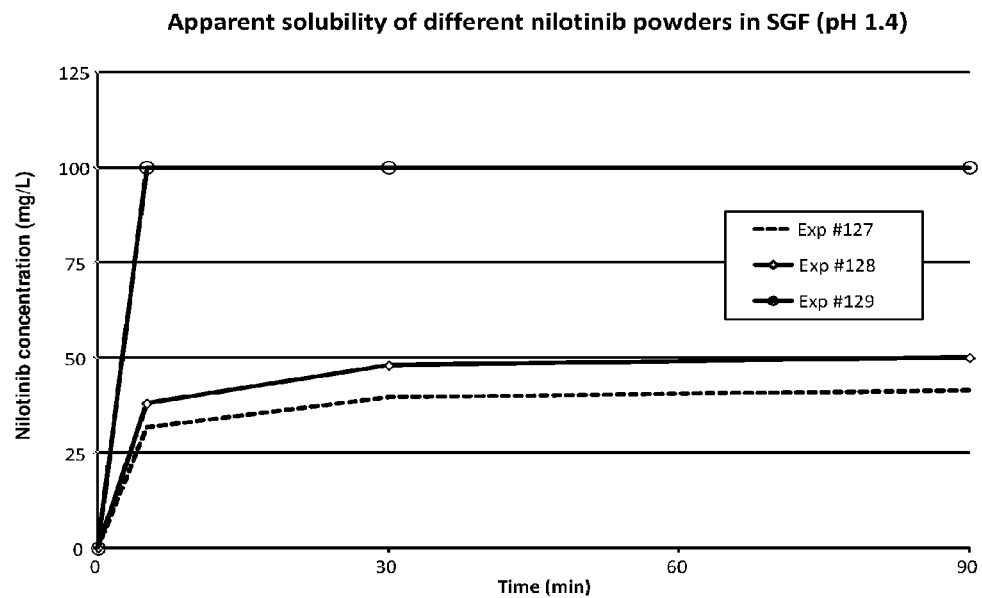
FIG. 5 provides a graph showing the apparent solubility for nilotinib in representative compositions of the invention. The details of the stable, amorphous hybrid nanoparticles are described in Example 5, Table 21, for experiment 127, 128 and 129, respectively. Briefly, experiment 129 represents a physical mixture of raw, crystalline nilotinib HCl, HPMCP HP55 and the solubilizer polyvinyl caprolactam-polyvinyl acetate-polyethylene glycol copolymer. Experiment 128 represents stable, amorphous hybrid nanoparticles comprising nilotinib HCl and HPMCP HP55, wherein the solubilizer polyvinyl caprolactam-polyvinyl acetate-polyethylene glycol copolymer is present separately from the stable, amorphous hybrid nanoparticles. Experiment 127 represents stable, amorphous hybrid nanoparticles of nilotinib HCl and HPMCP HP55. The experiments illustrated in the graphs were carried out at pH 1.4 in SGF.
Figure 6:
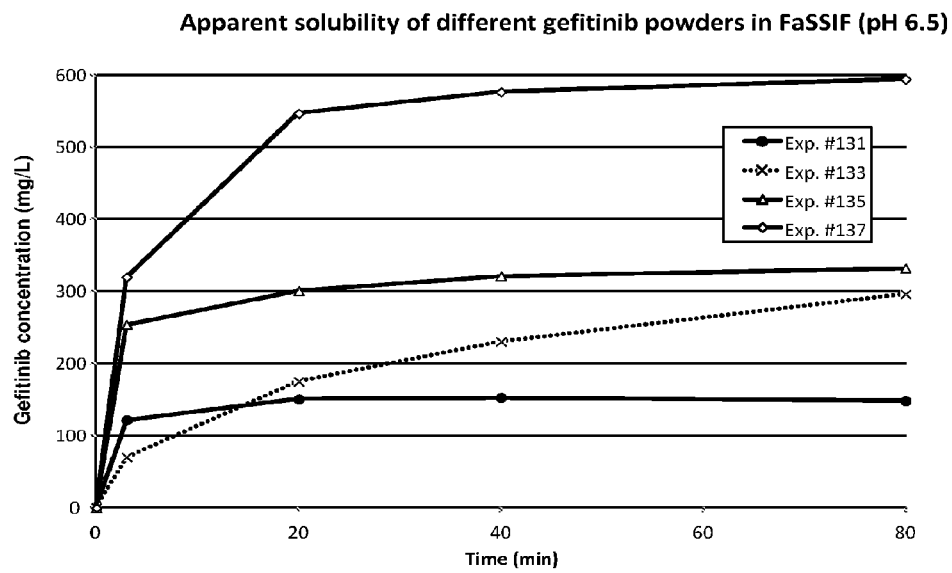
FIG. 6 provides a graph showing the apparent solubility for gefitinib in representative compositions of the invention. Further experimentation with gefitinib is found in Example 6. The details of the compositions are described in Example 6, Table 22, for experiment 131, 133, 135 and 137, respectively. Briefly, experiment 131 represents raw, crystalline gefitinib. Experiment 133 represents a mixture of raw, crystalline gefitinib, HPMCP HP55 and the solubilizer polyvinyl caprolactam-polyvinyl acetate-polyethylene glycol copolymer. Experiment 135 represents stable, amorphous hybrid nanoparticles of gefitinib and HPMCP HP55.
Figure 7:
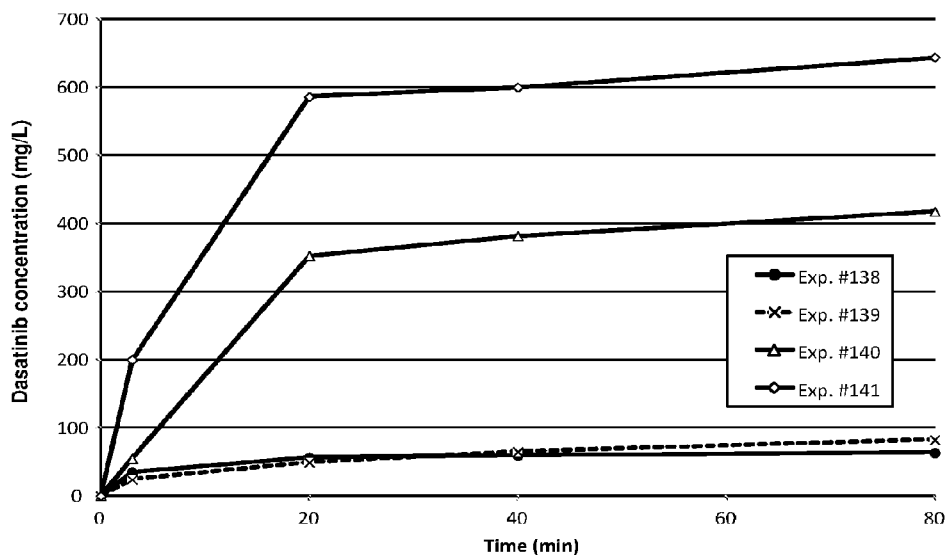

FIG. 7 provides a graph showing the apparent solubility for dasatinib in representative compositions of the invention. The details of the stable, amorphous hybrid nanoparticles are described in Example 7, Table 24, for experiments 138-141. Briefly, experiment 138 represents raw, crystalline dasatinib. Experiment 139 represents a mixture of raw, crystalline dasatinib, Kollidon VA64 and the solubilizer polyvinyl caprolactam-polyvinyl acetate-polyethylene glycol copolymer. Experiment 140 represents hybrid nanoparticles of dasatinib and Kollidon VA64. Experiment 141 represents stable, amorphous hybrid nanoparticles of dasatinib and Kollidon VA64 wherein the solubilizer polyvinyl caprolactam-polyvinyl acetate-polyethylene glycol copolymer is present separately from the stable, amorphous hybrid nanoparticles. The experiments illustrated in the graphs were carried out at pH 6.5 in FaSSIF.

Figure 8:
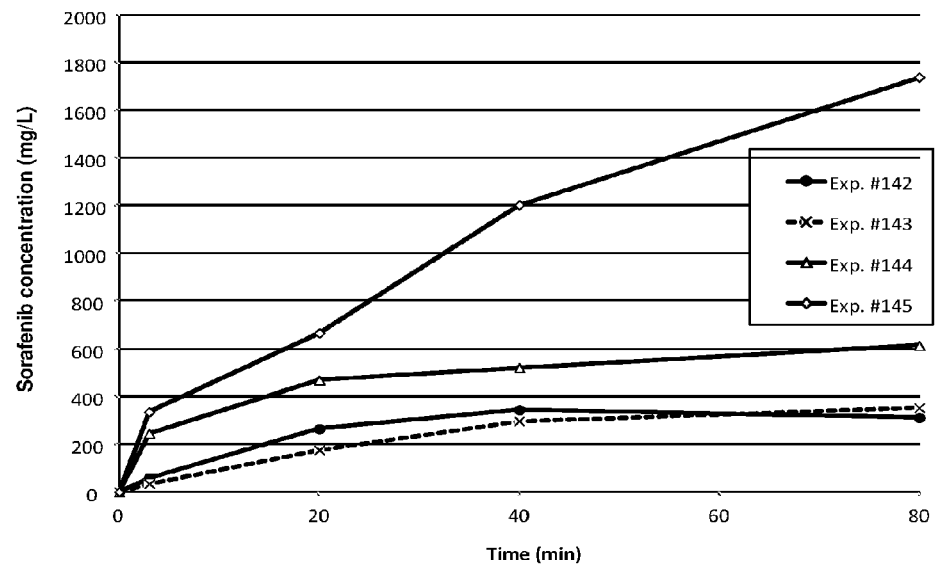

FIG. 8 provides a graph showing the apparent solubility for sorafenib in representative compositions of the invention. The details of the stable, amorphous hybrid nanoparticles are described in Example 8, Table 26, for experiments 142-145. Briefly, experiment 142 represents raw, crystalline sorafenib tosylate. Experiment 143 represents a mixture of raw, crystalline sorafenib tosylate, HPMCP HP55 and the solubilizer polyvinyl caprolactam-polyvinyl acetate-polyethylene glycol copolymer. Experiment 144 represents stable, amorphous hybrid nanoparticles of sorafenib tosylate and HPMCP HP55. Experiment 145 represents hybrid nanoparticles of sorafenib tosylate and HPMCP HP55 wherein the solubilizer polyvinyl caprolactam-polyvinyl acetate-polyethylene glycol copolymer is present separately from the stable, amorphous hybrid nanoparticles. The experiments illustrated in the graphs were carried out at pH 6.5 in FaSSIF.

Figure 9:
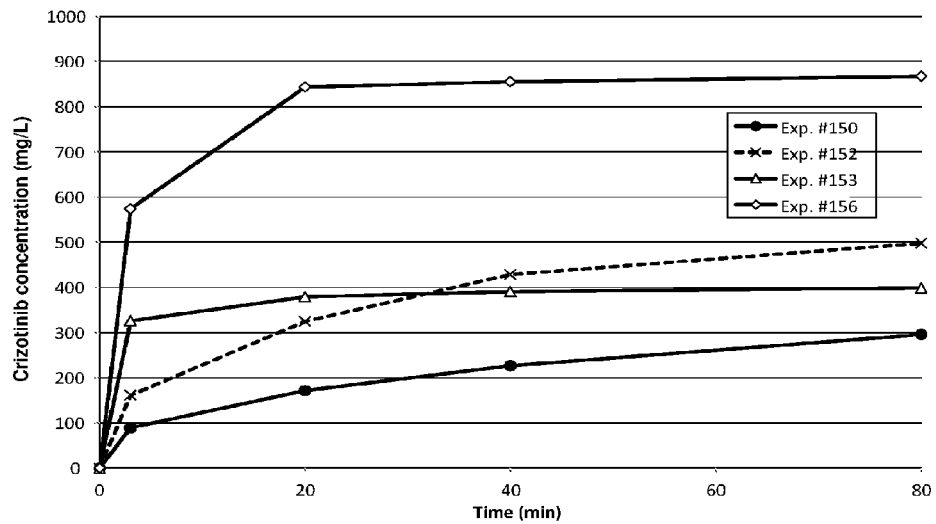

FIG. 9 provides a graph showing the apparent solubility for crizotinib in representative compositions of the invention. Further experimentation with crizotinib is found in Example 10. The details of the compositions are described in Example 10, Table 30, for experiment 150, 152, 153 and 156, respectively. Briefly, experiment 150 represents raw, crystalline crizotinib. Experiment 152 represents a mixture of raw, crystalline crizotinib, PVP 30K and the solubilizer Cremophor RH40. Experiment 153 represents stable, amorphous hybrid nanoparticles of crizotinib and PVP 30K. Experiment 156 represents stable, amorphous hybrid nanoparticles of crizotinib and PVP 30K wherein the solubilizer Cremophor RH40 is present separately from the stable, amorphous hybrid nanoparticles. The experiments illustrated in the graphs were carried out at pH 6.5 in FaSSIF.

Figure 10:
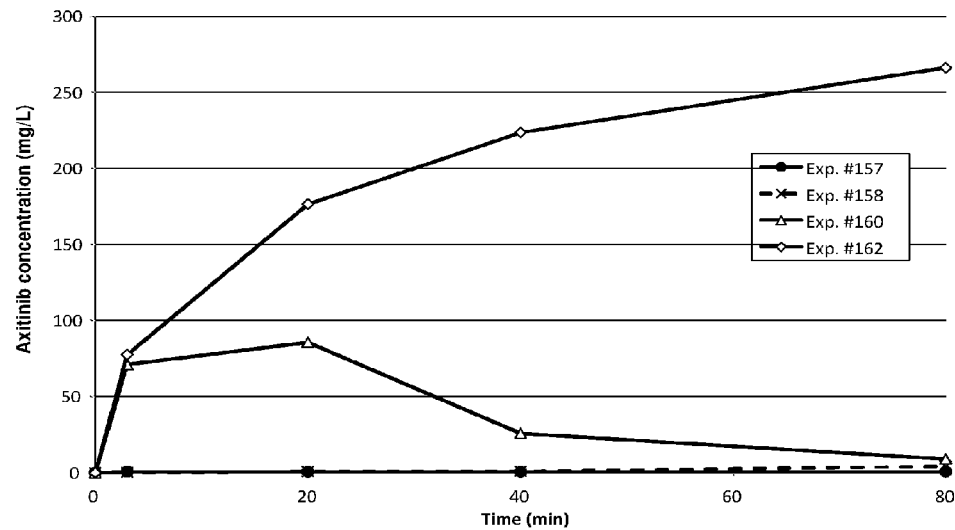

FIG. 10 provides a graph showing the apparent solubility for axitinib in representative compositions of the invention. Further experimentation with axitinib is found in Example 11. The details of the compositions are described in Example 11, Table 32, for experiment 157, 158, 160 and 162, respectively. Briefly, experiment 157 represents raw, crystalline axitinib. Experiment 158 represents a mixture of raw, crystalline axitinib, Kollidon VA64 and the solubilizer polyvinyl caprolactam-polyvinyl acetate-polyethylene glycol copolymer. Experiment 160 represents stable, amorphous hybrid nanoparticles of axitinib and Kollidon VA64. Experiment 162 represents stable, amorphous hybrid nanoparticles of axitinib and Kollidon VA64 wherein the solubilizer polyvinyl caprolactam-polyvinyl acetate-polyethylene glycol copolymer is present separately from the stable, amorphous hybrid nanoparticles. The experiments illustrated in the graphs were carried out at pH 6.5 in FaSSIF.

Figure 11:
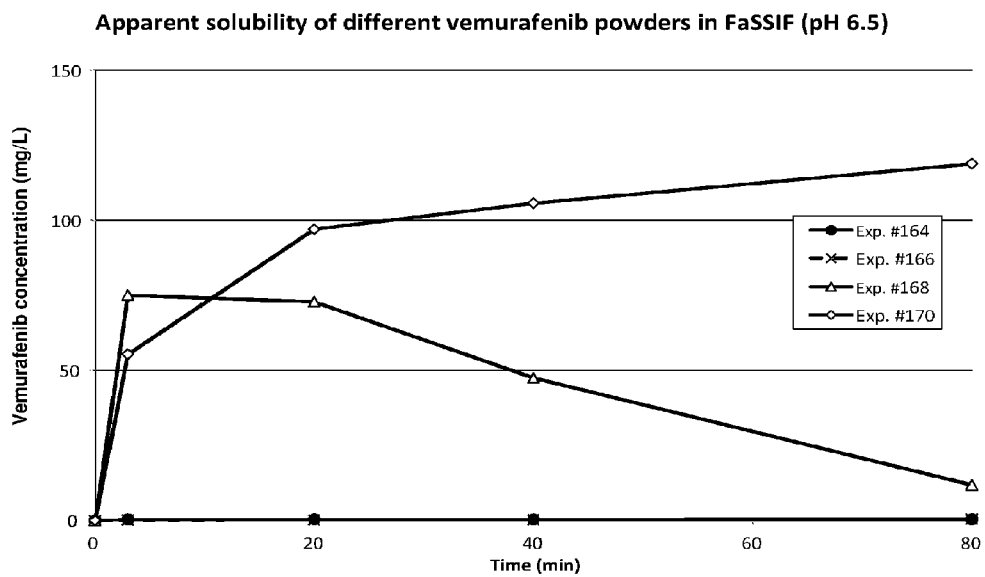

FIG. 11 provides a graph showing the apparent solubility for vemurafenib in representative compositions of the invention. Further experimentation with vemurafenib is found in Example 12. The details of the compositions are described in Example 12, Table 34, for experiment 164, 166, 168 and 170, respectively. Briefly, experiment 164 represents raw, crystalline vemurafenib. Experiment 166 represents a mixture of raw, crystalline vemurafenib, CAP and the solubilizer polyvinyl caprolactam-polyvinyl acetate-polyethylene glycol copolymer. Experiment 168 represents stable, amorphous hybrid nanoparticles of vemurafenib and CAP. Experiment 170 represents stable, amorphous hybrid nanoparticles of vemurafenib and CAP wherein the solubilizer polyvinyl caprolactam-polyvinyl acetate-polyethylene glycol copolymer is present separately from the stable, amorphous hybrid nanoparticles. The experiments illustrated in the graphs were carried out at pH 6.5 in FaSSIF.

Figure 12:
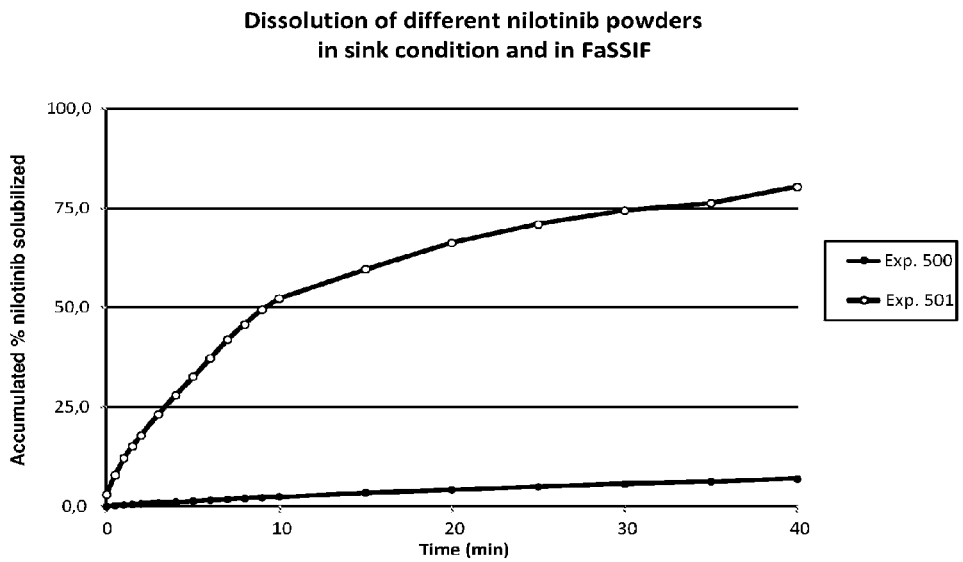

FIG. 12 provides a graph showing the dissolution rate for nilotinib base in representative compositions of the invention, measured under sink conditions. Details are found in Examples 13 and 13.1, and Table 36 for experiments 500 and 501. Briefly, experiment 500 represents raw, nilotinib HCl. Experiment 501 represents stable, amorphous hybrid nanoparticles of nilotinib base and HPMCP HP55. The experiments illustrated in the graphs were carried out at pH 6.5 in FaSSIF.

Figure 13:
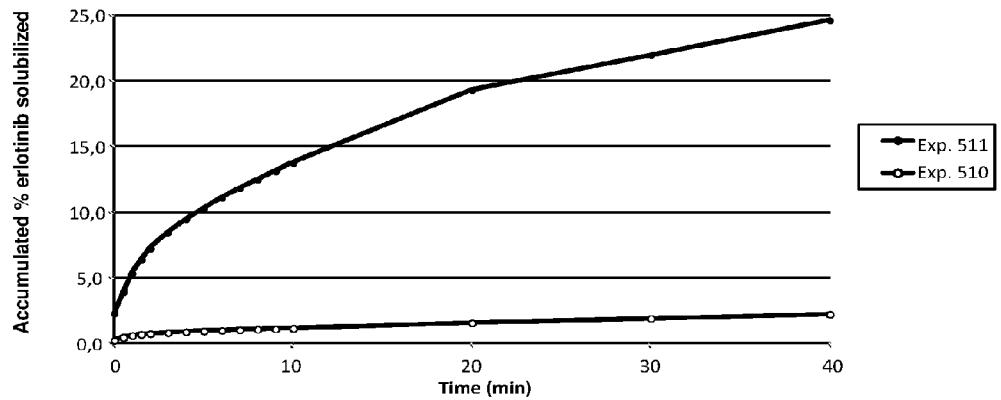

FIG. 13 provides a graph showing the dissolution rate for erlotinib in representative compositions of the invention, measured under sink conditions. Details are found in Examples 13 and 13.2, Table 37 for experiments 510 and 511. Briefly, experiment 510 represents raw, erlotinib HCl. Experiment 511 represents stable, amorphous hybrid nanoparticles of erlotinib HCl and HPMC AS.

Figure 14:
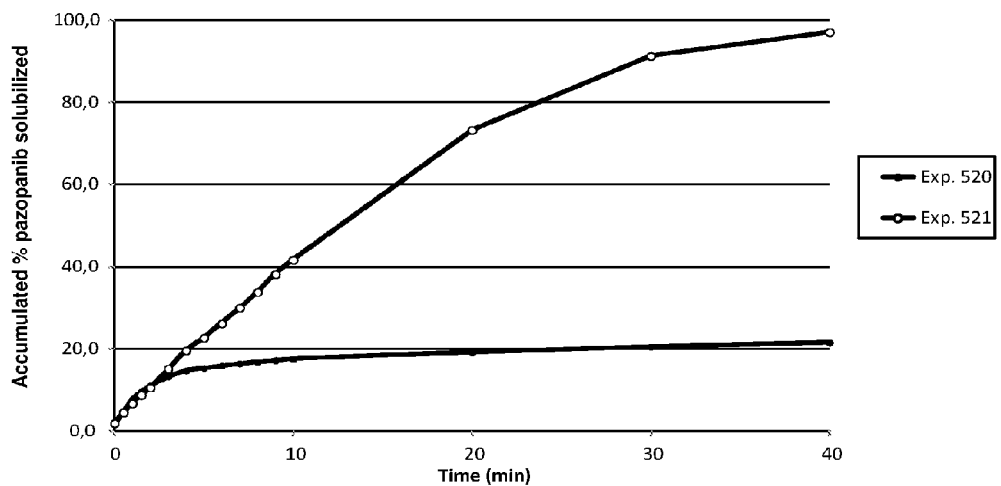

FIG. 14 provides a graph showing the dissolution rate for pazopanib in representative compositions of the invention, measured under sink conditions. Details are found in Examples 13 and 13.3, Table 38 for experiments 520 and 521. Briefly, experiment 520 represents raw, pazopanib HCl. Experiment 521 represents stable, amorphous hybrid nanoparticles of pazopanib HCl and PVP90K.

Figure 15:
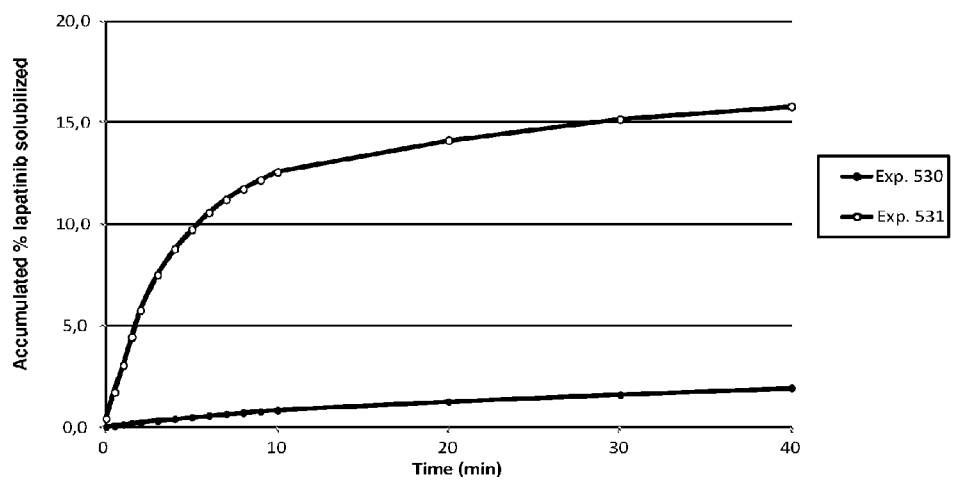

FIG. 15 provides a graph showing the dissolution rate for lapatinib in representative compositions of the invention, measured under sink conditions. Details are found in Examples 13 and 13.4, Table 39 for experiments 530 and 531. Briefly, experiment 530 represents raw, lapatinib ditosylate. Experiment 531 represents stable, amorphous hybrid nanoparticles of lapatinib base and HPC If.

Figure 16:
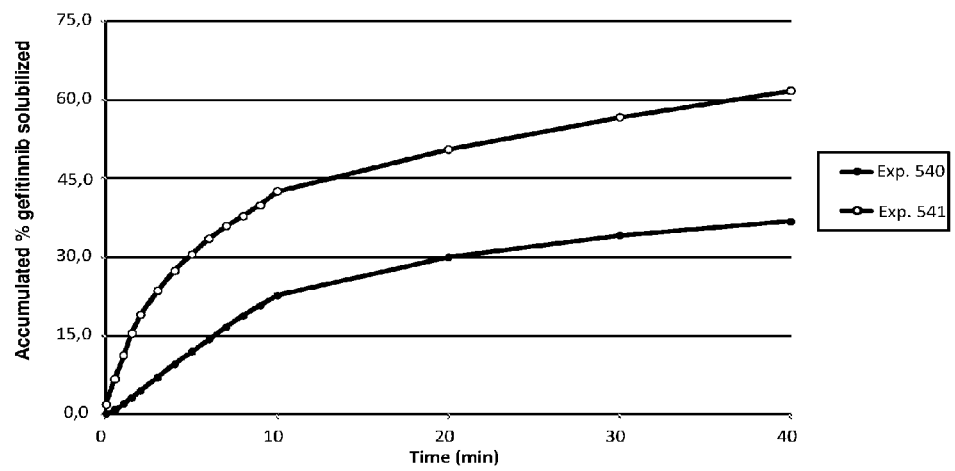

FIG. 16 provides a graph showing the dissolution rate for gefitinib in representative compositions of the invention, measured under sink conditions. Details are found in Examples 13 and 13.5., Table 40 for experiments 540 and 541. Briefly, experiment 540 represents raw, gefitinib. Experiment 541 represents stable, amorphous hybrid nanoparticles of gefitinib and HPMCP HP55.

Figure 17:
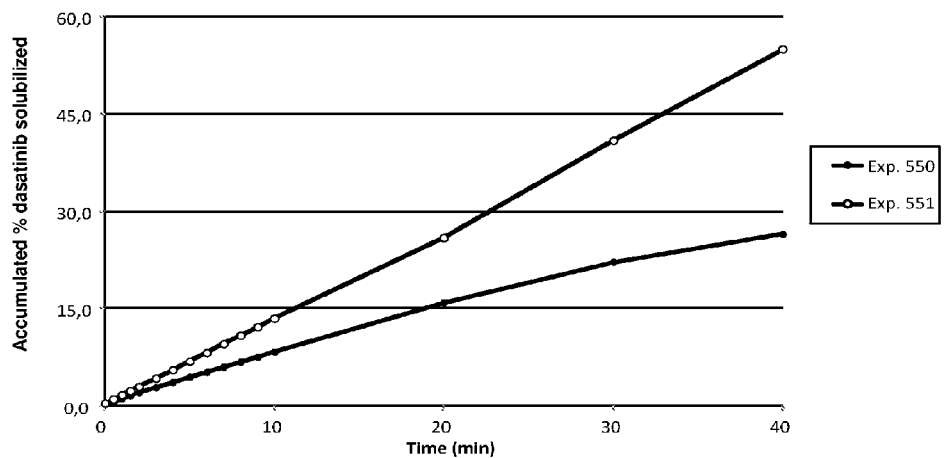

FIG. 17 provides a graph showing the dissolution rate for dasatinib in representative compositions of the invention, measured under sink conditions. Details are found in Examples 13 and 13.6., Table 41 for experiments 550 and 551. Briefly, experiment 550 represents raw, dasatinib. Experiment 551 represents stable, amorphous hybrid nanoparticles of dasatinib and Kollidon VA64.

Figure 18:
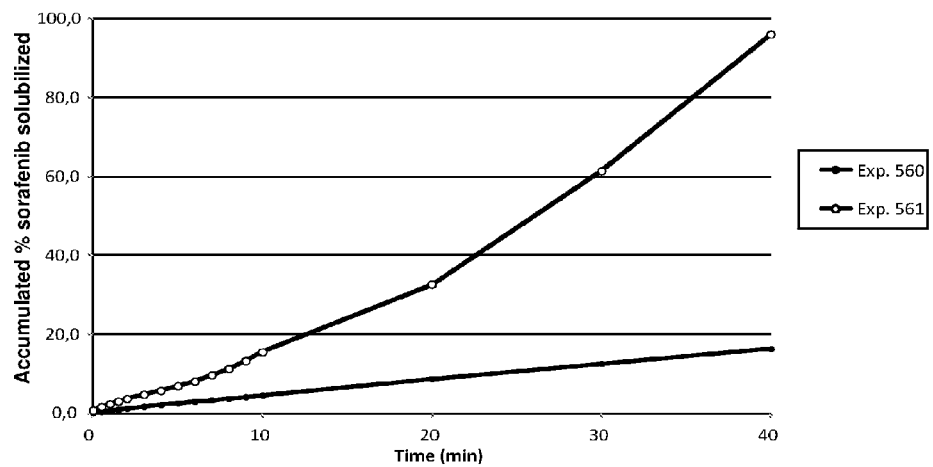

FIG. 18 provides a graph showing the dissolution rate for sorafenib in representative compositions of the invention, measured under sink conditions. Details are found in Examples 13 and 13.7., Table 42 for experiments 560 and 561. Briefly, experiment 560 represents raw, sorafenib tosylate. Experiment 561 represents stable, amorphous hybrid nanoparticles of sorafenib tosylate and HPMCP HP55.

Figure 19:
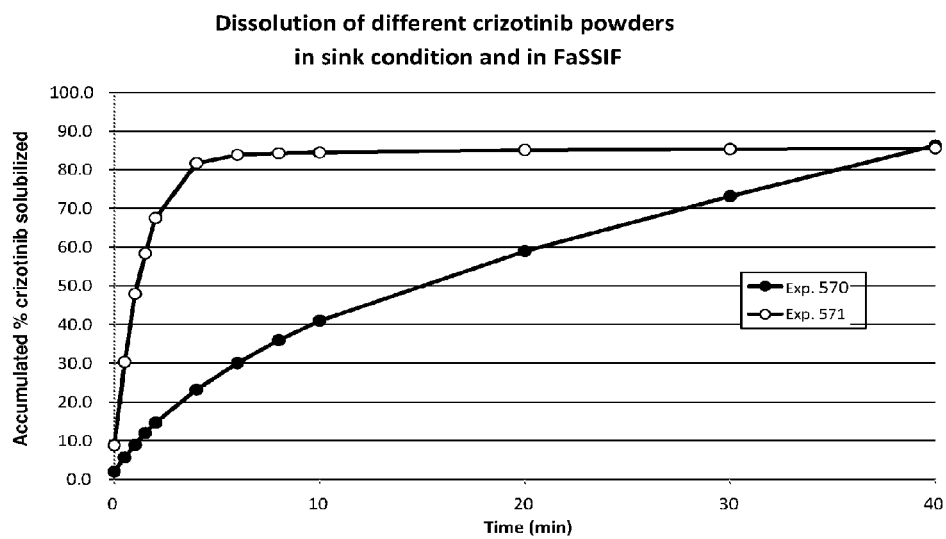

FIG. 19 provides a graph showing the dissolution rate for crizotinib in representative compositions of the invention, measured under sink conditions. Details are found in Examples 13 and 13.8., Table 43 for experiments 570 and 571. Briefly, experiment 570 represents raw, crizotinib. Experiment 571 represents stable, amorphous hybrid nanoparticles of crizotinib and PVP 30K.

Figure 20:
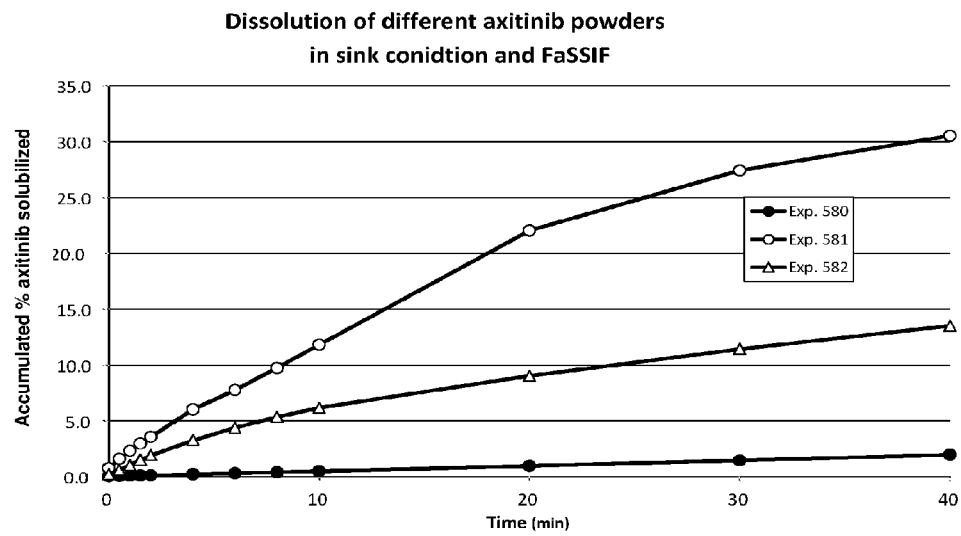

FIG. 20 provides a graph showing the dissolution rate for axitinib in representative compositions of the invention, measured under sink conditions. Details are found in Examples 13 and 13. 9., Table 44 for experiments 580, 581 and 582. Briefly, experiment 580 represents raw, axitinib. Experiment 581 represents hybrid nanoparticles of axitinib and Kollidon VA64 and experiment 582 represents stable, amorphous hybrid nanoparticles of axitinib and HPMC AS.

Figure 21:
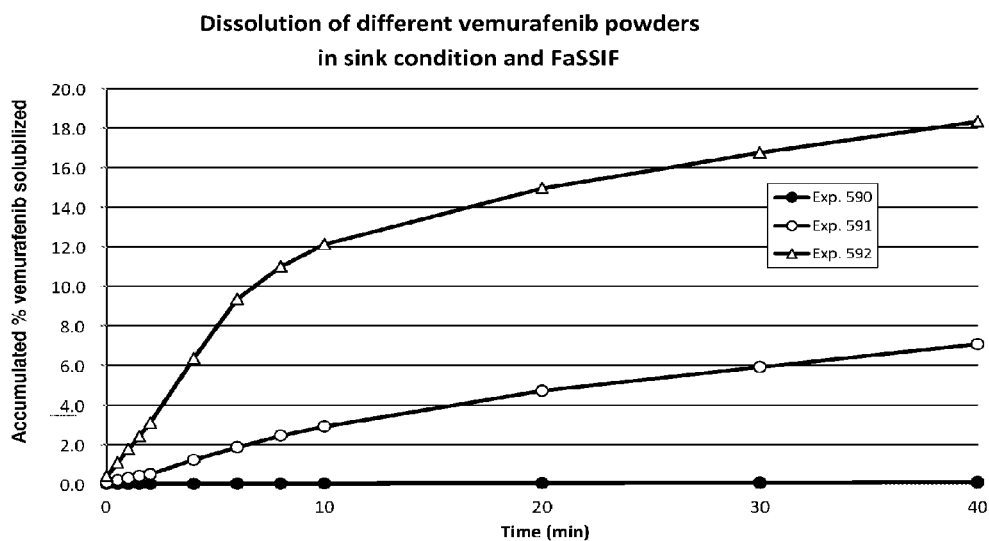

FIG. 21 provides a graph showing the dissolution rate for vemurafenib in representative compositions of the invention, measured under sink conditions. Details are found in Examples 13 and 13.10. Table 45 for experiments 590, 591 and 592. Briefly, experiment 590 represents raw, vemurafenib. Experiment 591 represents hybrid nanoparticles of vemurafenib and Kollidon VA64 and experiment 592 represents stable, amorphous hybrid nanoparticles of vemurafenib and CAP.

Figure 22:
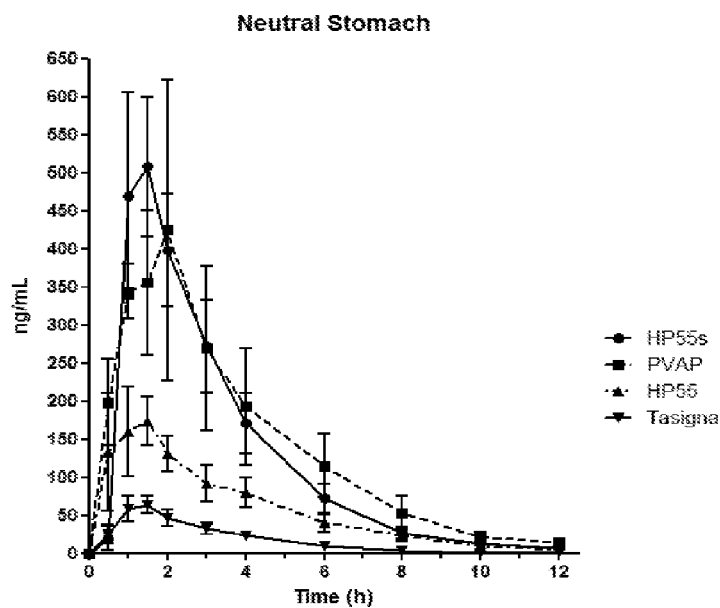

FIG. 22 provides graphs showing in vivo measurement of plasma levels after oral administration to beagle dogs of representative compositions comprising stable, amorphous hybrid nanoparticles of nilotinib base and the polymeric stabilizing and matrix-forming components PVAP and HPMCP HP55, respectively (I/P), denoted PVAP and HP55, as well as wherein the solubilizer polyvinyl caprolactam-polyvinyl acetate-polyethylene glycol copolymer was added (I/P+S), denoted HP55s and PVAPs, respectively. The experiments were carried out in beagle dogs pre-treated to have neutral stomach content. The stable, amorphous hybrid nanoparticles are further described in experiments 146 and 147 (Example 9) and details of the in vivo experiments are set out in Example 14. The experiments used a marketed formulation comprising nilotinib HCl ("Tasigna") as reference.

Figure 23:
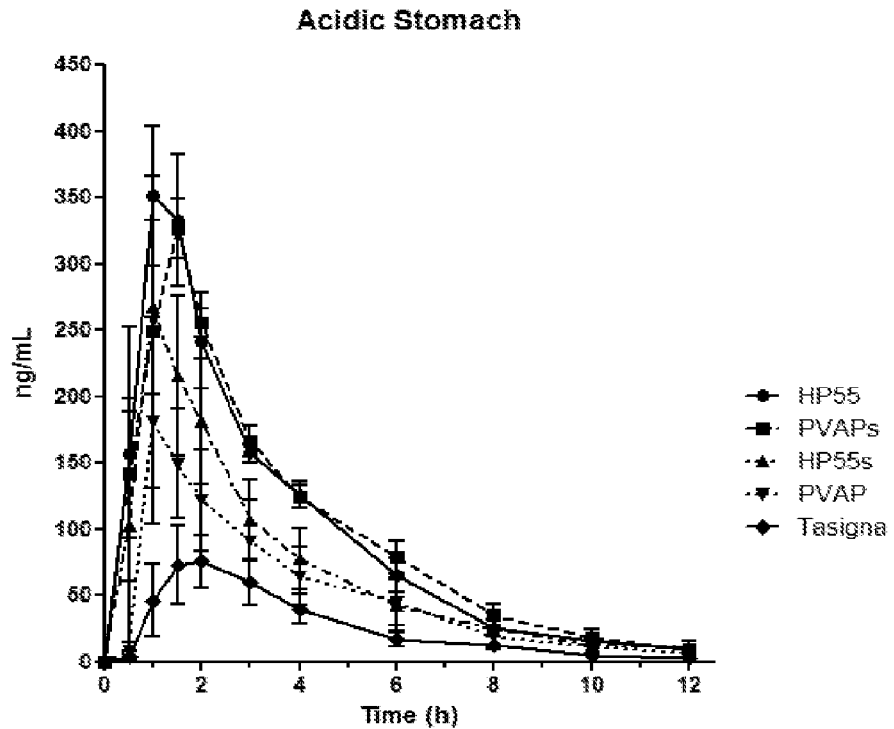

FIG. 23 provides graphs showing in vivo measurement of plasma levels after oral administration to beagle dogs of representative compositions comprising stable, amorphous hybrid nanoparticles of nilotinib base and the polymeric stabilizing and matrix-forming components PVAP and HPMCP HP55, respectively (I/P), denoted PVAP and HP55, as well as wherein the solubilizer polyvinyl caprolactam-polyvinyl acetate-polyethylene glycol copolymer was added (I/P+S) denoted PVAPs and HP55s, respectively. The experiments were carried out in beagle dogs pre-treated to have acidic stomach content. The stable, amorphous hybrid nanoparticles are further described in experiments 146 and 147 (Example 9) and details of the in vivo experiments are set out in Example 14. The experiments used a marketed formulation comprising nilotinib HCl ("Tasigna") as reference.

Figure 24:
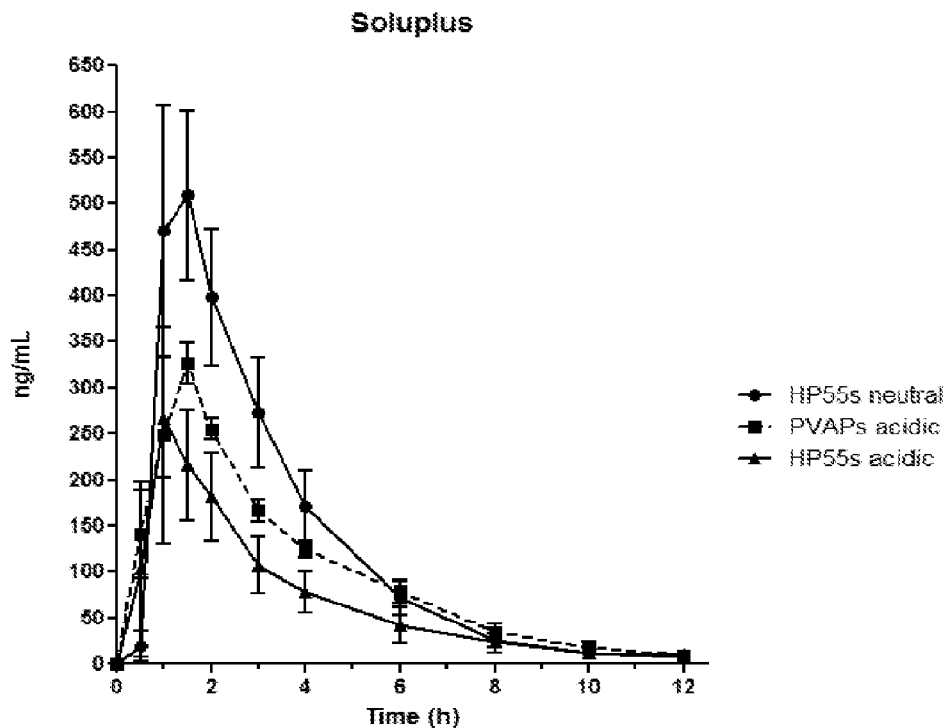

FIG. 24 provides graphs showing in vivo measurement of plasma levels after oral administration to beagle dogs of representative compositions comprising stable, amorphous hybrid nanoparticles of nilotinib base and the polymeric stabilizing and matrix-forming components PVAP and HPMCP HP55, respectively (I/P), denoted PVAP and HP55, as well as wherein the solubilizer polyvinyl caprolactam-polyvinyl acetate-polyethylene glycol copolymer was added after hybrid nanoparticle formation (I/P+S), denoted PVAPs and HP55s, respectively. The experiments were carried out in beagle dogs pre-treated to have acidic or neutral stomach content. The stable, amorphous hybrid nanoparticles are further described in experiments 146 and 147 (Example 9) and details of the in vivo experiments are set out in Example 14.

Figure 25:
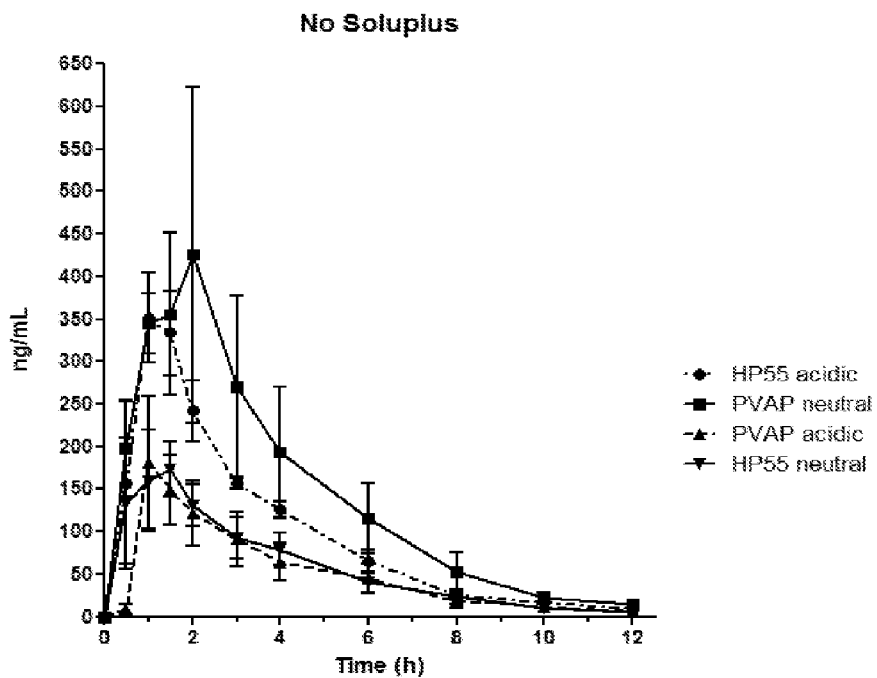

FIG. 25 provides graphs showing in vivo measurement of plasma levels after oral administration to beagle dogs of representative compositions comprising stable, amorphous hybrid nanoparticles of nilotinib base and the polymeric stabilizing and matrix-forming components PVAP and HPMCP HP55, denoted PVAP and HP55, respectively (I/P). The experiments were carried out in beagle dogs pre-treated to have acidic or neutral stomach content. The stable, amorphous hybrid nanoparticles are further described in experiments 146 and 147 (Example 9) and details of the in vivo experiments are set out in Example 14.

Figure 26:
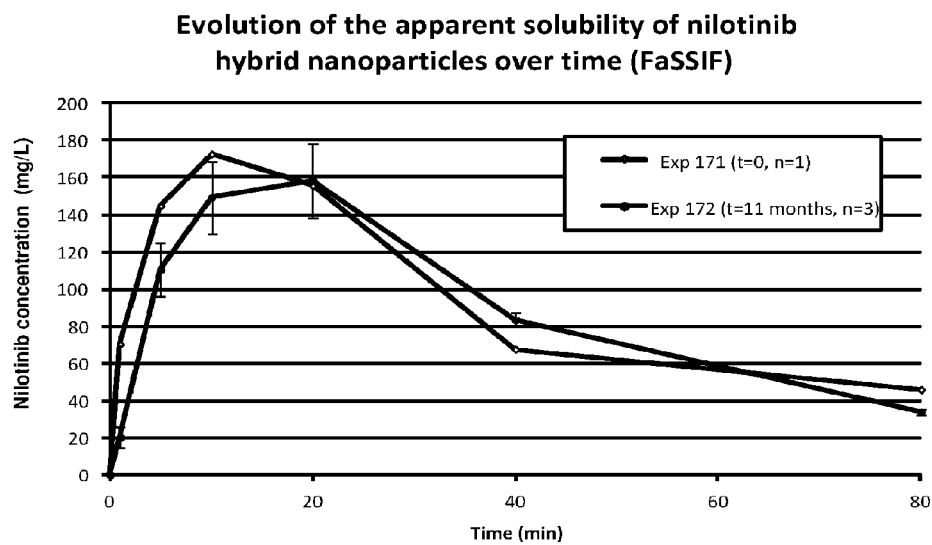

FIG. 26 provides a graph showing the apparent solubility of representative compositions before and after 11 months of storage at room temperature. The experiment provides stable, amorphous hybrid nanoparticles comprising nilotinib base, HPMCP HP55 and the addition of the solubilizer polyvinyl caprolactam-polyvinyl acetate-polyethylene glycol copolymer (I/P+S) as Exp 171 & Exp 172 with further details set out in Example 15.

Figure 27:
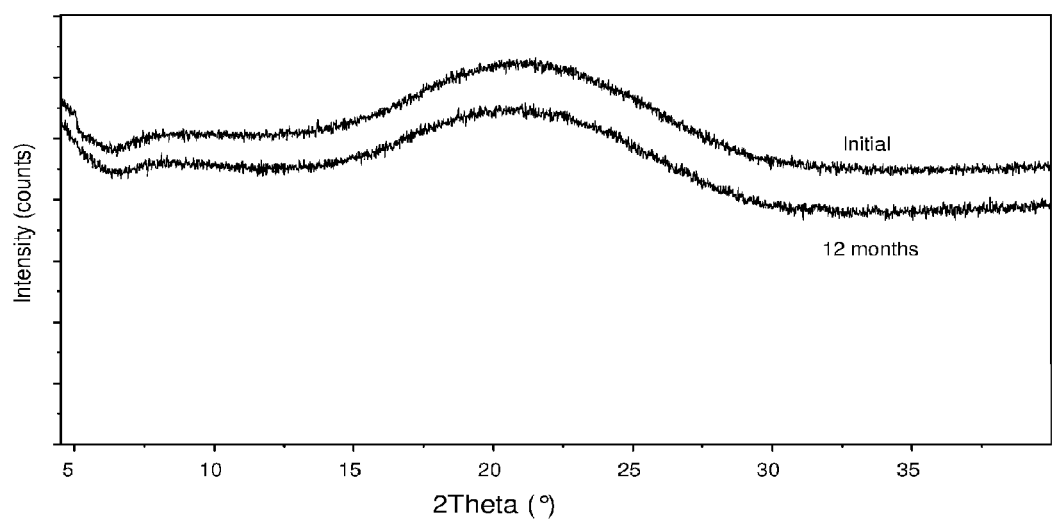

FIG. 27 provides overlayed X-ray powder diffraction (XRPD) patterns of stable hybrid nanoparticles at 40% drug load, UP nilotinib base/HPMCP HP55. Initial (top) and after 12 months storage at ambient temperature (bottom). The XRPD patterns are offset in order improve the visual comparison. Further details are set out in Example 15.

DETAILED DESCRIPTION OF THE INVENTION

All patents, patent applications, and publications cited herein are hereby incorporated by reference in their entirety.

As used herein, the phrase "hybrid nanoparticles" refers to a group of particles, typically in the average size range of from 1 to 1000 nm, composed of at least two components, one of which is the PKI and the other a polymeric stabilizing and matrix-forming component. The particles can be either crystalline or amorphous, or a mixture thereof. Typically, in the sense of the present disclosure, the particles are "amorphous", or "essentially amorphous". This means that almost all, if not all, content of the particles comprise amorphous protein kinase inhibitor and polymeric stabilizing and matrix-forming component. The level or degree of amorphicity is at least 60%, such as 70%, such as 80% or 85%, preferably at least 90% and more preferably >95%, wherein 100% represents that all material is amorphous in the particles.

Quantification of crystalline PKI or absence of crysalline PKI may be measured by X-ray powder diffraction metods as described in Saleki-Gerhardt A et al. Int J Pharm. 1994; 101:237-247) or by water vapor sorption as described in Dash A K et al. J Pharm Sci. 2002 April; 91(4):983-90.

The term "solid dispersion particles" relates to "hybrid nanoparticles" as defined above, however, solid dispersion particles are typically larger or much larger in size (typically μm-mm, as decribed in Wu K. et al. J Pharm Sci. 2009 July; 98(7):2422-3). The smaller size of hybrid nanoparticles contributes to further stabilizing the PKI against crystallization. Typically, hybrid nanoparticles is in the average size range of from 1 to 1000 nm, such as below 500 nm, preferably below 250 nm.

The phrase "stable" refers to the level of stability of produced particles by the methods of the present invention and may be measured as the capability of the hybrid nanoparticles to remain in their physical state for 6-12 months storage at ambient temperature (e.g. 18-25° C.). The level of stability may be measured by AUC measurements of dissolution rate over for instance 80 minutes of the particles, after such storage.

By the phrase "protein kinase inhibitor" or "PKI" is meant a type of enzyme inhibitor that specifically blocks the action of one or more protein kinases. PKIs include, but are not limited, to protein kinase inhibitors and tyrosine kinase inhibitors, such as axitinib, afatinib, bosutinib, crizotinib, cediranib, dasatinib, erlotinib, fostamatinib, gefitinib, imatinib, lapatinib, lenvatinib, lestaurtinib, motesanib, mubritinib, nilotinib, pazopanib, pegaptanib, ruxolitinib, sorafenib, semaxanib, sunitinib, tandunitib, tipifamib, vandetanib and vemurafenib; or salts or hydrates or solvates thereof, or combinations thereof.

By the phrase "polymeric stabilizing and matrix-forming component" is meant the component present in the hybrid nanoparticles together with the PKI. Typically, said polymeric stabilizing and matrix-forming component exhibits a polymeric structure, such as, but not limited to, methyl cellulose, hydroxyethyl cellulose, hydroxypropyl cellulose (e.g. HPC ef, HPC lf and HPC jf), hydroxypropyl methylcellulose (e.g. Methocel E3 and E15 and Pharmacoat), hydroxypropyl methylcellulose acetate succinate (HPMC AS), hydroxypropyl methylcellulose phthalate (e.g. HPMCP-HP55), polyvinylpyrrolidone (e.g. PVP 30K and PVP 90K), polyvinyl acetate phthalate (PVAP), copolyvidone (e.g. Kollidon VA 64), crospovidon (e.g. Kollidon CL), methacrylic acid and ethylacrylate copolymer (e.g. Kollicoat ME), methacrylate acid and methyl methacrylate copolymer (e.g. Eudragit L100), polyethylene glycol (PEG), DL lactide/glycolide copolymer, poly DL-lactide, cellulose acetate phthalate (CAP), aminoalkyl methacrylate copolymers (e.g. Eudragit RL100, RL PO or RS PO), carbomer homopolymer Type A (e.g. Carbopol 971P), carbomer homopolymer Type B (e.g. Carbopol 974P) and Poloxamers (e.g. Pluronics, Kolliphor).

The term "polymer" or "polymeric" is here used to mean a compound that is made of monomers connected together to form a larger molecule. A polymer generally consists of 20 or more monomers connected together, however less than 20 monomers connected together are here also referred to as polymers.

The term "solubilizer" is here used to mean a compound that increases the solubility of a substance, such as, but not limited to, polyvinyl caprolactam-polyvinyl acetate-polyethylene glycol copolymer (Soluplus), d-α-tocopherol acid polyethylene glycol 1000 succinate (TPGS), PEG-40 hydrogenated castor oil (Cremophor RH40), PEG-35 castor oil (Cremophor EL), PEG-40 stearate (MYRJ 540), hard fat (e.g. Gelucire 33/01), polyoxylglycerides (e.g. Gelucire 44/14), stearoyl polyoxylglycerides (e.g. Gelucire 50/13), PEG-8 caprylic/capric glycerides (e.g. Labrasol) and Poloxamers (e.g. Pluronics, Kolliphor).

As used herein, the phrase "primary particles" refers to the smallest particulate entities formed during the precipitation process. The boundaries of the particles are analyzed by SEM microscopy. Depending on process parameters, the primary particles may build together a more or less dense and porous network forming larger, agglomerated or bridging particles. Parameters affecting the agglomeration are e.g. temperature that may modify the softness of the primary particles; ratio solvent/antisolvent affecting precipitation time, concentration of the PKI solution; and the nature of the polymeric stabilizing and matrix-forming agent(s). The average size of the primary particles is typically between 1 to 1000 nm, preferably below 500 nm, more preferably below 250 nm.

As used herein, the phrases "supercritical" and "supercritical fluid" refer to that a chemical substance that is set to both a temperature higher or equal than its critical temperature (Tc) and a pressure higher or equal than its critical pressure (Pc).

As used herein, the phrases "subcritical" and "subcritical fluid" refer here to that one of critical temperature (Tc) or critical pressure (Pc) is set to a temperature or pressure higher than its critical temperature (Tc) or critical pressure (Pc), respectively, and the other of critical temperature (Tc) or critical pressure (Pc) is set to a temperature or pressure lower than its critical temperature (Tc) or critical pressure (Pc), respectively.

By the phrase "area under the curve (AUC)" is meant the area under the concentration-time curve, where the x-axis represents time and the y-axis represents solubilized drug concentration.

By the phrase "apparent solubility" is meant the concentration of material at apparent equilibrium. See further in the Examples section.

The term "supersaturation" is here used to mean that a solution contains more of the dissolved substance than could be dissolved by the solvent or media under normal circumstances.

As used herein, the term "Soluplus" or "soluplus" refers to polyvinyl caprolactam-polyvinyl acetate-polyethylene glycol copolymer.

As used herein, the term "TPGS" refers to d-α-tocopherol acid polyethylene glycol 1000 succinate.

As used herein, the term "Chremophor RH40" refers to PEG-40 hydrogenated castor oil.

As used herein, the term "PVAP" refers to polyvinyl acetate phthalate.

As used herein, the term "PVP 90K" refers to polyvinylpyrrolidone K-90.

As used herein, the term "PVP 30K" refers to polyvinylpyrrolidone K-30.

As used herein, the term "HPMC-AS" refers to hydroxypropyl methylcellulose acetate succinate.

As used herein, the term "HPMCP HP55" refers to hydroxypropyl methyl cellulose phthalate.

As used herein, the term "HPC" refers to hydroxypropyl cellulose, such as HPC EF and HPC LF.

As used herein, the term "Kollidon VA64" refers to copolyvidone.

As used herein, the term "CAP" refers to cellulose acetate phthalate.

The dissolution mediums used for purposes of testing hybrid nanoparticles of the present invention, includes Fasted State Stimulated Intestinal Fluid, referred to as FaSSIF, Fed State Stimulated Intestinal Fluid, referred to as FeSSIF, and Simulated Gastric Fluid, referred to as SGF. FaSSIF media is tailored to represent a fasting state and has a pH of about 6.5 as well as particular osmolaric properties. FeSSIF media is tailored to represent a fed state and has a pH of about 5 as well as specific osmolaric properties. SGF is tailored to represent gastric fluid and has a pH of about 1.4 as well as particular osmolaric properties. FaSSIF, FeSSIF and SGF media are generally used in in vitro models for dissolution of poorly water-soluble drugs. The choice of medium will be dependent of the where in the intestinal tract and under what conditions (fasted or fed) particles are desired to dissolve and be taken up. Further details regarding these fluids are described in e.g. Hervé J. et al. Pharm Dev Technol. 2011 Jun.; 16(3):278-86 and Jantratid, E., and Dressman, J. Dissolut. Technol. 2009 8, 21-25.

By the phrase "amorphous form" is meant non-crystalline solid form. The ease of dissolution may at least in part be attributed to the amount of energy required for dissolution of the components from a crystalline or amorphous solid phase. Amorphous particles require less energy for dissolution as compared to crystalline particles of the same compound.

The inventive compositions comprise particles with a PKI or a combination of two or more PKIs. However, the particles may comprise a combination of one or more PKIs and at least one further active ingredient, such as one or more drugs. Various kinds of PKIs can be effectively utilized.

The term PKIs (protein kinase inhibitors) as used herein, is intended to include also the hydrates, solvates (alcoholates), pharmaceutically acceptable acid salts, base salts or co-crystals of such protein kinase inhibiting compounds.

As used herein, the term water-insoluble or poorly water soluble (or hydrophobic) compounds, refers to compounds whose solubility in water at 25° C. is less than 1 g/100 ml, especially less than 0.1 g/100 ml in pure water at neutral pH.

The stable, amorphous hybrid nanoparticles comprised in the compositions of the present invention are typically in the form of particles as described elsewhere in this specification. There are a number of different methods for the formation of larger particles, e.g. granulation, melt extrusion, spray drying, precipitation etc. all of which typically encompass starting with formation of a mixture between the Active Pharmaceutical Ingredient (API) and the polymeric stabilizing and matrix-forming component. The particles comprised in the compositions of the present invention are produced with continuos processes for generating hybrid nanoparticles. Continuous processes in this context means that particle formation is continuously ongoing while at the same time continuously withdrawing/collecting/retaining hybrid nanoparticles from the mixture after their formation. In the preferred methods, i.e. precipitation methods, this means that a fluid which is a solution of the PKI, preferably in the form of a fluid stream, is mixed with an antisolvent fluid, preferably in the form of an antisolvent fluid stream. The polymeric stabilizing and matrix-forming component may be present in either one or both of the two fluids depending on its solubility characteristics. The mixing of the two fluids is taking place in a mixing function, e.g. a mixing chamber. In the case the process is continuous, i.e. the two fluids are fluid streams, the mixing function typically is associated with a particle formation and separation function wherein the mixed fluid stream may pass through while retaining the hybrid nanoparticles. Agents modifying the particle characteristics without being incorporated into the particles may be added to either one or both of the two fluids before the mixing step. The fluids typically are conventional liquids or supercritical fluids, where supercritical fluids also include subcritical fluids (i.e. fluids for which only one of pressure and temperature is above its supercritical value). Typical combinations are, a) conventional (i.e., non-supercritical) liquids for both the API solution and the antisolvent, b) supercritical solution of the API combined with conventional liquid for the antisolvent, c) conventional liquid for the API solution combined with supercritical fluid for the antisolvent, and d) supercritical fluids for both of the two fluids. In certain variants the antisolvent may be omitted. A fluid stream, preferably supercritical, containing both the API and the polymeric stabilizing and matrix-forming component is then allowed to expand into the particle formation function. It is preferred that at least one of the fluids is in a supercritical state in the precipitation methods described above. These kinds of precipitation methods are discussed in WO 2005061090 (Censdelivery AB), WO 2009072950 (XSpray Microparticles AB), WO 2009072953 (XSpray Microparticles AB), WO 2011159218 (XSpray Microparticles AB) and references cited in these publications.

The term "solution" encompasses that the solute is either a true solute or minute particles of colloidal dimensions (typically 1-1000 nm) and less than the particles to be produced.

A preferred particle formation system is the "Right Size system" developed by XSpray Microparticles AB, Sweden. A detailed description of the technology can be found in the WO-publications given in the preceding paragraph. An important characteristic of the system is that the two fluid streams should merge within a nozzle at an angle in the interval 45°-135°, with preference for about 90° and sprayed into a particle formation/separation function. In principle the system allows for producing particles of predetermined size and/or morphology. Here the Right Size system and apparatus will be described using the non-limiting example of a PKI as the drug and $CO_2$ as a supercritical fluid antisolvent.

The system consists of one pumping set-up for the PKI dissolved in a liquid solvent, referred to as the API solution, and one pumping set-up for an antisolvent, for example $CO_2$, however also other antisolvents may be used when suitable. Each pumping set-up includes instruments such as a flow meter and a pressure meter that are used to control the process conditions. These two pumping set-ups are fluidically connected at a spray nozzle.

A stream of liquid API solution is mixed with a stream of $CO_2$ under flow conditions within the spray nozzle. The polymeric stabilizing and matrix-forming component is present in either the API solution or in the stream of $CO_2$. These streams are sprayed at the outlet of the nozzle into a precipitation vessel under controlled conditions (typically pressure and temperature). $CO_2$ acts as an antisolvent and makes the API to precipitate together with the polymeric stabilizing and matrix-forming component into fine particles. Particles are retained in the vessel by a filtering set-up. A back pressure regulator is typically used to control the pressure inside the precipitation vessel.

For preparing hybrid nanoparticles of certain drugs, for example but not limited to pazopanib and erlotinib, it may be advantageous to have an extra pumping set-up for injecting an additional solvent, referred to as a modifier, into the $CO_2$. Here a pumping set-up control is set up for the modifier and the modifier is mixed with the $CO_2$ in a mixer before entering the nozzle.

When using the system, the system operator typically starts by equilibrating the system by pumping $CO_2$, an "PKI like solution" (a solution similar in composition to the PKI solution but containing no PKI and no excipient) and the modifier (if used) through the system until flow rates, pressure and temperature have reached a desired steady state. Critical parameters for setting up the system are PKI solution composition, PKI solution flow rate, $CO_2$ flow rate, $CO_2$ pressure and temperature, nature of the modifier and modifier flow rate, if such is used.

Next, the "PKI like solution" is exchanged for the PKI solution and particles are produced and retained downstream of the mixing, e.g. downstream of the outlet of the nozzle. Afterwards, the system is typically cleaned by pumping the "PKI like solution" through the system. The particles are dried by flushing $CO_2$ through the retained particles in order to extract any remaining solvent. The precipitation vessel is then depressurized and the particles can be collected.

The solution/solvent and the antisolvent are typically miscible with each other. The pressure and temperature in the particle formation function, and/or upstream of this function, such as in the mixing function, provide supercritical or subcritical conditions in relation to the antisolvent.

The concentration of the PKI in the solution is typically below its saturation concentration, such as ≤50%, such as ≤60%, such as ≤75%, such as ≤85% or such as ≤95% of the saturation concentration. Suitable concentrations are typically found in the interval ≤20%, such as ≤10% or ≥5% or ≤3% with lower limits being ≤005% or 0.1% (all in w/v-%). The term "volatile" for solvents typically means boiling points of 200° C., such as ≤150° C. or ≤100° C., at atmospheric pressure. Examples are inorganic solvents and organic solvents with particular emphasis of dimethyl sulfoxide and trifluoroethanol and mixtures thereof. The term solvent includes mixtures of liquids which are miscible with each other. The solutions may contain agents that enhance or diminish the solubility of the PKI, e.g. acidic, alkaline, buffer components and/or other organic solvents.

Illustrative fluids which can be used as an antisolvent are
 a) gaseous at room temperature and atmospheric pressures, or
 b) liquid at room temperature and atmospheric pressure.

The antisolvent is typically selected for its ability to be readily dispersed into small droplets and for its ability to act as an atomizing agent and antisolvent against the PKI present in the solution.

Compounds/elements according to group (a) may be selected from carbon dioxide (Pc=74 bar and Tc=31° C.) (preferred), nitrous oxide (Pc=72 bar and Tc=36° C.), sulphur hexafluoride (Pc=37 bar and Tc=45° C.), ethane (Pc=48 bar and Tc=32° C.), ethylene (Pc=51 bar and Tc=10° C.), xenon (Pc=58 bar and Tc=16° C.), trifluoromethane (Pc=47 bar and Tc=26° C.), chlorotrifluoromethane (Pc=39 bar and Tc=29° C.) and nitrogen (Pc=34 bar and Tc=−147° C.) and mixtures containing these compounds/elements. Pc stands for critical pressure and Tc for critical temperature. Compounds according to group (b) are typically selected amongst conventional liquids of the same general types as discussed for solvents above but with the difference that the PKI present in the solution must be poorly soluble in the antisolvent. Particular liquids of group (b) comprise methanol, ethanol, acetone water and mixtures containing one or more of these fluids.

The antisolvents of group (a) above are typically used at pressures and temperatures providing i) supercritical conditions (supercritical fluid) or ii) a subcritical conditions (subcritical fluid) in the particle formation function and/or upstream of this function, such as in the mixing function and upstream of this latter function.

Variant (i) means pressures and temperatures which are typically above the critical pressure Pc and critical temperature Tc of the antisolvent used. For the pressure this typically means pressures in the interval (1.0-7.0)×Pc or in the interval ≥10 bar, suitably ≥20 bar with preference for ≥30 bar, higher than Pc with illustrative upper limits being 100 bar, 200 bar and 300 bar higher than Pc. For the temperature this typically means temperatures within (1.0-4.0)×Tc or in the interval of ≥5° C., suitably ≥10° C. with preference for ≥15° C. above Tc with illustrative upper limits being 10° C., 40° C. and 50° C. above Tc.

Variant (ii) means that at least one of temperature and pressure, with preference for only the temperature, is/are below the critical value. (Tc and Pc, respectively). Thus the temperature may be in the interval of (0.1-1)×Tc, such as (0.5-1)×Tc, or lower. Further, the temperature may be low, such as −10° C. or −30° C. These temperatures may be combined with pressures as defined in the preceding paragraph or with pressures lower than the Pc of the used antisolvent. For carbon dioxide this means that the temperature in the particle formation function is <+31° C., such as about +25° C. or lower combined with a pressure above or below 74 bar.

The antisolvents of group (b) above are typically used in the subcritical state, i.e. as a subcritical fluid.

In one aspect of the invention, there is provided a pharmaceutical composition comprising stable, amorphous hybrid nanoparticles of at least one protein kinase inhibitor and at least one polymeric stabilizing and matrix-forming component; which composition optionally further comprises at least one pharmaceutically acceptable solubilizer.

In one embodiment of this aspect, there is provided a pharmaceutical composition comprising stable, amorphous hybrid nanoparticles of at least one protein kinase inhibitor and at least one polymeric stabilizing and matrix-forming component; which composition further comprises at least one pharmaceutically acceptable solubilizer. Typically, said solubilizer is present separated from the hybrid nanoparticles in the composition. Or, typically, said solubilizer is distributed to the surface of the hybrid nanoparticles. Said solubilizer may be selected from polyvinyl caprolactam-polyvinyl acetate-polyethylene glycol copolymer, d-α-tocopherol acid polyethylene glycol 1000 succinate and a hydrogenated castor oil, such as PEG-40 hydrogenated castor oil or PEG-35 hydrogenated castor oil. Furthermore, said solubilizer may be a poloxamer.

The compositions comprising stable, amorphous hybrid nanoparticles comprising at least one protein kinase inhibitor and at least one polymeric stabilizing and matrix-forming component, display increased dissolution rate.

Consequently, in another embodiment of this aspect, there is provided a composition comprising stable, amorphous hybrid nanoparticles, comprising at least one protein kinase inhibitor and at least one polymeric stabilizing and matrix-forming component, wherein said hybrid nanoparticles display an increased dissolution rate of said protein kinase inhibitor, compared to the dissolution rate of said protein kinase inhibitor in raw, crystalline form.

Typically, said dissolution rate is measured by a flow through cell system in sink conditions, e.g., according to the US Pharmacopea (USP4). Dissolution measurement in sink conditions of hybrid nanoparticles may be measured in a method consisting of adding the wished amount of powder into a flow through cell system (SOTAX, Allschwill, Switzerland), mounting the cell onto its apparatus and then pumping the appropriate medium (typically FaSSIF, FeSSIF, SGF) through the powder. The temperature of the apparatus is typically set to 37° C. The amount of powder added into the cell depends on drug load of the powder: The exact amount of powder can be calculated from results obtained from drug load analysis of the powders. The PKI may be added into the flow through cell and a flow rate between 5 and 25 ml medium/min is pumped through the powder. One ml samples of the medium passing through the cell is collected at predetermined times and subsequently analyzed by HPLC (e.g. C18 column Eclipse, 4.6 mm×15 cm, 1 ml/min, detection 254 to 400 nm). Samples are typically taken after 0, 0.5, 1, 1.5, 2, 3, 4, 5, 6, 7, 8, 9, 10, 15, 20, 25, 30, 35 and 40 min from the moment the medium comes out from the flow through cell. The accumulated % solubilized of the amount of active substance added into the flow through cell can be calculated and plotted against time (min). The initial slope ("initial dissolution rate", representing 0-10 minutes) of the graph may be estimated and taken as the dissolution rate of the material in sink condition at 37° C. in the given dissolution medium.

Preferably, the dissolution rate is measured within the initial 0 to 10 minutes of dissolution.

The increased dissolution rate is preferably measured in a solution as a dissolution rate ratio of said stable, amorphous hybrid nanoparticles and said protein kinase inhibitor in raw, crystalline form. Preferably said ratio is from about 1.5:1 to about 500:1, such as from about 10:1 to about 30:1.

Preferably, the dissolution rate is measured in a solution with intestinal pH, such as FaSSIF or FeSSIF or in a solution with gastric pH, such as SGF.

Typically, said dissolution rate is measured by a flow through cell system, for instance in sink conditions. Dissolution measurement in sink conditions of stable, amorphous hybrid nanoparticles may be measured in a method consisting of adding the wished amount of powder into a flow through cell system (SOTAX, Allschwill, Switzerland), mounting the cell onto its apparatus and then pumping the appropriate medium (typically FaSSIF, FeSSIF, SGF) through the powder. The temperature of the apparatus is typically set to 37° C. The amount of powder added into the cell depends on drug load of the powder: The exact amount of powder can be calculated from results obtained from drug load analysis of the powders. The PKI may be added into the flow through cell and a flow rate between 5 and 25 ml medium/min is pumped through the powder. One ml samples of the medium passing through the cell is collected at predetermined times and subsequently analyzed by HPLC (e.g. C18 column Eclipse, 4.6 mm×15 cm, 1 ml/min, detection 254 to 400 nm). Samples are typically taken after 0, 0.5, 1, 1.5, 2, 3, 4, 5, 6, 7, 8, 9, 10, 15, 20, 25, 30, 35 and 40 min from the moment the medium comes out from the flow through cell. The accumulated % solubilized of the amount of active substance added into the flow through cell, can be calculated and plotted against time (min). The initial slope ("initial dissolution rate", representing 0-10 minutes) of the graph can be estimated and taken as the dissolution rate of the material in sink condition at 37° C. in the given dissolution medium.

In another embodiment of this aspect, there is provided a composition comprising stable, amorphous hybrid nanoparticles, comprising at least one protein kinase inhibitor and at least one polymeric stabilizing and matrix-forming component, which provides a solubility increase of inhibitor in a solution, said increase measured as the area under the curve (AUC) during about from 40 minutes to about 90 minutes, in said solution as compared with the AUC of inhibitor in raw, crystalline form. Typically, said increase is from about 2:1 to about 10 000:1, wherein 1 represents AUC of inhibitor in raw, crystalline form. The increase may be measured in a solution with intestinal pH, such as FaSSIF or FeSSIF, or in a solution with gastric pH, such as SGF.

The polymeric stabilizing and matrix-forming component of the present invention includes, but not limited to, methyl cellulose, hydroxyethyl cellulose, hydroxypropyl cellulose (e.g. HPC ef, HPC lf and HPC jf), hydroxypropyl methylcellulose (e.g. Methocel E3 and E15 and Pharmacoat), hydroxypropyl methylcellulose acetate succinate (HPMC AS), hydroxypropyl methylcellulose phthalate (e.g. HPMCP HP55), polyvinylpyrrolidone (e.g. PVP 30K and PVP 90K), polyvinyl acetate phthalate (PVAP), copolyvidone (e.g. Kollidon VA 64), crospovidon (e.g. Kollidon CL), methacrylic acid and ethylacrylate copolymer (e.g. Kollicoat ME), methacrylate acid and methyl methacrylate copolymer (e.g. Eudragit L100), polyethylene glycol (PEG), DL lactide/glycolide copolymer, poly DL-lactide, cellulose acetate phthalate (CAP), carbomer homopolymer Type A (Carbopol 971P), carbomer homopolymer Type B (Carbopol 974P), aminoalkyl methacrylate copolymers (e.g. Eudragit RL100, RL PO or RS PO) and Poloxamers (e.g. Pluronics, Kolliphor).

Consequently, in another embodiment of this aspect, said polymeric stabilizing and matrix-forming component is selected from methyl cellulose, hydroxyethyl cellulose, hydroxypropyl cellulose, hydroxypropyl methylcellulose, hydroxypropyl methylcellulose acetate succinate, hydroxypropyl methylcellulose phthalate, polyvinylpyrrolidone, polyvinyl acetate phthalate, copolyvidone, crospovidon, methacrylic acid and ethylacrylate copolymer, methacrylate acid and methyl methacrylate copolymer, polyethylene glycol, DL lactide/glycolide copolymer, poly DL-lactide, cellulose acetate phthalate, carbomer homopolymer Type A, carbomer homopolymer Type B, aminoalkyl methacrylate copolymers and polaxamers. Preferably, said polymeric stabilizing and matrix-forming component is selected from hydroxypropyl methylcellulose phthalate, hydroxypropyl cellulose, copolyvidon, hydroxypropyl methylcellulose acetate succinate, polyvinyl acetate phthalate, cellulose acetate phthalate and polyvinylpyrrolidone.

In another embodiment of this aspect, there is provided a composition comprising stable, amorphous hybrid nanoparticles comprising at least one protein kinase inhibitor and at least one polymeric stabilizing and matrix-forming component, characterized by providing an amorphous powder X-ray diffraction pattern.

In another embodiment of this aspect, there is provided a composition comprising stable, amorphous hybrid nanoparticles comprising at least one protein kinase inhibitor and at least one polymeric stabilizing and matrix-forming component, wherein the dissolution rate of said stable, amorphous hybrid nanoparticles remain stable to at least about 90%, after 6 months of storage or more, at room temperature.

In another embodiment of this aspect, said protein kinase inhibitor is a tyrosine kinase inhibitor selected from the group consisting of lapatinib, pazopanib, nilotinib, erlotinib, dasatinib, gefitinib, sorafenib, crizotinib, vemurafenib and axitinib; or salts or hydrates or solvates thereof, or combinations thereof. In some embodiments it may be advantageous to use other PKIs. Examples of PKI include, but are not limited to afatinib, bosutinib, cediranib, fostamatinib, imatinib, lenvatinib, lestaurtinib, motesanib, mubritinib, pegaptanib, ruxolitinib, semaxanib, sunitinib, tandunitib, tipifarnib and vandetanib; or salts or hydrates or solvates thereof, or combinations thereof.

In another embodiment of this aspect, said stable, amorphous hybrid nanoparticles has an average particle diameter size of less than about 1000 nm, such as less than about 500 nm, preferably less than 250 nm.

In another embodiment of this aspect, said solvent is an organic solvent selected from DMSO and trifluoroethanol, or a mixture of these solvents, or mixture of these solvents with other organic solvent such as DMSO/acetone, DMSO/tetrahydrofurane or trifluoroethanol/ethyl acetate.

The compositions of the present invention may also dissolve and the protein kinase inhibitor may be systemically absorbed independently of the pH in the surrounding environment, and typically approximately in equal amounts, especially at both a gastric pH, such as from about pH 1.2 to about pH 2.1, preferably about 1.7 and at a intestinal pH such as from about pH 4.5 to about pH 8, preferably at a pH of about 6. With systemically absorbed, is meant that the protein kinase inhibitor is released from the stable, amorphous hybrid nanoparticles and taken up by the systemic blood stream. Therefore, in another embodiment of this aspect, there is provided a composition, wherein said protein kinase inhibitor is systemically absorbed independently of the pH. Typically, said protein kinase inhibitor is systemically absorbed with approximately equal amounts at both a gastric pH and at an intestinal pH. Preferably, said acid pH is about pH 1.4 and preferably said neutral pH is about pH 6.5.

With approximately equal amounts is meant that the concentration of protein kinase inhibitor in the blood stream, after exposure is approximately similar. This may be illustrated by a ratio, wherein the concentration of protein kinase inhibitor in the blood stream is measured after administration in gastric pH conditions (A) and compared with the concentration of protein kinase inhibitor in the blood stream is measured after administration in intestinal pH conditions (N). Typically, the ratio A:N is from about 0.75:1 to about 1.5:1 and preferably from about 1:1 to about 1.25:1. The concentration measurement of protein kinase inhibitor in the blood stream may be carried out as an area under the curve (AUC) during 0-24 hours, the maximum concentration (Cmax) or as bioavailability.

Consequently, in another embodiment of this aspect, there is provided a composition comprising stable, amorphous hybrid nanoparticles, comprising at least one protein kinase inhibitor and at least one polymeric stabilizing and matrix-forming component, wherein the concentration of systemically absorbed protein kinase inhibitor in gastric pH conditions compared with the concentration of systemically absorbed protein kinase inhibitor in intestinal pH conditions is in a ratio of from about 0.75:1 to about 1.5:1, preferably of from about 1:1 to about 1.25:1. Typically said gastric pH condition represents a pH of about 1.4 and said intestinal pH condition represents a pH of about 6. Typically, the concentration is measured as area under the curve (AUC) during 0-24 hours of exposure of the composition or as the maximum concentration (Cmax).

The amounts of systemically absorbed protein kinase inhibitor may be measured in various ways. There is provided, in Example 14 in the present disclosure, a method for measurement of systemically absorbed protein kinase inhibitors at various pHs, i.e. under both acid and neutral conditions.

In another embodiment of this aspect, there is provided a composition comprising stable, amorphous hybrid nanoparticles, comprising at least one protein kinase inhibitor and at least one polymeric stabilizing and matrix-forming component, which produces a solubility increase of inhibitor in a solution up to supersaturation, said increase measured as the area under the curve (AUC) during about 90 minutes, in said solution and compared with the AUC of inhibitor in crystalline form. Said increase may be from to about 2:1 to about 1000:1, wherein 1 represents AUC of inhibitor in crystalline form.

For understanding how the hybrid nanoparticles in the compositons of the invention will dissolve in vivo in the different environments of the stomach, small intestine, large intestine and colon, it is important to choose an appropriate solution for in vitro dissolution testing. It is critical that the in vitro test conditions mimic the in vivo environment as closely as possible, for example pH and osmolarity. Typically, for intestinal uptake, the pH is between 6 and 7. Therefore, the solution may hold a pH from about pH 6 to about pH 7, such as about pH 6.5.

Therefore, in embodiments of the invention, the solution for testing has a pH from about pH 4.5 to about pH 8, such as about pH 6.5 or such as about pH 5. The solutions may represent Fasted Simulated State Intestinal Fluid (FaSSIF) or Fed Simulated State Intestinal Fluid (FeSSIF).

Typically, for gastric uptake, the pH is between 1 and 2. Therefore, the solution may hold a pH from about pH 1 to about pH 2, such as about pH 1.4. Therefore, in embodiments of the invention, the solution for testing may represent Simulated Gastric Fluid (SGF).

The choice of solution will be dependent on where in the intestinal tract and under what conditions (fasted or fed) the composition is desired to dissolve and be taken up. Recepies and preparation of these solutions are obtainable from the manufacturer (Biorelevant, Croydon, U.K.). Further details are also disclosed in Jantratid, E., and Dressman, J. (2009) *Dissolut. Technol.* 8, 21-25).

The amount of PKI in the hybrid nanoparticles in the compositions of the present invention may be less or more, such as wherein the amount of PKI in the hybrid nanoparticles is from about 0.01% by weight to about 99.9% by weight.

In another embodiment of this aspect, there is provided compositions comprising stable, amorphous hybrid nanoparticles of the present invention, wherein the amount of PKI in the hybrid nanoparticles is from about 10% by weight to about 70% by weight.

In another embodiment of this aspect, there is provided compositions comprising stable, amorphous hybrid nanoparticles of the present invention, wherein the amount of PKI in the hybrid nanoparticles is from about 10% by weight to about 50% by weight.

In some embodiments, it may be advantageous that the amount of PKI in the stable, amorphous hybrid nanoparticles is from 5% by weight to about 50% by weight, from 10% by weight to about 40% by weight, from about 10% by weight to about 30% by weight, or from about 10% by weight to about 20% by weight.

Control of the characteristics of the particles may be convenient for specific applications. Particle size, particle agglomeration, particles porosity and the choice and ratio of the polymeric stabilizing and matrix-forming agent could be modified in order to increase or decrease the surface area to volume ratio of the particle or behaviour of the particles in a gastroinstestinal fluids, leading to an increase or decrease of the dissolution rate. Dependent on the desired dissolution characteristics such particles characteristics may be adapted. Furthermore, particles with differents characteristics may be present in the same pharmaceutical composition to provide an initial dose and a prolonged or delayed dose of active ingredient. Additionally, it may be advantageous to provide different PKIs and/or other active ingredient(s) in different primary particles with different characteristics adapted to provide desired dissolution rates for each active ingredient(s).

Other embodiments of the invention provide pharmaceutical compositions comprising the stable, amorphous hybrid nanoparticles. Such compositions may further comprise at least one pharmaceutically acceptable solubilizer. Said solubilizer may be present separated from the stable, amorphous hybrid nanoparticles (i.e. physically mixed with pre-prepared solid nanoparticles) in the composition or be randomly intermixed within the stable, amorphous hybrid nanoparticles in the pharmaceutical composition. The pharmaceutical composition may also be in a dosage form consisting of several layers, for example laminated or multilayered tablets, such that the hybrid nanoparticles are separated from the solubilizer. The solubilizer may be selected from polyvinyl caprolactam-polyvinyl acetate-polyethylene glycol copolymer, d-α-tocopherol acid polyethylene glycol 1000 succinate and a hydrogenated castor oil, such as PEG-40 hydrogenated castor oil or PEG-35 hydrogenated castor oil. Said solubilizer may also be a poloxamer.

In another embodiment of this aspect, said inhibitor is a tyrosine kinase inhibitor selected from the group consisting of lapatinib, pazopanib, nilotinib, erlotinib, dasatinib, gefitinib, sorafenib axitinib, crizotinib and vemurafenib; or salts or hydrates or solvates thereof, or combinations thereof.

In another embodiment of this aspect, said inhibitor is nilotinib; and said polymeric stabilizing and matrix-forming component is hydroxy propyl methyl cellulose phthalate or polyvinyl acetate phthalate.

In another embodiment of this aspect, said inhibitor is nilotinib; said polymeric stabilizing and matrix-forming component is hydroxy propyl methyl cellulose phthalate or polyvinyl acetate phthalate; and said solubilizer is polyvinyl caprolactam-polyvinyl acetate-polyethylene glycol copolymer or d-α-tocopherol acid polyethylene glycol 1000 succinate.

In another embodiment of this aspect, said inhibitor is erlotinib, and said polymeric stabilizing and matrix-forming component is hydroxypropyl methylcellulose acetate succinate.

In another embodiment of this aspect, said inhibitor is erlotinib; said polymeric stabilizing and matrix-forming component is hydroxypropyl methylcellulose acetate succinate; and said solubilizer is polyvinyl caprolactam-polyvinyl acetate-polyethylene glycol copolymer or d-α-tocopherol acid polyethylene glycol 1000 succinate.

In another embodiment of this aspect, said inhibitor is pazopanib; and said polymeric stabilizing and matrix-forming component is polyvinylpyrrolidone.

In another embodiment of this aspect, said inhibitor is pazopanib; said polymeric stabilizing and matrix-forming component is polyvinylpyrrolidone; and said solubilizer is polyvinyl caprolactam-polyvinyl acetate-polyethylene glycol copolymer or d-α-tocopherol acid polyethylene glycol 1000 succinate.

In another embodiment of this aspect, said inhibitor is lapatinib; and said polymeric stabilizing and matrix-forming component is hydroxypropyl cellulose.

In another embodiment of this aspect, said inhibitor is lapatinib; said polymeric stabilizing and matrix-forming component is hydroxypropyl cellulose; and said solubilizer is polyvinyl caprolactam-polyvinyl acetate-polyethylene glycol copolymer or d-α-tocopherol acid polyethylene glycol 1000 succinate.

In another embodiment of this aspect, said inhibitor is gefitinib; and said polymeric stabilizing and matrix-forming component is hydroxy propyl methyl cellulose phthalate or polyvinyl acetate phthalate or polyvinylpyrrolidone.

In another embodiment of this aspect, said inhibitor is gefitinib; said polymeric stabilizing and matrix-forming component is hydroxy propyl methyl cellulose phthalate or polyvinyl acetate phthalate or polyvinylpyrrolidone; and said solubilizer is polyvinyl caprolactam-polyvinyl acetate-polyethylene glycol copolymer.

In another embodiment of this aspect, said inhibitor is dasatinib; and said polymeric stabilizing and matrix-forming component is copolyvidone.

In another embodiment of this aspect, said inhibitor is dasatinib; said polymeric stabilizing and matrix-forming component is copolyvidone; and said solubilizer is polyvinyl caprolactam-polyvinyl acetate-polyethylene glycol copolymer.

In another embodiment of this aspect, said inhibitor is sorafenib; and said polymeric stabilizing and matrix-forming component is hydroxy propyl methyl cellulose phthalate.

In another embodiment of this aspect, said inhibitor is sorafenib; said polymeric stabilizing and matrix-forming component is hydroxy propyl methyl cellulose phthalate; and said solubilizer is polyvinyl caprolactam-polyvinyl acetate-polyethylene glycol copolymer.

In another embodiment of this aspect, said inhibitor is nilotinib base; and said polymeric stabilizing and matrix-forming component is hydroxy propyl methyl cellulose phthalate or polyvinyl acetate phthalate.

In another embodiment of this aspect, said inhibitor is nilotinib base; said polymeric stabilizing and matrix-forming component is hydroxy propyl methyl cellulose phthalate or polyvinyl acetate phthalate; and said solubilizer is polyvinyl caprolactam-polyvinyl acetate-polyethylene glycol copolymer.

In another embodiment of this aspect, said inhibitor is axitinib; and said polymeric stabilizing and matrix-forming component is copolyvidone or hydroxypropyl methylcellulose acetate succinate.

In another embodiment of this aspect, said inhibitor is axitinib; said polymeric stabilizing and matrix-forming component is copolyvidone or hydroxypropyl methylcellulose acetate succinate; and said solubilizer is polyvinyl caprolactam-polyvinyl acetate-polyethylene glycol copolymer.

In another embodiment of this aspect, said inhibitor is crizotinib; and said polymeric stabilizing and matrix-forming component is copolyvidone or polyvinylpyrrolidone.

In another embodiment of this aspect, said inhibitor is crizotinib; said polymeric stabilizing and matrix-forming component is copolyvidone or polyvinylpyrrolidone; and said solubilizer is polyvinyl caprolactam-polyvinyl acetate-polyethylene glycol copolymer or PEG-40 hydrogenated castor oil.

In another embodiment of this aspect, said inhibitor is vemurafenib; and said polymeric stabilizing and matrix-forming component is copolyvidone or cellulose acetate phthalate.

In another embodiment of this aspect, said inhibitor is vemurafenib; said polymeric stabilizing and matrix-forming component is copolyvidone or cellulose acetate phthalate; and said solubilizer is polyvinyl caprolactam-polyvinyl acetate-polyethylene glycol.

In another embodiment of this aspect, said protein kinase inhibitor is partially released from the composition, at a pH of from about 1 to about 2, preferably at about pH 1.4.

In another aspect of the invention, there is provided stable, amorphous hybrid nanoparticles, comprising at least one protein kinase inhibitor and at least one polymeric stabilizing and matrix-forming component, as defined in the present disclosure.

In another embodiment of this aspect, there is provided a composition of the invention, for use in therapy.

In another embodiment of this aspect, there is provided a composition of the invention, for use in the treatment of proliferative disorders. Typically, said proliferative disorder is selected from tumours and cancers, including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/ pharynx cancer, esophageal cancer, larynx cancer, lymphoma, multiple myeloma; cardiac hypertrophy, age-related macular degeneration and diabetic retinopathy.

In another embodiment of this aspect, there is provided a composition of the invention, said composition is provided during food intake.

In another aspect of the invention, there is provided a method of treating proliferative disorder in a patient in need thereof, comprising administering a therapeutically effective amount of a composition according to the present invention. Said proliferative disorder is typically selected from tumours and cancers including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

It will be appreciated that the amount of a protein kinase inhibitor in the stable, amorphous hybrid nanoparticles of the present invention required for use in treatment will vary not only with the particular inhibitor selected but also with the route of administration, the nature of the condition for which treatment is required and the age, weight and condition of the patient and will be ultimately at the discretion of the attendant physician. In general however a suitable dose may be in the range of from about 0.005 to about 30 mg/kg of body weight per day, preferably in the range of 0.05 to 10 mg/kg/day.

The desired dose is conveniently presented in a single dose or as a divided dose administered at appropriate intervals, for example as two, three, four or more doses per day. Dependent on the need of the treatment and/or prevention, the desired dose may also be, for example, once every two days, once every three days, or even once a week.

The composition is conveniently administered in unit dosage form; for example containing 0.5 to 1500 mg, conveniently 1 to 1000 mg, most conveniently 5 to 700 mg of active ingredient per unit dosage form. The compositions of the invention will normally be administrated via the oral, parenteral, intravenous, intramuscular, subcutaneous or other injectable ways, buccal, rectal, vaginal, transdermal and/or nasal route and/or via inhalation, in a pharmaceutically acceptable dosage form. Depending upon the disorder and patient to be treated and the route of administration, the compositions may be administered at varying doses.

Pharmaceutical compositions include but are not limited to those suitable for oral, rectal, nasal, topical (including buccal and sub-lingual), transdermal, vaginal or parenteral (including intramuscular, subcutaneous and intravenous) administration or in a form suitable for administration by inhalation or insufflation. The compositions may, where appropriate, be conveniently presented in discrete dosage units and may be prepared by any of the methods well known in the art of pharmacy. Pharmaceutical compositions suitable for oral administration are conveniently presented as discrete units such as capsules, cachets or tablets, each containing a predetermined amount of the active substance.

Tablets and capsules for oral administration may contain conventional excipients such as binding agents, fillers, lubricants, disintegrants, or wetting agents. The tablets may be coated according to methods well known in the art.

The compositions may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents.

The above described compositions may be adapted to give sustained release of the active inhibitor.

The following examples are provided to illustrate various embodiments of the present invention and shall not be considered as limiting in scope.

EXAMPLES

Below follows a number of non-limiting examples of compositions comprising stable, amorphous hybrid nanoparticles. In the tables, the following abbreviations to "compositions" apply:

"I" represents the protein kinase inhibitor (PKI);
"P" represents the polymeric stabilizing and matrix-forming component;
"S" represents the solubilizer;
"I+P" represents a physical mix of the inhibitor with the polymeric stabilizing and matrix-forming component, i.e. without further processing;
"I+S" represents a physical mix of the inhibitor with the solubilizer;
"I+P+S" represents a physical mix of the inhibitor, the polymeric stabilizing and matrix-forming component and the solubilizer;
"I/P" represents stable, amorphous hybrid nanoparticles with the inhibitor and the polymeric stabilizing and matrix-forming component;
"I/P+S" represents stable, amorphous hybrid nanoparticles with the inhibitor and the polymeric stabilizing and matrix-forming component and a separate solubilizer added;
"I/P/S" represents stable, amorphous hybrid nanoparticles with the inhibitor, the polymeric stabilizing and matrix-forming component and the solubilizer.
"Exp" represents the experiment number.

The stable, amorphous hybrid nanoparticles were produced with exemplary PKIs, polymeric stabilizing and matrix-forming components ("Polymers"), solubilizers, solution concentrations, ratios, solvents, antisolvents, temperatures and pressures as set out below and in Table A.

A 3-6% w/v PKI/polymer solution in solvent, with a ratio PKI/polymer of about 20-70% w/w, was pumped through XSpray's RightSize nozzle at the flow rate of 1 ml/min using a high-performance liquid chromatography pump, together with a 100 g/min $CO_2$ (super- or subcritical) stream. The pressure in the precipitation chamber was set to about 100-175 bar and the temperature was set to about 10 to 50° C. Both streams contact within the nozzle and the hybrid nanoparticles were formed and subsequently collected in the particle in the collecting chamber. The $CO_2$ and solvent passed through the filtering system of the collecting chamber and were drained via the back pressure regulator outlet which maintains the pressure within the precipitation and collecting chambers. After pumping of the PKI/polymer solution and cleaning of the tubing with the same solvent used to prepare the PKI/polymer solution, residual solvents left within both the precipitation and collecting chambers were removed by flushing these chambers with pure $scCO_2$. After the flushing process, the $CO_2$ was slowly drained off from the collecting chamber. Once the $CO_2$ had been completely removed, the particles on the filtering system were collected for analysis.

For I/P/S type particles, a defined amount of solubilizer is added and dissolved into the PKI/polymer solution before pumping the solution through the nozzle for precipitation according to the methods described above.

For I/P+S type particles, a defined amount of solubilizer is added to the stable, amorphous hybrid nanoparticles in a glass vial. The glass vial is slowly rotated for mixing of the solubilizer with the hybrid nanoparticles.

TABLE A

Stable, amorphous hybrid nanoparticles with exemplary PKIs, polymeric stabilizing and matrix-forming components, solvents, antisolvents and conditions.

| PKI/Polymer | Exp. # | Solution conc. % (w/v) | Ratio PKI/Polymer % (w/w) | Solvent & Antisolvent | Temperature & Pressure |
|---|---|---|---|---|---|
| Axitinib/ Kollidon VA64 | 160, 162 & 581 | 5% | 25% | DMSO & $CO_2$ | 25° C. & 125 Bars |
| Crizotinib/ PVP 30K | 153, 155, 156 & 571 | 5% | 25% | DMSO & $CO_2$ | 25° C. & 125 Bars |
| Dasatinib/ Kollidon VA64 | 140, 141 & 551 | 4% | 35% | DMSO/Acetone (1:2) & $CO_2$ | 15° C. & 125 Bars |
| Erlotinib HCl/ HPMC AS | 511 | 3.6% | 35% | TFE & $CO_2$ | 25° C. & 150 Bars |
| Gefitinib/ HPMCP HP55 | 135, 137 & 541 | 4% | 35% | DMSO/Acetone (1:2) & CO2 | 40° C. & 150 Bars |
| Lapatinib base/ HPC lf | 531 | 5% | 66% | DMSO/Acetone (1:2) & CO2 | 40° C. & 150 Bars |
| Nilotinib base/ HPMCP HP55 | 501 | 5% | 40% | TFE & $CO_2$ | 15° C. & 125 Bars |
| Pazopanib HCl/ PVP 90K | 521 | 3.6% | 35% | TFE & $CO_2$ | 25° C. & 150 Bars |
| Sorafenib tosylate/ HPMCP HP55 | 561 | 4% | 35% | DMSO/Acetone (1:2) & CO2 | 40° C. & 150 Bars |
| Vemurafenib/ CAP | 168, 170 & 592 | 5% | 25% | DMSO & $CO_2$ | 25° C. & 125 Bars |

General Description of Dissolution Measurement Assay

The method consists of adding the wished amount of powder of stable, amorphous hybrid nanoparticles into a glass vial and then pouring in it the appropriate medium (typically FaSSIF, FeSSIF or SGF). The medium was prepared in accordance with the manufacturer's instructions. The amount of powder added depends on the wished "total PKI concentration". For some experiments where powders with high drug loads were tested and compared, the real amount of PKI in the stable, amorphous hybrid nanoparticles was not taken in account. For other experiments, the drug load was first estimated by HPLC and the amount of powder to obtain the drug concentration was calculated.

Typically, the powder was added in a 8 mL glass bottle and 7 mL of solution was added (typically FaSSIF, FeSSIF or SGF). The glass bottle was put on a shaker (approximately 1 rotation per minute) for dissolution. Samples of 500 µl where taken after different times, and subsequently centrifuged at approximately 15000 g for 3 minutes. The resulting supernatant was then analyzed by HPLC ($C_{18}$ column Eclipse, 4.6 mm×15 cm, 1 mL/min, detection at 254-400 nM. Generally samples were taken after 5, 30 and 90 min and eventually 150 min.

Example 1

Compositions with Stable, Amorphous Hybrid Nanoparticles with Nilotinib—Solubility at pH 6.5 and pH 5

A number of experiments were carried out, wherein nilotinib base or nilotinib HCl represented the protein kinase inhibitor. The experiments were carried out by measuring concentration of solubilized PKI (mg/L) after 5, 30 and 90 minutes dissolution in a solution at about pH 6.5, namely FaSSIF (Fasted State Simulated Intestinal Fluid). Further, experiments were carried out in an alternative solution at about pH 5, namely FeSSIF (Fed State Simulated Intestinal Fluid). Samples of the solution were taken at various time intervals and the amount of protein kinase inhibitor was measured by the dissolution measurement assay described above.

Representative results in FaSSIF solution are provided below in Table 1 and 2, where Table 1 provides data of concentration of nilotinib HCl (mg/L) after 5, 30 and 90 minutes dissolution, whereas Table 2 provides data of % solubilized nilotinib HCl after 30 minutes dissolution, the Area Under the Curve (AUC—mg/min/L) during 90 minutes dissolution and the AUC increase of stable, amorphous hybrid nanoparticles, compared to nilotinib HCl in raw, crystalline form added to the solution (experiments 1-40). In Tables 3 and 4, there is provided dissolution data in FeSSIF solution, presented similarly as Table 1 and 2 (experiments 41-55). Table 5 provides data from a comparative experiment with similar stable, amorphous hybrid nanoparticles, carried out in FaSSIF and FeSSIF, respectively (experiments 56-57). Table 6 presents further comparative data for experiments carried out in FaSSIF and FeSSIF, respectively.

TABLE 1

Nilotinib - concentration of nilotinib HCl (mg/L) after 5, 30 and 90 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 1 | I | Nilotinib HCl (raw) 100 mg | 100 | — | — | 0.1 | 0.2 | 0.1 |
| 2 | I | Nilotinib HCl (raw) 500 mg | 100 | — | — | 0.2 | 0.2 | 0.2 |
| 3 | I | Nilotinib HCl (raw) 1000 mg | 100 | — | — | 0.2 | 0.3 | 0.2 |
| 4 | I | Nilotinib Base (raw) 500 mg | 100 | — | — | 0.6 | 0.5 | 0.2 |
| 5 | I + P | Nilotinib HCl (raw) 1000 mg | 100 | HPMCP HP55 2000 mg | — | 0.2 | 0.5 | 0.5 |
| 6 | I + P | Nilotinib HCl (raw) 1000 mg | 100 | PVAP 2000 mg | — | 1.3 | 0.2 | 0.4 |
| 7 | I + P | Nilotinib HCl (raw) 1000 mg | 100 | Eudragit L100 2000 mg | — | 0.2 | 0.4 | 0.2 |
| 8 | I + P | Nilotinib HCl (raw) 1000 mg | 100 | Methocel E15 2000 mg | — | 0.1 | 0.1 | 0.1 |
| 9 | I + S | Nilotinib HCl (raw) 1000 mg | 100 | — | Soluplus 357.5 mg | 0.4 | 0.3 | 0.4 |
| 10 | I + S | Nilotinib HCl (raw) 1000 mg | 100 | — | Soluplus 715 mg | 0.4 | 0.5 | 0.5 |
| 11 | I + S | Nilotinib HCl (raw) 1000 mg | 100 | — | Soluplus 1072 mg | 0.4 | 0.5 | 0.6 |
| 12 | I + P + S | Nilotinib HCl (raw) 500 mg | 100 | HPMCP HP55 750 mg | Soluplus 715 mg | 0.4 | 0.6 | 1.0 |
| 13 | I + P + S | Nilotinib HCl (raw) 500 mg | 100 | PVAP 750 mg | Soluplus 715 mg | 0.2 | 0.2 | 0.3 |
| 14 | I + P + S | Nilotinib HCl (raw) 500 mg | 100 | HPMCP HP55 750 mg | TPGS 1000 mg | 0.5 | 0.9 | 1.1 |
| 15 | I + P + S | Nilotinib HCl (raw) 500 mg | 100 | PVAP 750 mg | TPGS 1000 mg | 0.2 | 0.4 | 0.5 |
| 16 | I + P + S | Nilotinib Base (raw) 500 mg | 100 | HPMCP HP55 750 mg | Soluplus 715 mg | 0.2 | 0.5 | 0.4 |
| 17 | I/P | Nilotinib HCl 100 mg | 50 | HPMCP HP55 100 mg | — | 9.5 | 5.6 | 4.5 |
| 18 | I/P | Nilotinib HCl 100 mg | 40 | HPMCP HP55 150 mg | — | 10.4 | 5.0 | 3.7 |
| 19 | I/P | Nilotinib HCl 100 mg | 50 | PVAP 100 mg | — | 7.3 | 5.0 | 4.1 |
| 20 | I/P | Nilotinib HCl 100 mg | 40 | PVAP 150 mg | — | 8.7 | 5.0 | 3.4 |
| 21 | I/P | Nilotinib HCl 100 mg | 50 | Methocel E15 100 mg | — | 1.4 | 1.5 | 1.8 |
| 22 | I/P | Nilotinib HCl 100 mg | 50 | Eudragit L100 100 mg | — | 5.1 | 5.9 | 4.9 |
| 23 | I/P | Nilotinib Base 100 mg | 40 | HPMCP HP55 150 mg | — | 9.7 | 4.7 | 3.8 |
| 24 | I/P + S | Nilotinib HCl 500 mg | 50 | HPMCP HP55 500 mg | Soluplus 715 mg | 53.4 | 46.1 | 35.6 |
| 25 | I/P + S | Nilotinib HCl 500 mg | 50 | HPMCP HP55 500 mg | Soluplus 1430 mg | 85.9 | 87.9 | 80.8 |
| 26 | I/P + S | Nilotinib HCl 500 mg | 50 | HPMCP HP55 500 mg | Soluplus 2145 mg | 117.0 | 127.1 | 116.9 |
| 27 | I/P + S | Nilotinib HCl 500 mg | 50 | HPMCP HP55 500 mg | TPGS 1000 mg | 49.6 | 30.1 | 22.3 |
| 28 | I/P + S | Nilotinib HCl 500 mg | 50 | HPMCP HP55 500 mg | TPGS 2000 mg | 98.4 | 57.4 | 42.6 |
| 29 | I/P + S | Nilotinib HCl 500 mg | 40 | HPMCP HP55 750 mg | Soluplus 357.5 mg | 93.5 | 45.2 | 14.1 |
| 30 | I/P + S | Nilotinib HCl 500 mg | 40 | HPMCP HP55 750 mg | Soluplus 715 mg | 145.0 | 134.3 | 36.8 |
| 31 | I/P + S | Nilotinib HCl 500 mg | 40 | HPMCP HP55 750 mg | TPGS 1000 mg | 93.8 | 31.0 | 22.4 |
| 32 | I/P + S | Nilotinib HCl 500 mg | 40 | PVAP 750 mg | Soluplus 715 mg | 82.9 | 137.9 | 42.9 |
| 33 | I/P + S | Nilotinib HCl 500 mg | 40 | PVAP 750 mg | TPGS 1000 mg | 77.8 | 32.3 | 22.8 |
| 34 | I/P + S | Nilotinib HCl 500 mg | 50 | Methocel E15 500 mg | Soluplus 715 mg | 3.3 | 4.0 | 5.8 |
| 35 | I/P + S | Nilotinib HCl 500 mg | 50 | Methocel E15 500 mg | TPGS 1000 mg | 4.8 | 5.4 | 6.7 |
| 36 | I/P + S | Nilotinib Base 500 mg | 40 | HPMCP HP55 750 mg | Soluplus 715 mg | 178.1 | 120.4 | 33.7 |

TABLE 1-continued

Nilotinib - concentration of nilotinib HCl (mg/L) after 5, 30 and 90 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 37 | I/P/S | Nilotinib HCl 500 mg | 25.4 | HPMCP HP55 750 mg | Soluplus 715 mg | 25.9 | 15.8 | 16.3 |
| 38 | I/P/S | Nilotinib HCl 500 mg | 25.4 | PVAP 750 mg | Soluplus 715 mg | 9.5 | 13.2 | 10.1 |
| 39 | I/P/S | Nilotinib HCl 500 mg | 22.2 | HPMCP HP55 750 mg | TPGS 1000 mg | 16.2 | 13.7 | 3.9 |
| 40 | I/P/S | Nilotinib HCl 500 mg | 22.2 | PVAP 750 mg | TPGS 1000 mg | 13.3 | 12.1 | 9.7 |

TABLE 2

Percentage solubilized nilotinib HCl after 30 minutes dissolution, the Area Under the Curve (AUC - mg/min/L) during 90 minutes dissolution and the AUC increase of compositions comprising stable, amorphous hybrid nanoparticles with nilotinib, compared to nilotinib HCl in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 1 | I | Nilotinib HCl (raw) 100 mg | 100 | — | — | 0.20 | 13.0 | — |
| 2 | I | Nilotinib HCl (raw) 500 mg | 100 | — | — | 0.04 | 23.5 | — |
| 3 | I | Nilotinib HCl (raw) 1000 mg | 100 | — | — | 0.03 | 21.8 | — |
| 4 | I | Nilotinib Base (raw) 500 mg | 100 | — | — | 0.50 | 36.5 | — |
| 5 | I + P | Nilotinib HCl (raw) 1000 mg | 100 | HPMCP HP55 2000 mg | — | 0.05 | 39.3 | 2.0 |
| 6 | I + P | Nilotinib HCl (raw) 1000 mg | 100 | PVAP 2000 mg | — | 0.02 | 40.0 | 2.1 |
| 7 | I + P | Nilotinib HCl (raw) 1000 mg | 100 | Eudragit L100 2000 mg | — | 0.04 | 26.0 | 1.3 |
| 8 | I + P | Nilotinib HCl (raw) 1000 mg | 100 | Methocel E15 2000 mg | — | 0.01 | 8.8 | 0.5 |
| 9 | I + S | Nilotinib HCl (raw) 1000 mg | 100 | — | Soluplus 357.5 mg | 0.03 | 30.8 | 1.6 |
| 10 | I + S | Nilotinib HCl (raw) 1000 mg | 100 | — | Soluplus 715 mg | 0.05 | 42.3 | 2.2 |
| 11 | I + S | Nilotinib HCl (raw) 1000 mg | 100 | — | Soluplus 1072 mg | 0.05 | 45.3 | 2.3 |
| 12 | I + P + S | Nilotinib HCl (raw) 500 mg | 100 | HPMCP HP55 750 mg | Soluplus 715 mg | 0.12 | 61.5 | 3.2 |
| 13 | I + P + S | Nilotinib HCl (raw) 500 mg | 100 | PVAP 750 mg | Soluplus 715 mg | 0.04 | 20.5 | 1.1 |
| 14 | I + P + S | Nilotinib HCl (raw) 500 mg | 100 | HPMCP HP55 750 mg | TPGS 1000 mg | 0.18 | 78.8 | 4.1 |
| 15 | I + P + S | Nilotinib HCl (raw) 500 mg | 100 | PVAP 750 mg | TPGS 1000 mg | 0.08 | 35.0 | 1.8 |
| 16 | I + P + S | Nilotinib Base (raw) 500 mg | 100 | HPMCP HP55 750 mg | Soluplus 715 mg | 0.10 | 36.3 | 1.9 |
| 17 | I/P | Nilotinib HCl 100 mg | 50 | HPMCP HP55 100 mg | — | 5.6 | 515.5 | 26.6 |
| 18 | I/P | Nilotinib HCl 100 mg | 40 | HPMCP HP55 150 mg | — | 5.0 | 479.5 | 24.7 |
| 19 | I/P | Nilotinib HCl 100 mg | 50 | PVAP 100 mg | — | 5.0 | 445.0 | 22.9 |
| 20 | I/P | Nilotinib HCl 100 mg | 40 | PVAP 150 mg | — | 5.0 | 445.0 | 22.9 |
| 21 | I/P | Nilotinib HCl 100 mg | 50 | Methocel E15 100 mg | — | 1.5 | 138.8 | 7.2 |
| 22 | I/P | Nilotinib HCl 100 mg | 50 | Eudragit L100 100 mg | — | 5.9 | 474.3 | 24.2 |
| 23 | I/P | Nilotinib Base 100 mg | 40 | HPMCP HP55 150 mg | — | 4.7 | 459.3 | 23.7 |

TABLE 2-continued

Percentage solubilized nilotinib HCl after 30 minutes dissolution, the Area Under the Curve (AUC - mg/min/L) during 90 minutes dissolution and the AUC increase of compositions comprising stable, amorphous hybrid nanoparticles with nilotinib, compared to nilotinib HCl in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 24 | I/P + S | Nilotinib HCl 500 mg | 50 | HPMCP HP55 500 mg | Soluplus 715 mg | 9.2 | 3828.3 | 197.3 |
| 25 | I/P + S | Nilotinib HCl 500 mg | 50 | HPMCP HP55 500 mg | Soluplus 1430 mg | 17.6 | 7448.3 | 383.9 |
| 26 | I/P + S | Nilotinib HCl 500 mg | 50 | HPMCP HP55 500 mg | Soluplus 2145 mg | 25.4 | 10663.8 | 549.7 |
| 27 | I/P + S | Nilotinib HCl 500 mg | 50 | HPMCP HP55 500 mg | TPGS 1000 mg | 6.0 | 2692.3 | 138.8 |
| 28 | I/P + S | Nilotinib HCl 500 mg | 50 | HPMCP HP55 500 mg | TPGS 2000 mg | 11.5 | 5193.5 | 267.7 |
| 29 | I/P + S | Nilotinib HCl 500 mg | 40 | HPMCP HP55 750 mg | Soluplus 357.5 mg | 9.0 | 3746.5 | 193.1 |
| 30 | I/P + S | Nilotinib HCl 500 mg | 40 | HPMCP HP55 750 mg | Soluplus 715 mg | 26.9 | 8974.8 | 462.6 |
| 31 | I/P + S | Nilotinib HCl 500 mg | 40 | HPMCP HP55 750 mg | TPGS 1000 mg | 6.2 | 3396.5 | 175.1 |
| 32 | I/P + S | Nilotinib HCl 500 mg | 40 | PVAP 750 mg | Soluplus 715 mg | 27.6 | 8391.3 | 432.5 |
| 33 | I/P + S | Nilotinib HCl 500 mg | 40 | PVAP 750 mg | TPGS 1000 mg | 6.5 | 3223.8 | 166.2 |
| 34 | I/P + S | Nilotinib HCl 500 mg | 50 | Methocel E15 500 mg | Soluplus 715 mg | 0.8 | 393.5 | 20.3 |
| 35 | I/P + S | Nilotinib HCl 500 mg | 50 | Methocel E15 500 mg | TPGS 1000 mg | 1.1 | 505.5 | 25.9 |
| 36 | I/P + S | Nilotinib Base 500 mg | 40 | HPMCP HP55 750 mg | Soluplus 715 mg | 24.1 | 8799.5 | 453.6 |
| 37 | I/P/S | Nilotinib HCl 500 mg | 25.4 | HPMCP HP55 750 mg | Soluplus 715 mg | 3.2 | 1549.0 | 79.8 |
| 38 | I/P/S | Nilotinib HCl 500 mg | 25.4 | PVAP 750 mg | Soluplus 715 mg | 2.6 | 1006.5 | 51.9 |
| 39 | I/P/S | Nilotinib HCl 500 mg | 22.2 | HPMCP HP55 750 mg | TPGS 1000 mg | 2.7 | 942.3 | 48.6 |
| 40 | I/P/S | Nilotinib HCl 500 mg | 22.2 | PVAP 750 mg | TPGS 1000 mg | 2.4 | 1004.8 | 51.8 |

TABLE 3

Nilotinib - concentration of nilotinib HCl (mg/L) after 5, 30 and 90 minutes dissolution in FeSSIF solution (pH 5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 41 | I | Nilotinib HCl (raw) 500 mg | 100 | — | — | 0.6 | 0.9 | 0.9 |
| 42 | I + P + S | Nilotinib HCl (raw) 500 mg | 100 | HPMCP HP55 750 mg | Soluplus 715 mg | 0.4 | 0.6 | 1.0 |
| 43 | I + P + S | Nilotinib HCl (raw) 500 mg | 100 | HPMCP HP55 750 mg | Soluplus 1000 mg | 0.2 | 0.2 | 0.3 |
| 44 | I + P + S | Nilotinib HCl (raw) 500 mg | 100 | PVAP 750 mg | Soluplus 715 mg | 0.5 | 0.9 | 1.1 |
| 45 | I + P + S | Nilotinib HCl (raw) 500 mg | 100 | PVAP 750 mg | TPGS 1000 mg | 0.2 | 0.4 | 0.5 |
| 46 | I/P | Nilotinib HCl 500 mg | 40 | HPMCP HP55 750 mg | — | 16.2 | 45.6 | 63.3 |
| 47 | I/P | Nilotinib HCl 500 mg | 40 | PVAP 150 mg | — | 3 | 7.7 | 11.2 |
| 48 | I/P + S | Nilotinib HCl 500 mg | 40 | HPMCP HP55 750 mg | Soluplus 715 mg | 47.7 | 85.5 | 109.4 |
| 49 | I/P + S | Nilotinib HCl 500 mg | 40 | HPMCP HP55 750 mg | TPGS 1000 mg | 74.8 | 112.4 | 125.5 |
| 50 | I/P + S | Nilotinib HCl 500 mg | 40 | PVAP 750 mg | Soluplus 715 mg | 12.9 | 21.3 | 27.3 |

TABLE 3-continued

Nilotinib - concentration of nilotinib HCl (mg/L) after 5, 30 and 90 minutes dissolution in FeSSIF solution (pH 5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 51 | I/P + S | Nilotinib HCl 500 mg | 40 | PVAP 750 mg | TPGS 1000 mg | 20.5 | 29.8 | 31.8 |
| 52 | I/P/S | Nilotinib HCl 500 mg | 40 | HPMCP HP55 750 mg | Soluplus 715 mg | 42.3 | 81.5 | 108.1 |
| 53 | I/P/S | Nilotinib HCl 500 mg | 40 | HPMCP HP55 750 mg | TPGS 1000 mg | 86.3 | 116.3 | 128.8 |
| 54 | I/P/S | Nilotinib HCl 500 mg | 40 | PVAP 750 mg | Soluplus 715 mg | 6.3 | 18.8 | 28.2 |
| 55 | I/P/S | Nilotinib HCl 500 mg | 40 | PVAP 750 mg | TPGS 1000 mg | 20.5 | 29.8 | 31.8 |

TABLE 4

Percentage solubilized nilotinib HCl after 30 minutes dissolution, the Area Under the Curve (AUC - mg/min/L) during 90 minutes dissolution and the AUC increase of compositions comprising stable, amorphous hybrid nanoparticles with nilotinib, compared to nilotinib HCl in raw, crystalline form added to the FeSSIF solution (pH 5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 41 | I | Nilotinib HCl (raw) 500 mg | 100 | — | — | 0.18 | 74.3 | — |
| 42 | I + P + S | Nilotinib HCl (raw) 500 mg | 100 | HPMCP HP55 750 mg | Soluplus 715 mg | 0.12 | 61.5 | 0.8 |
| 43 | I + P + S | Nilotinib HCl (raw) 500 mg | 100 | HPMCP HP55 750 mg | Soluplus 1000 mg | 0.04 | 20.5 | 0.3 |
| 44 | I + P + S | Nilotinib HCl (raw) 500 mg | 100 | PVAP 750 mg | Soluplus 715 mg | 0.18 | 78.8 | 1.1 |
| 45 | I + P + S | Nilotinib HCl (raw) 500 mg | 100 | PVAP 750 mg | TPGS 1000 mg | 0.08 | 35.0 | 0.5 |
| 46 | I/P | Nilotinib HCl 500 mg | 40 | HPMCP HP55 750 mg | — | 9.1 | 4080.0 | 54.9 |
| 47 | I/P | Nilotinib HCl 500 mg | 40 | PVAP 150 mg | — | 7.7 | 708.3 | 9.5 |
| 48 | I/P + S | Nilotinib HCl 500 mg | 40 | HPMCP HP55 750 mg | Soluplus 715 mg | 17.1 | 7631.3 | 102.8 |
| 49 | I/P + S | Nilotinib HCl 500 mg | 40 | HPMCP HP55 750 mg | TPGS 1000 mg | 22.5 | 9664.0 | 130.2 |
| 50 | I/P + S | Nilotinib HCl 500 mg | 40 | PVAP 750 mg | Soluplus 715 mg | 4.3 | 1917.8 | 25.8 |
| 51 | I/P + S | Nilotinib HCl 500 mg | 40 | PVAP 750 mg | TPGS 1000 mg | 6.0 | 2528.0 | 34.0 |
| 52 | I/P/S | Nilotinib HCl 500 mg | 40 | HPMCP HP55 750 mg | Soluplus 715 mg | 16.3 | 7341.3 | 98.9 |
| 53 | I/P/S | Nilotinib HCl 500 mg | 40 | HPMCP HP55 750 mg | TPGS 1000 mg | 23.3 | 10101.3 | 136.0 |
| 54 | I/P/S | Nilotinib HCl 500 mg | 40 | PVAP 750 mg | Soluplus 715 mg | 3.8 | 1739.5 | 23.4 |
| 55 | I/P/S | Nilotinib HCl 500 mg | 40 | PVAP 750 mg | TPGS 1000 mg | 6.0 | 2528.0 | 34.0 |

TABLE 5

Nilotinib - concentration of nilotinib HCl (mg/L) after 5, 30, 90 and 150 minutes dissolution in FaSSIF and FeSSIF solution, respectively.

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min | Conc (mg/L) 150 min |
|---|---|---|---|---|---|---|---|---|---|
| 56 FaSSIFF | I/P + S | Nilotinib HCl 75 mg | 40 | HPMCP HP55 112.5 mg | Soluplus 715 mg | 51.2 | 66 | 62.3 | 53.2 |
| 57 FeSSIFF | I/P + S | Nilotinib HCl 75 mg | 40 | HPMCP HP55 112.5 mg | Soluplus 715 mg | 24.8 | 43.1 | 50.7 | 53 |

TABLE 6

Nilotinib - concentration of nilotinib HCl (mg/L) after 5, 30, 90 and 150 minutes dissolution in FaSSIF and FeSSIF solution, respectively presented as comparative data.

| Exp | Comp. | Inhibitor (I) | Drug load ratio (%) | Polymeric stab. matrix. Component (P) | Solubilizer (S) | Compare (%) 5 min | Compare (%) 30 min | Compare (%) 90 min | Compare (%) 150 min |
|---|---|---|---|---|---|---|---|---|---|
| 2 & 41 | I | Nilotinib HCl (raw) 1000 mg | 100 | — | — | 300 | 450 | 225 | — |
| 12 & 42 | I + P + S | Nilotinib HCl (raw) 500 mg | 100 | HPMCP HP55 750 mg | Soluplus 715 mg | 100 | 200 | 250 | — |
| 18 & 46 | I/P | Nilotinib HCl 100/500 mg | 40 | HPMCP HP55 150/750 mg | — | 156 | 912 | 1711 | — |
| 30 & 48 | I/P + S | Nilotinib HCl 500 mg | 40 | HPMCP HP55 750 mg | Soluplus 715 mg | 33 | 64 | 301 | — |
| 56 & 57 | I/P + S | Nilotinib HCl (raw) 75 mg | 40 | HPMCP HP55 112.5 mg | Soluplus 715 mg | 48 | 65 | 81 | 100 |
| 37 & 52 | I/P/S | Nilotinib HCl 500 mg | 40 | HPMCP HP55 750 mg | Soluplus 715 mg | 163 | 516 | 663 | — |

Conclusions Example 1

Experiments 17-23 show that a solubility increase is obtained with compositions comprising stable, amorphous hybrid nanoparticles with nilotinib HCl and a polymeric stabilizing and matrix-forming component. Particular improvements are achieved with the polymeric stabilizing and matrix-forming components hydroxypropyl methylcellulose phthalate (HPMCP HP55) and polyvinyl acetate phthalate (PVAP). These improvements are not obtained when physically mixing nilotinib HCl with a polymeric stabilizing and matrix-forming component. Experiments 24-36 clearly shows that a further solubility increase is obtained with stable, amorphous hybrid nanoparticles with nilotinib HCl and a polymeric stabilizing and matrix-forming component, wherein a separate solubilizer is added. Particular improvements are achieved by the addition of a separate solubilizer such as polyvinyl caprolactam-polyvinyl acetate-polyethylene glycol copolymer (Soluplus) or d-α-tocopherol acid polyethylene glycol 1000 succinate (TPGS). These improvements were not obtained when physically mixing nilotinib HCl, solubilizer and/or polymeric stabilizing and matrix-forming component (I+S or I+P+S). No particular improvements were obtained with stable, amorphous hybrid nanoparticles with nilotinib HCl, a polymeric stabilizing and matrix-forming and a solubilizer (I/P/S).

The results carried out in FaSSIF and FeSSIF, respectively, indicate that the stable, amorphous hybrid nanoparticles of the invention provide a similar increase in solubility. One issue with PKI formulation is the food effect. Several of the PKIs are labeled for administration in fasted state despite the fact that food in most cases increases their bioavailability. Low bioavailability might partly explain the digestive problems that are associated with the PKIs. The similar dissolution rate in FaSSIF and FeSSIF indicates that the stable, amorphous hybrid nanoparticles of the invention (e.g. experiments 56/57) may reduce food effect and patient digestive problems by its solubility improvement that allows reducing dosage. Thus stable, amorphous hybrid nanoparticles of the invention may be given in conjunction with food intake.

Example 2

Compositions with Stable, Amorphous Hybrid Nanoparticles with Erlotinib HCl—Solubility at pH 6.5 and pH 5

A number of experiments were carried out, wherein erlotinib HCl represented the PKI. The experiments were carried out by measuring concentration of PKI (mg/L) after 5, 30 and 90 minutes dissolution in a solution at about pH 6.5, namely FaSSIF (Fasted State Simulated Intestinal Fluid). Further, experiments were carried out in an alternative solution at about pH 5, namely FeSSIF (Fed State Simulated Intestinal Fluid). Samples of the solution were taken at various time intervals and the amount of PKI was measured by the dissolution measurement assay described above.

Representative results in FaSSIF solution are provided below in Table 7 and 8, where Table 7 provides data of concentration of erlotinib HCl (mg/L) after 5, 30 and 90 minutes dissolution, whereas Table 8 provides data of % solubilized erlotinib HCl after 30 minutes dissolution, the Area Under the Curve (AUC—mg/min/L) during 90 minutes dissolution and the AUC increase of stable, amorphous hybrid nanoparticles, compared to erlotinib HCl in raw, crystalline form added to the solution (experiments 58-68). In Tables 9 and 10, there is provided dissolution data in FeSSIF solution, presented similarly as Table 7 and 8 (experiments 69-73). In Table 11, data from a comparative experiment with similar stable, amorphous hybrid nanoparticles, carried out in FaSSIF and FeSSIF, respectively (experiments 74-83). Table 12 presents further comparative data for experiments carried out in FaSSIF and FeSSIF, respectively.

TABLE 7

Erlotinib - concentration of erlotinib HCl (mg/L) after 5, 30 and 90 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 58 | I | Erlotinib HCl (raw) 1000 mg | 100 | — | — | 28.9 | 6.25 | 4.6 |
| 59 | I + P | Erlotinib HCl (raw) 1000 mg | 100 | HPMC-AS 2000 mg | — | 23 | 53.2 | 84 |
| 60 | I + S | Erlotinib HCl (raw) 1000 mg | 100 | — | Soluplus 715 mg | 92.8 | 156.6 | 176 |
| 61 | I + S | Erlotinib HCl (raw) 1000 mg | 100 | — | TPGS 1000 mg | 51.4 | 14.7 | 11.6 |
| 62 | I + P + S | Erlotinib HCl (raw) 1000 mg | 100 | HPMC-AS 1850 mg | Soluplus 715 mg | 96.7 | 256.6 | 361.8 |
| 63 | I + P + S | Erlotinib HCl (raw) 1000 mg | 100 | HPMC-AS 1850 mg | TPGS 1000 mg | 81.3 | 188.1 | 256.6 |
| 64 | I/P | Erlotinib HCl 1000 mg | 35 | HPMC-AS 1850 mg | — | 83.4 | 79.6 | 44.8 |
| 65 | I/P + S | Erlotinib HCl 1000 mg | 35 | HPMC-AS 1850 mg | Soluplus 715 mg | 187.3 | 269.7 | 284 |
| 66 | I/P + S | Erlotinib HCl 1000 mg | 35 | HPMC-AS 1850 mg | TPGS 1000 mg | 155.2 | 210.6 | 225.3 |
| 67 | I/P/S | Erlotinib HCl 1000 mg | 28 | HPMC-AS 1850 mg | Soluplus 715 mg | 90.1 | 95 | 96.4 |
| 68 | I/P/S | Erlotinib HCl 1000 mg | 26 | HPMC-AS 1850 mg | TPGS 1000 mg | 93.7 | 85.4 | 52.8 |

TABLE 8

Percentage solubilized erlotinib HCl after 30 minutes dissolution, the Area Under the Curve (AUC - mg/min/L) during 90 minutes dissolution and the AUC increase with stable, amorphous hybrid nanoparticles, compared to erlotinib in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 58 | I | Erlotinib HCl (raw) 1000 mg | 100 | — | — | 0.6 | 837 | — |
| 59 | I + P | Erlotinib HCl (raw) 1000 mg | 100 | HPMC-AS 2000 mg | — | 5.3 | 5126 | 6.1 |
| 60 | I + S | Erlotinib HCl (raw) 1000 mg | 100 | — | Soluplus 715 mg | 15.7 | 13328 | 15.9 |
| 61 | I + S | Erlotinib HCl (raw) 1000 mg | 100 | — | TPGS 1000 mg | 1.5 | 1744 | 2.1 |
| 62 | I + P + S | Erlotinib HCl (raw) 1000 mg | 100 | HPMC-AS 1850 mg | Soluplus 715 mg | 25.7 | 23210 | 27.7 |

TABLE 8-continued

Percentage solubilized erlotinib HCl after 30 minutes dissolution, the Area Under the Curve (AUC - mg/min/L) during 90 minutes dissolution and the AUC increase with stable, amorphous hybrid nanoparticles, compared to erlotinib in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 63 | I + P + S | Erlotinib HCl (raw) 1000 mg | 100 | HPMC-AS 1850 mg | TPGS 1000 mg | 18.8 | 16912 | 20.2 |
| 64 | I/P | Erlotinib HCl 1000 mg | 35 | HPMC-AS 1850 mg | — | 8.0 | 5978 | 7.1 |
| 65 | I/P + S | Erlotinib HCl 1000 mg | 35 | HPMC-AS 1850 mg | Soluplus 715 mg | 27.0 | 22792 | 27.2 |
| 66 | I/P + S | Erlotinib HCl 1000 mg | 35 | HPMC-AS 1850 mg | TPGS 1000 mg | 21.1 | 18038 | 21.5 |
| 67 | I/P/S | Erlotinib HCl 1000 mg | 28 | HPMC-AS 1850 mg | Soluplus 715 mg | 9.5 | 8281 | 9.9 |
| 68 | I/P/S | Erlotinib HCl 1000 mg | 26 | HPMC-AS 1850 mg | TPGS 1000 mg | 8.5 | 6619 | 7.9 |

TABLE 9

Erlotinib - concentration of erlotinib HCl (mg/L) after 5, 30 and 90 minutes dissolution in FeSSIF solution (pH 5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 69 | I | Erlotinib HCl (raw) 1000 mg | 100 | — | — | 156.8 | 189.9 | 196 |
| 70 | I + P + S | Erlotinib HCl (raw) 1000 mg | 100 | HPMC-AS 1850 mg | Soluplus 715 mg | 25.5 | 75.1 | 126.2 |
| 71 | I/P | Erlotinib HCl 1000 mg | 35 | HPMC-AS 1850 mg | — | 258.2 | 402.1 | 464.5 |
| 72 | I/P + S | Erlotinib HCl 1000 mg | 35 | HPMC-AS 1850 mg | Soluplus 715 mg | 260.1 | 422.8 | 498.8 |
| 73 | I/P/S | Erlotinib HCl 1000 mg | 28 | HPMC-AS 1850 mg | Soluplus 715 mg | 293.6 | 395.2 | 434.9 |

TABLE 10

Percentage solubilized erlotinib HCl after 30 minutes dissolution, the Area Under the Curve (AUC - mg/min/L) during 90 minutes dissolution and the AUC increase with stable, amorphous hybrid nanoparticles, compared to erlotinib in raw, crystalline form added to the FeSSIF solution (pH 5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 69 | I | Erlotinib HCl (raw) 1000 mg | 100 | — | — | 19.0 | 16303 | — |
| 70 | I + P + S | Erlotinib HCl (raw) 1000 mg | 100 | HPMC-AS 1850 mg | Soluplus 715 mg | 7.5 | 7360 | 0.5 |
| 71 | I/P | Erlotinib HCl 1000 mg | 35 | HPMC-AS 1850 mg | — | 40.2 | 34897 | 2.1 |
| 72 | I/P + S | Erlotinib HCl 1000 mg | 35 | HPMC-AS 1850 mg | Soluplus 715 mg | 42.3 | 36835 | 2.3 |
| 73 | I/P/S | Erlotinib HCl 1000 mg | 28 | HPMC-AS 1850 mg | Soluplus 715 mg | 35.5 | 34244 | 2.1 |

TABLE 11

Erlotinib - concentration of erlotinib HCl after 5, 30 and 90 minutes dissolution in FaSSIF and FeSSIF solution, respectively.

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 74 FaSSIF | I + P + S | Erlotinib HCl (raw) 1000 mg | 100 | HPMC-AS 1850 mg | Soluplus 1430 mg | 134.1 | 369.8 | 533.4 |
| 75 FeSSIF | I + P + S | Erlotinib HCl (raw) 1000 mg | 100 | HPMC-AS 1850 mg | Soluplus 1430 mg | 24.4 | 88.8 | 154.4 |
| 76 FaSSIF | I/P + S | Erlotinib HCl 1000 mg | 35 | HPMC-AS 1850 mg | Soluplus 1430 mg | 275.4 | 441.4 | 508 |
| 77 FeSSIF | I/P + S | Erlotinib HCl 1000 mg | 35 | HPMC-AS 1850 mg | Soluplus 1430 mg | 292.2 | 476.2 | 546.5 |
| 78 FaSSIF | I/P/S | Erlotinib HCl 1000 mg | 23 | HPMC-AS 1850 mg | Soluplus 1430 mg | 90.4 | 108 | 114.8 |
| 79 FeSSIF | I/P/S | Erlotinib HCl 1000 mg | 23 | HPMC-AS 1850 mg | Soluplus 1430 mg | 259.3 | 354.8 | 405.5 |
| 80 FaSSIF | I + P + S | Erlotinib HCl (raw) 500 mg | 100 | HPMC-AS 925 mg | Soluplus 715 mg | 78.6 | 216.4 | 304.6 |
| 81 FeSSIF | I + P + S | Erlotinib HCl (raw) 500 mg | 100 | HPMC-AS 925 mg | Soluplus 715 mg | 16.2 | 55.8 | 104.7 |
| 82 FaSSIF | I/P + S | Erlotinib HCl 500 mg | 35 | HPMC-AS 925 mg | Soluplus 715 mg | 171.6 | 284.6 | 334.6 |
| 83 FeSSIF | I/P + S | Erlotinib HCl 500 mg | 35 | HPMC-AS 925 mg | Soluplus 715 mg | 168.3 | 268.7 | 317.9 |

TABLE 12

Erlotinib - concentration of erlotinib HCl (mg/L) after 5, 30 and 90 minutes dissolution in FaSSIF and FeSSIF solution, respectivly presented as comparative data.

| Exp | Comp. | Inhibitor (I) | Drug load ratio (%) | Polymeric stab. matrix. Component (P) | Solubilizer (S) | Compare (%) 5 min | Compare (%) 30 min | Compare (%) 90 min |
|---|---|---|---|---|---|---|---|---|
| 58 & 69 | I | Erlotinib HCl (raw) 1000 mg | 100 | — | — | 543 | 3038 | 4261 |
| 74 & 75 | I + P + S | Erlotinib HCl (raw) 1000 mg | 100 | HPMC-AS 1850 mg | Soluplus 1430 mg | 18 | 24 | 29 |
| 80 & 81 | I + P + S | Erlotinib HCl (raw) 500 mg | 100 | HPMC-AS 925 mg | Soluplus 715 mg | 21 | 26 | 34 |
| 64 & 71 | I/P | Erlotinib HCl 1000 mg | 35 | HPMC-AS 1850 mg | — | 310 | 505 | 1037 |
| 76 & 77 | I/P + S | Erlotinib HCl 1000 mg | 35 | HPMC-AS 1850 mg | Soluplus 1430 mg | 106 | 108 | 108 |
| 82 & 83 | I/P + S | Erlotinib HCl 500 mg | 35 | HPMC-AS 925 mg | Soluplus 715 mg | 98 | 94 | 95 |
| 78 & 79 | I/P/S | Erlotinib HCl 1000 mg | 23 | HPMC-AS 1850 mg | Soluplus 1430 mg | 287 | 329 | 353 |

Conclusions Example 2

The experiments show that a solubility increase is obtained with compositions comprising stable, amorphous hybrid nanoparticles with erlotinib HCl and a polymeric stabilizing and matrix-forming component. Particular improvements are achieved with the polymeric stabilizing and matrix-forming component hydroxypropyl methylcellulose acetate succinate (HPMC-AS). Experiments 65-66 and 72 show that a further solubility increase is obtained with stable, amorphous hybrid nanoparticles with erlotinib HCl and a polymeric stabilizing and matrix-forming component, wherein a separate solubilizer is added. Particular improvements are achieved by the addition of a separate solubilizer added, wherein said solubilizer is selected from polyvinyl caprolactam-polyvinyl acetate-polyethylene glycol copolymer (Soluplus) and d-α-tocopherol acid polyethylene glycol 1000 succinate (TPGS). This improvement was not observed when the solubilizer was incorporated into the stable, amorphous hybrid nanoparticles.

Physical mixes of erlotinib HCl with a solubilizer and/or HPMC AS improve also the solubility in FaSSIF (experiments 59, 60-61, 62-63) but not in FeSSIF (experiment 69-72). One issue with PKI formulation is the food effect. Several of the PKIs are labeled for administration in fasted state despite the fact that food in most cases increases their bioavailability. Low bioavailability might partly explain the digestive problems that are associated with the PKIs. The data indicates that the stable, amorphous hybrid nanoparticles may reduce food effect and patient digestive problems by its equal solubility improvement in both FaSSIF and FeSSIF (experiment 76/77 and 82/83) that moreover potentially may allow reducing of dosage. Thus, compositions comprising these stable, amorphous hybrid nanoparticles may be given in conjunction with food intake.

Example 3

Compositions with Stable, Amorphous Hybrid Nanoparticles with Pazopanib—Solubility at pH 6.5 and pH 5

A number of experiments were carried out, wherein pazopanib represented the PKI. The experiments were carried out by measuring concentration of PKI (mg/L) after 5, 30 and 90 minutes dissolution in a solution at about pH 6.5, namely FaSSIF (Fasted State Simulated Intestinal Fluid). Further, experiments were carried out in an alternative solution at about pH 5, namely FeSSIF (Fed State Simulated Intestinal Fluid). Samples of the solution were taken at various time intervals and the amount of PKI was measured by the dissolution measurement assay described above.

Representative results in FaSSIF solution are provided below in Table 13 and 14, where Table 13 provides data of concentration of pazopanib (mg/L) after 5, 30 and 90 minutes dissolution, whereas Table 14 provides data of % solubilized pazopanib after 30 minutes dissolution, the Area Under the Curve (AUC—mg/min/L) during 90 minutes dissolution and the AUC increase with stable, amorphous hybrid nanoparticles, compared to pazopanib in raw, crystalline form added to the solution (experiments 84-93). In Tables 15 and 16, there is provided dissolution data in FeSSIF solution, presented similarly as Table 13 and 14 (experiments 94-101). In Table 17, data from a comparative experiment with similar stable, amorphous hybrid nanoparticles, carried out in FaSSIF and FeSSIF, respectively (experiments 102-109). Table 18 presents further comparative data for experiments carried out in FaSSIF and FeSSIF, respectively, with stable, amorphous hybrid nanoparticles.

TABLE 13

Pazopanib - concentration of pazopanib (mg/L) after 5, 30 and 90 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 84 | I | Pazopanib (raw) 1000 mg | 100 | — | — | 46.2 | 24.4 | 15.0 |
| 85 | I + P | Pazopanib (raw) 1000 mg | 100 | PVP 90K 2000 mg | — | 82.7 | 83.8 | 67.7 |
| 86 | I + S | Pazopanib (raw) 1000 mg | 100 | — | Soluplus 357 mg | 116.3 | 177.7 | 204.3 |
| 87 | I + S | Pazopanib (raw) 1000 mg | 100 | — | Soluplus 715 mg | 177.6 | 270.8 | 324.2 |
| 88 | I + P + S | Pazopanib (raw) 1000 mg | 100 | PVP 90K 1857 mg | Soluplus 715 mg | 198.8 | 312.2 | 394.1 |
| 89 | I + P + S | Pazopanib (raw) 1000 mg | 100 | PVP 90K 1857 mg | TPGS 1000 mg | 182.6 | 196.7 | 49.2 |
| 90 | I/P | Pazopanib 1000 mg | 35 | PVP 90K 1857 mg | — | 89.4 | 103.4 | 92.8 |
| 91 | I/P + S | Pazopanib 1000 mg | 35 | PVP 90K 1857 mg | Soluplus 715 mg | 238.9 | 409.4 | 469.3 |
| 92 | I/P + S | Pazopanib 1000 mg | 35 | PVP 90K 1857 mg | TPGS 1000 mg | 207.5 | 244.8 | 76.3 |
| 93 | I/P/S | Pazopanib 1000 mg | 28 | PVP 90K 1857 mg | Soluplus 715 mg | 127.2 | 128.3 | 82.0 |

TABLE 14

Percentage solubilized pazopanib after 30 minutes dissolution, the Area Under the Curve (AUC - mg/min/L) during 90 minutes dissolution and the AUC increase with stable, amorphous hybrid nanoparticles, compared to pazopanib in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 84 | I | Pazopanib (raw) 1000 mg | 100 | — | — | 2.4 | 2180 | — |
| 85 | I + P | Pazopanib (raw) 1000 mg | 100 | PVP 90K 2000 mg | — | 8.4 | 6833 | 3.1 |
| 86 | I + S | Pazopanib (raw) 1000 mg | 100 | — | Soluplus 357 mg | 17.8 | 15426 | 7.1 |
| 87 | I + S | Pazopanib (raw) 1000 mg | 100 | — | Soluplus 715 mg | 27.1 | 23899 | 11.0 |

TABLE 14-continued

Percentage solubilized pazopanib after 30 minutes dissolution, the Area Under the Curve (AUC - mg/min/L) during 90 minutes dissolution and the AUC increase with stable, amorphous hybrid nanoparticles, compared to pazopanib in raw, crystalline form added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 88 | I + P + S | Pazopanib (raw) 1000 mg | 100 | PVP 90K 1857 mg | Soluplus 715 mg | 31.2 | 28074 | 12.9 |
| 89 | I + P + S | Pazopanib (raw) 1000 mg | 100 | PVP 90K 1857 mg | TPGS 1000 mg | 19.7 | 12575 | 5.8 |
| 90 | I/P | Pazopanib 1000 mg | 35 | PVP 90K 1857 mg | — | 10.3 | 8520 | 3.9 |
| 91 | I/P + S | Pazopanib 1000 mg | 35 | PVP 90K 1857 mg | Soluplus 715 mg | 40.9 | 35062 | 16.1 |
| 92 | I/P + S | Pazopanib 1000 mg | 35 | PVP 90K 1857 mg | TPGS 1000 mg | 24.5 | 15806 | 7.3 |
| 93 | I/P/S | Pazopanib 1000 mg | 28 | PVP 90K 1857 mg | Soluplus 715 mg | 12.8 | 9821 | 4.5 |

TABLE 15

Pazopanib - concentration of pazopanib (mg/L) after 5, 30 and 90 minutes dissolution in FeSSIF solution (pH 5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 94 | I | Pazopanib (raw) 1000 mg | 100 | — | — | 231.3 | 321.4 | 239.3 |
| 95 | I + P | Pazopanib (raw) 1000 mg | 100 | PVP 90K 2000 mg | — | 234.8 | 309.7 | 269.7 |
| 96 | I + S | Pazopanib (raw) 1000 mg | 100 | — | Soluplus 357 mg | 209.3 | 309.6 | 229.1 |
| 97 | I + P + S | Pazopanib (raw) 1000 mg | 100 | PVP 90K 1857 mg | Soluplus 715 mg | 307.5 | 475.3 | 578.0 |
| 98 | I + P + S | Pazopanib (raw) 1000 mg | 100 | PVP 90K 1857 mg | TPGS 1000 mg | 320.9 | 395.1 | 325.6 |
| 99 | I/P | Pazopanib 1000 mg | 35 | PVP 90K 1857 mg | — | 348.4 | 362.1 | 335.8 |
| 100 | I/P + S | Pazopanib 1000 mg | 35 | PVP 90K 1857 mg | Soluplus 715 mg | 450.0 | 684.4 | 777.6 |
| 101 | I/P/S | Pazopanib 1000 mg | 28 | PVP 90K 1857 mg | Soluplus 715 mg | 226.1 | 347.3 | 361.0 |

TABLE 16

Percentage solubilized pazopanib after 30 minutes dissolution, the Area Under the Curve (AUC - mg/min/L) during 90 minutes dissolution and the AUC increase with stable, amorphous hybrid nanoparticles, compared to pazopanib in raw, crystalline form added to the FeSSIF solution (pH 5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 94 | I | Pazopanib (raw) 1000 mg | 100 | — | — | 32.1 | 24308 | — |
| 95 | I + P | Pazopanib (raw) 1000 mg | 100 | PVP 90K 2000 mg | — | 31.0 | 24775 | 1.0 |
| 96 | I + S | Pazopanib (raw) 1000 mg | 100 | — | Soluplus 357 mg | 31.0 | 23171 | 1.0 |
| 97 | I + P + S | Pazopanib (raw) 1000 mg | 100 | PVP 90K 1857 mg | Soluplus 715 mg | 47.5 | 42153 | 1.7 |
| 98 | I + P + S | Pazopanib (raw) 1000 mg | 100 | PVP 90K 1857 mg | TPGS 1000 mg | 39.5 | 31373 | 1.3 |
| 99 | I/P | Pazopanib 1000 mg | 35 | PVP 90K 1857 mg | — | 36.2 | 30689 | 1.3 |

TABLE 16-continued

Percentage solubilized pazopanib after 30 minutes dissolution, the Area Under the Curve (AUC - mg/min/L) during 90 minutes dissolution and the AUC increase with stable, amorphous hybrid nanoparticles, compared to pazopanib in raw, crystalline form added to the FeSSIF solution (pH 5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 100 | I/P + S | Pazopanib 1000 mg | 35 | PVP 90K 1857 mg | Soluplus 715 mg | 68.4 | 59165 | 2.4 |
| 101 | I/P/S | Pazopanib 1000 mg | 28 | PVP 90K 1857 mg | Soluplus 715 mg | 34.7 | 28982 | 1.2 |

TABLE 17

Pazopanib - concentration of pazopanib after 5, 30 and 90 minutes dissolution in FaSSIF and FeSSIF solution, respectively.

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 102 FaSSIF | I + P + S | Pazopanib (raw) 300 mg | 100 | PVP 90K 557 mg | Soluplus 428 mg | 76.8 | 113.8 | 139.6 |
| 103 FeSSIF | I + P + S | Pazopanib (raw) 300 mg | 100 | PVP 90K 557 mg | Soluplus 428 mg | 116.7 | 193.6 | 246.9 |
| 104 FaSSIF | I/P + S | Pazopanib 300 mg | 35 | PVP 90K 557 mg | Soluplus 428 mg | 154.7 | 214.7 | 223 |
| 105 FeSSIF | I/P + S | Pazopanib 300 mg | 35 | PVP 90K 557 mg | Soluplus 428 mg | 186 | 273.3 | 303.1 |
| 106 FaSSIF | I + P + S | Pazopanib (raw) 1000 mg | 100 | PVP 90K 1857 mg | Soluplus 1428 mg | 261.1 | 421.6 | 508.5 |
| 107 FeSSIF | I + P + S | Pazopanib (raw) 1000 mg | 100 | PVP 90K 1857 mg | Soluplus 1428 mg | 275.8 | 495.4 | 588.0 |
| 108 FeSSIF | I/P + S | Pazopanib 1000 mg | 35 | PVP 90K 1857 mg | Soluplus 1428 mg | 508.9 | 705.8 | 758.4 |
| 109 FeSSIF | I/P + S | Pazopanib 1000 mg | 35 | PVP 90K 1857 mg | Soluplus 1428 mg | 469.1 | 715.2 | 747.4 |

TABLE 18

Pazopanib - concentration of pazopanib (mg/L) after 5, 30 and 90 minutes dissolution in FaSSIF and FeSSIF solution, respectively presented as comparative data.

| Exp | Comp. | Inhibitor (I) | Drug load ratio (%) | Polymeric stab. matrix. Component (P) | Solubilizer (S) | Compare (%) 5 min | Compare (%) 30 min | Compare (%) 90 min |
|---|---|---|---|---|---|---|---|---|
| 84 & 94 | I | Pazopanib (raw) 1000 mg | 100 | — | — | 501 | 1317 | 1595 |
| 85 & 95 | I + P | Pazopanib (raw) 1000 mg | 100 | PVP 90K 1857 mg | — | 284 | 370 | 398 |
| 87 & 96 | I + S | Pazopanib (raw) 1000 mg | 100 | — | Soluplus 715 mg | 118 | 114 | 71 |
| 88 & 97 | I + P + S | Pazopanib (raw) 1000 mg | 100 | PVP 90K 1857 mg | Soluplus 715 mg | 155 | 152 | 147 |
| 102 & 103 | I + P + S | Pazopanib (raw) 300 mg | 100 | PVP 90K 557 mg | Soluplus 428 mg | 152 | 170 | 177 |
| 90 & 99 | I/P | Pazopanib 1000 mg | 35 | PVP 90K 1857 mg | — | 390 | 350 | 362 |
| 89 & 100 | I/P + S | Pazopanib 1000 mg | 35 | PVP 90K 1857 mg | Soluplus 715 mg | 188 | 167 | 166 |
| 104 & 105 | I/P + S | Pazopanib 300 mg | 35 | PVP 90K 557 mg | Soluplus 428 mg | 120 | 127 | 136 |
| 93 & 101 | I/P/S | Pazopanib 1000 mg | 28 | PVP 90K 1857 mg | Soluplus 715 mg | 178 | 271 | 440 |

Conclusions Example 3

The experiments show that a solubility increase is obtained with compositions comprising stable, amorphous hybrid nanoparticles with pazopanib and a polymeric stabilizing and matrix-forming component. Particular improvements are achieved with the polymeric stabilizing and matrix-forming component polyvinylpyrrolidone K-90 (PVP 90K). Experiments 91-92 show that a further solubility increase is obtained with stable, amorphous hybrid nanoparticles with pazopanib and a polymeric stabilizing and matrix-forming component, wherein a separate solubilizer is added. Particular improvements are achieved by the addition of a separate solubilizer added, wherein said solubilizer is selected from polyvinyl caprolactam-polyvinyl acetate-polyethylene glycol copolymer (Soluplus) and d-α-tocopherol acid polyethylene glycol 1000 succinate (TPGS). This improvement was not observed when the solubilizer was incorporated into the stable, amorphous hybrid nanoparticles of the invention.

The results carried out in FaSSIF and FeSSIF, respectively, indicates that the stable, amorphous hybrid nanoparticles of the invention provide a similar increase in solubility. One issue with PKI formulation is the food effect. Several of the PKIs are labeled for administration in fasted state despite the fact that food in most cases increases their bioavailability. Low bioavailability might partly explain the digestive problems that are associated with the PKIs. The similar dissolution rate in FaSSIF and FeSSIF indicates that the stable, amorphous hybrid nanoparticles may reduce food effect and patient digestive problems by its equal solubility improvement in both FaSSIF and FeSSIF (experiments 89/100 and 104/105) that moreover allows reducing dosage. Thus stable, amorphous hybrid nanoparticles of the invention may be given in conjunction with food intake.

Example 4

Compositions with Stable, Amorphous Hybrid Nanoparticles with Lapatinib—Solubility at pH 6.5

A number of experiments were carried out, wherein lapatinib base or lapatinib ditosylate salt represented the PKI. The experiments were carried out by measuring concentration of PKI (mg/L) after 5, 30 and 90 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 19 and 20, where Table 19 provides data of concentration of lapatinib (mg/L) after 5, 30 and 90 minutes dissolution, whereas Table 20 provides data of % solubilized lapatinib after 30 minutes dissolution, the Area Under the Curve (AUC—mg/min/L) during 90 minutes dissolution and the AUC increase with stable, amorphous hybrid nanoparticles of the invention, compared to non-formulated lapatinib ditosylate salt added to the solution (experiments 110-126).

TABLE 19

Lapatinib - concentration of lapatinib (mg/L) after 5, 30 and 90 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 5 min | Conc (mg/L) 30 min | Conc (mg/L) 90 min |
|---|---|---|---|---|---|---|---|---|
| 110 | I | Lapatinib (base) 2000 mg | 100 | — | — | 2.9 | 6.0 | 6.5 |
| 111 | I | Lapatinib (salt) 2000 mg | 100 | — | — | 57.7 | 132.2 | 124.2 |
| 112 | I + S | Lapatinib (salt) 2000 mg | 100 | — | Soluplus 285 mg | 67.6 | 142.9 | 140.0 |
| 113 | I + S | Lapatinib (salt) 2000 mg | 100 | — | Soluplus 645 mg | 144.7 | 283.6 | 204.0 |
| 114 | I + P | Lapatinib (base) 2000 mg | 100 | HPC LF 4000 mg | — | 1.9 | 4.9 | 6.1 |
| 115 | I + P | Lapatinib (salt) 2000 mg | 100 | HPC LF 4000 mg | — | 56.7 | 93.8 | 81.8 |
| 116 | I + P + S | Lapatinib (base) 660 mg | 100 | HPC LF 340 mg | Soluplus 715 mg | 5.5 | 22.5 | 52.0 |
| 117 | I + P + S | Lapatinib (salt) 660 mg | 100 | HPC LF 340 mg | Soluplus 715 mg | 71.7 | 182.5 | 240.4 |
| 118 | I + P + S | Lapatinib (base) 660 mg | 100 | HPC LF 340 mg | TPGS 1000 mg | 11.8 | 40.6 | 82.9 |
| 119 | I + P + S | Lapatinib (salt) 660 mg | 100 | HPC LF 340 mg | TPGS 1000 mg | 65.1 | 176.7 | 175.3 |
| 120 | I/P | Lapatinib (base) 660 mg | 66 | HPC EF 340 mg | — | 162.5 | 184.0 | 157.1 |
| 121 | I/P | Lapatinib (base) 660 mg | 66 | HPC LF 340 mg | — | 190.9 | 193.5 | 48.0 |
| 122 | I/P + S | Lapatinib (base) 660 mg | 66 | HPC EF 340 mg | Soluplus 715 mg | 220.4 | 259.6 | 280.0 |
| 123 | I/P + S | Lapatinib (base) 660 mg | 66 | HPC LF 340 mg | Soluplus 715 mg | 200.7 | 315.6 | 327.6 |
| 124 | I/P + S | Lapatinib (base) 660 mg | 66 | HPC EF 340 mg | TPGS 500 mg | 202.2 | 237.5 | 242.5 |
| 125 | I/P + S | Lapatinib (base) 660 mg | 66 | HPC LF 340 mg | TPGS 500 mg | 288.4 | 327.3 | 301.5 |
| 126 | I/P/S | Lapatinib (base) 660 mg | 66 | HPC LF 340 mg | Soluplus 715 mg | 57.6 | 107.2 | 126.3 |

TABLE 20

Percentage solubilized lapatinib after 30 minutes dissolution, the Area Under the Curve (AUC - mg/min/L) during 90 minutes dissolution and the AUC increase with stable, amorphous hybrid nanoparticles of the invention, compared to non-formulated lapatinib ditosylate salt added to the FaSSIF solution (pH 6.5).

| Exp | Comp. | Inhibitor (I) | Drug load ratio (%) | Polymeric stab. matrix. Component (P) | Solubilizer (S) | % solubilized 30 min. | AUC/ 90 min Mg/min/L | AUC increase |
|---|---|---|---|---|---|---|---|---|
| 110 | I | Lapatinib (base) 2000 mg | 100 | — | — | 0.3 | 494 | — |
| 111 | I | Lapatinib (salt) 2000 mg | 100 | — | — | 6.6 | 10210 | — |
| 112 | I + S | Lapatinib (salt) 2000 mg | 100 | — | Soluplus 285 mg | 7.1 | 11287 | 1.1 |
| 113 | I + S | Lapatinib (salt) 2000 mg | 100 | — | Soluplus 645 mg | 14.2 | 20344 | 2.0 |
| 114 | I + P | Lapatinib (base) 2000 mg | 100 | HPC LF 4000 mg | — | 0.2 | 420 | 0.04 |
| 115 | I + P | Lapatinib (salt) 2000 mg | 100 | HPC LF 4000 mg | — | 4.7 | 7291 | 0.7 |
| 116 | I + P + S | Lapatinib (base) 660 mg | 100 | HPC LF 340 mg | Soluplus 715 mg | 3.4 | 2599 | 0.3 |
| 117 | I + P + S | Lapatinib (salt) 660 mg | 100 | HPC LF 340 mg | Soluplus 715 mg | 27.7 | 16044 | 1.6 |
| 118 | I + P + S | Lapatinib (base) 660 mg | 100 | HPC LF 340 mg | TPGS 1000 mg | 6.2 | 4390 | 0.4 |
| 119 | I + P + S | Lapatinib (salt) 660 mg | 100 | HPC LF 340 mg | TPGS 1000 mg | 26.8 | 13745 | 1.3 |
| 120 | I/P | Lapatinib (base) 660 mg | 66 | HPC EF 340 mg | — | 27.9 | 14971 | 1.5 |
| 121 | I/P | Lapatinib (base) 660 mg | 66 | HPC LF 340 mg | — | 29.3 | 12527 | 1.2 |
| 122 | I/P + S | Lapatinib (base) 660 mg | 66 | HPC EF 340 mg | Soluplus 715 mg | 39.3 | 22739 | 2.2 |
| 123 | I/P + S | Lapatinib (base) 660 mg | 66 | HPC LF 340 mg | Soluplus 715 mg | 47.8 | 26252 | 2.6 |
| 124 | I/P + S | Lapatinib (base) 660 mg | 66 | HPC EF 340 mg | TPGS 500 mg | 36.0 | 20402 | 2.0 |
| 125 | I/P + S | Lapatinib (base) 660 mg | 66 | HPC LF 340 mg | TPGS 500 mg | 49.6 | 27281 | 2.7 |
| 126 | I/P/S | Lapatinib (base) 660 mg | 66 | HPC LF 340 mg | Soluplus 715 mg | 16.2 | 9209 | 0.9 |

Conclusions Example 4

The experiments 122-125 clearly shows that a solubility increase is obtained with stable, amorphous hybrid nanoparticles of the invention, with lapatinib, in particular lapatinib base and a polymeric stabilizing and matrix-forming component, wherein a separate solubilizer is added to the composition. Particular improvements are achieved with the polymeric stabilizing and matrix-forming component hydroxypropyl cellulose EF and hydroxypropyl cellulose LF. Further, improvements are achieved by the addition of a separate solubilizer added, wherein said solubilizer is selected from polyvinyl caprolactam-polyvinyl acetate-polyethylene glycol copolymer (Soluplus) and d-α-tocopherol acid polyethylene glycol 1000 succinate (TPGS).

Example 5

Compositions with Stable, Amorphous Hybrid Nanoparticles with Nilotinib HCl—Solubility at pH 1.4

A number of experiments were carried out, wherein nilotinib HCl represented the PKI. The experiments were carried out by measuring concentration of PKI (mg/L) after 5, 30 and 90 minutes dissolution in a solution at about pH 1.4, namely SGF (Simulated Gastric Fluid). Samples of the solution were taken at various time intervals and the amount of PKI was measured by the dissolution measurement assay described above.

Representative results in SGF solution are provided below in Table 21, which provides percentage of solubilized nilotinib HCl from both a physical mix with nilotinib HCl in raw, crystalline form and stable, amorphous hybrid nanoparticles of the invention after 5, 30 and 90 minutes dissolution. Nilotinib present in the physical mix of nilotinib HCl raw with the polymeric stabilizing and matrix-forming component PVAP and the solubilizer Soluplus (Exp. 129) is dissolved completely within 5 minutes in SGF while nilotinib is only partially dissolved after 90 min in SGF with stable, amorphous hybrid nanoparticles of the invention, wherein the components are comprised as stable, amorphous hybrid nanoparticles, with the addition of a solubilizer (Exp. 128) or without the addition of a solubilizer (Exp. 127).

TABLE 21

Nilotinib HCl - concentration of nilotinib HCl (mg/L) after 5, 30 and 90 minutes dissolution in SGF solution (pH 1.4).

| Exp | Comp. | Inhibitor (I) | Drug load ratio (%) | Polymeric stab. matrix. Component (P) | Solubilizer (S) | % solubilized 5 min | % solubilized 30 min | % solubilized 90 min |
|---|---|---|---|---|---|---|---|---|
| 127 | I/P | Nilotinib HCl 500 mg | 100 | PVAP 750 mg | — | 32 | 40 | 42 |
| 128 | I/P + S | Nilotinib HCl 500 mg | 100 | PVAP 750 mg | Soluplus 715 mg | 38 | 48 | 50 |
| 128 | I + P + S | Nilotinib HCl (raw) 1000 mg | 100 | PVAP 750 mg | Soluplus 715 mg | 100 | 100 | 100 |

Conclusions Example 5

The experiments 127-129 shows that a nilotinib HCl, in stable, amorphous hybrid nanoparticles of the invention (exp 127 and 128) are partially solubilized at pH 1.4. The stable, amorphous hybrid nanoparticles with a polymeric stabilizing and matrix-forming component such as PVAP is partially protected from the acidic environment.

Example 6

Compositions with Stable, Amorphous Hybrid Nanoparticles with Gefitinib—Solubility at pH 6.5

A number of experiments were carried out, wherein gefitinib represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 22 and 23, where Table 22 provides data of concentration of gefitinib (mg/L) after 3, 40 and 80 minutes dissolution, whereas Table 23 provides data of % solubilized gefitinib after 40 minutes dissolution, the Area Under the Curve (AUC—mg/min/L) during 80 minutes dissolution and the AUC increase with stable, amorphous hybrid nanoparticles of the invention, compared to non-formulated gefitinib added to the solution (experiments 131-137).

TABLE 22

Gefitinib - concentration of gefitinib (mg/L) after 3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 131 | I | Gefitinib (raw) 1000 mg | 100 | — | — | 121.8 | 153.1 | 148.1 |
| 132 | I + P + S | Gefitinib (raw) 1000 mg | 35 | PVP30K 1850 mg | Soluplus 715 mg | 63.6 | 158.3 | 191.1 |
| 133 | I + P + S | Gefitinib (raw) 1000 mg | 35 | HPMCP HP55 1850 mg | Soluplus 715 mg | 70.6 | 230.3 | 296.4 |
| 134 | I/P | Gefitinib 1000 mg | 35 | PVP30K 1850 mg | — | 501.2 | 267.2 | 250.9 |
| 135 | I/P | Gefitinib 1000 mg | 35 | HPMCP HP55 1850 mg | — | 254.1 | 321.4 | 332.1 |
| 136 | I/P + S | Gefitinib 1000 mg | 35 | PVP30K 1850 mg | Soluplus 715 mg | 561.4 | 430.2 | 410.9 |
| 137 | I/P + S | Gefitinib 1000 mg | 35 | HPMCP HP55 1850 mg | Soluplus 715 mg | 319.8 | 576.3 | 594.2 |

TABLE 23

Percentage solubilized gefitinib after 40 minutes dissolution, the Area Under the Curve (AUC - mg/min/L) during 80 minutes dissolution and the AUC increase with stable, amorphous hybrid nanoparticles of the invention, compared to non-formulated gefitinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 131 | I | Gefitinib (raw) 1000 mg | 100 | — | — | 15.3 | 5967 | — |

TABLE 23-continued

Percentage solubilized gefitinib after 40 minutes dissolution, the Area Under
the Curve (AUC - mg/min/L) during 80 minutes dissolution and the AUC increase
with stable, amorphous hybrid nanoparticles of the invention, compared to
non-formulated gefitinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 132 | I + P + S | Gefitinib (raw) 1000 mg | 35 | PVP30K 1850 mg | Soluplus 715 mg | 15.8 | 6630 | 1.1 |
| 133 | I + P + S | Gefitinib (raw) 1000 mg | 35 | HPMCP HP55 1850 mg | Soluplus 715 mg | 23.0 | 9826 | 1.6 |
| 134 | I/P | Gefitinib 1000 mg | 35 | PVP30K 1850 mg | — | 26.7 | 10954 | 1.8 |
| 135 | I/P | Gefitinib 1000 mg | 35 | HPMCP HP55 1850 mg | — | 32.1 | 12794 | 2.1 |
| 136 | I/P + S | Gefitinib 1000 mg | 35 | PVP30K 1850 mg | Soluplus 715 mg | 43.0 | 12282 | 2.9 |
| 137 | I/P + S | Gefitinib 1000 mg | 35 | HPMCP HP55 1850 mg | Soluplus 715 mg | 57.6 | 22774 | 3.8 |

The experiments 131-137 show that a solubility increase is obtained with compositions comprising stable, amorphous hybrid nanoparticles of the invention, with gefitinib, in particular gefitinib and a polymeric stabilizing and matrix-forming component, wherein a separate solubilizer is added to the composition. Particular improvements are achieved with the polymeric stabilizing and matrix-forming component polyvinylpyrrolidone K-30 (PVP 30K) and hydroxy propyl methyl cellulose phthalate (HPMCP HP55). Further, improvements are achieved by the addition of a separate solubilizer added, wherein said solubilizer is polyvinyl caprolactam-polyvinyl acetate-polyethylene glycol copolymer (Soluplus).

Example 7

Compositions with Stable, Amorphous Hybrid Nanoparticles with Dasatinib—Solubility at pH 6.5

A number of experiments were carried out, wherein dasatinib represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 24 and 25, where Table 24 provides data of concentration of dasatinib (mg/L) after 3, 40 and 80 minutes dissolution, whereas Table 25 provides data of % solubilized dasatinib after 40 minutes dissolution, the Area Under the Curve (AUC—mg/min/L) during 80 minutes dissolution and the AUC increase with stable, amorphous hybrid nanoparticles of the invention, compared to non-formulated dasatinib added to the solution (experiments 138-141).

TABLE 24

Dasatinib - concentration of dasatinib (mg/L) after 3, 40
and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 138 | I | Dasatinib (raw) 1000 mg | 100 | — | — | 34.5 | 59.7 | 63.5 |
| 139 | I + P + S | Dasatinib (raw) 1000 mg | 35 | Kollidon VA64 1850 mg | Soluplus 715 mg | 24.2 | 64.9 | 82.5 |
| 140 | I/P | Dasatinib 1000 mg | 35 | Kollidon VA64 1850 mg | — | 54.7 | 382.0 | 417.6 |
| 141 | I/P + S | Dasatinib 1000 mg | 35 | Kollidon VA64 1850 mg | Soluplus 715 mg | 199.9 | 599.8 | 643.8 |

TABLE 25

Percentage solubilized dasatinib after 40 minutes dissolution, the Area Under
the Curve (AUC - mg/min/L) during 80 minutes dissolution and the AUC increase
with stable, amorphous hybrid nanoparticles of the invention, compared to
non-formulated dasatinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 138 | I | Dasatinib (raw) 1000 mg | 100 | — | — | 6.0 | 2396 | — |
| 139 | I + P + S | Dasatinib (raw) 1000 mg | 35 | Kollidon VA64 1850 mg | Soluplus 715 mg | 6.5 | 2750 | 1.1 |
| 140 | I/P | Dasatinib 1000 mg | 35 | Kollidon VA64 1850 mg | — | 35.3 | 15252 | 6.4 |
| 141 | I/P + S | Dasatinib 1000 mg | 35 | Kollidon VA64 1850 mg | Soluplus 715 mg | 58.6 | 24156 | 10.1 |

Experiments 138-141 show that a solubility increase is obtained with compositions comprising stable, amorphous hybrid nanoparticles of the invention, with dasatinib, in particular dasatinib and a polymeric stabilizing and matrix-forming component, wherein a separate solubilizer is added to the composition. Particular improvements are achieved with the polymeric stabilizing and matrix-forming component copolyvidone (Kollidon VA64). Further, improvements are achieved by the addition of a separate solubilizer added, wherein said solubilizer is polyvinyl caprolactam-polyvinyl acetate-polyethylene glycol copolymer (Soluplus).

Example 8

Compositions with Stable, Amorphous Hybrid Nanoparticles with Sorafenib Tosylate—Solubility at pH 6.5

A number of experiments were carried out, wherein sorafenib tosylate represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 26 and 27, where Table 26 provides data of concentration of sorafenib (mg/L) after 3, 40 and 80 minutes dissolution, whereas Table 27 provides data of % solubilized sorafenib after 40 minutes dissolution, the Area Under the Curve (AUC—mg/min/L) during 80 minutes dissolution and the AUC increase of compositions, compared to non-formulated sorafenib tosylate added to the solution (experiments 142-145).

TABLE 26

Sorafenib tosylate - concentration of sorafenib (mg/L) after
3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 142 | I | Sorafenib tosylate (raw) 1000 mg | 100 | — | — | 59.1 | 343.51 | 311.5 |
| 143 | I + P + S | Sorafenib tosylate (raw) 1000 mg | 35 | HPMCP HP55 1850 mg | Soluplus 715 mg | 33.9 | 297.1 | 352.2 |
| 144 | I/P | Sorafenib tosylate 1000 mg | 35 | HPMCP HP55 1850 mg | — | 245.3 | 520.3 | 613.8 |
| 145 | I/P + S | Sorafenib tosylate 2000 mg | 35 | HPMCP HP55 1850 mg | Soluplus 715 mg | 335.1 | 1202.6 | 1738.1 |

TABLE 27

Percentage solubilized sorafenib after 40 minutes dissolution, the Area Under the Curve (AUC - mg/min/L) during 80 minutes dissolution and the AUC increase with stable, amorphous hybrid nanoparticles of the invention, compared to non-formulated sorafenib tosylate added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 142 | I | Sorafenib tosylate (raw) 1000 mg | 100 | — | — | 34.4 | 12001 | — |
| 143 | I + P + S | Sorafenib tosylate (raw) 1000 mg | 35 | HPMCP HP55 1850 mg | Soluplus 715 mg | 33.9 | 11588 | 1.0 |
| 144 | I/P | Sorafenib tosylate 1000 mg | 35 | HPMCP HP55 1850 mg | — | 245.3 | 21838 | 1.8 |
| 145 | I/P + S | Sorafenib tosylate 2000 mg | 35 | HPMCP HP55 1850 mg | Soluplus 715 mg | 335.1 | 52948 | 4.4 |

Experiments 138-141 show that a solubility increase is obtained with compositions comprising stable, amorphous hybrid nanoparticles of the invention, with dasatinib, in particular dasatinib and a polymeric stabilizing and matrix-forming component, wherein a separate solubilizer is added to the composition. Particular improvements are achieved with the polymeric stabilizing and matrix-forming component hydroxy propyl methyl cellulose phthalate (HPMCP HP55). Further, improvements are achieved by the addition of a separate solubilizer added, wherein said solubilizer is polyvinyl caprolactam-polyvinyl acetate-polyethylene glycol copolymer (Soluplus).

Example 9

Compositions with Stable, Amorphous Hybrid Nanoparticles with Nilotinib Base—Solubility at pH 6.5

A number of experiments were carried out, wherein nilotinib base represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 28 and 29, where Table 28 provides data of concentration of nilotinib base (mg/L) after 3, 40 and 80 minutes dissolution, whereas Table 29 provides data of % solubilized nilotinib base after 40 minutes dissolution, the Area Under the Curve (AUC—mg/min/L) during 80 minutes dissolution and the AUC increase of compositions, compared to non-formulated nilotinib base added to the solution (experiments 146-149).

TABLE 28

Nilotinib base - concentration of nilotinib base (mg/L) after 3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 146 | I/P | Nilotinib base 500 mg | 40 | HPMCP HP55 750 mg | — | 12.7 | 5.3 | 3.7 |
| 147 | I/P | Nilotinib base 500 mg | 40 | PVAP 750 mg | — | 12.3 | 8.6 | 7.0 |
| 148 | I/P + S | Nilotinib base 500 mg | 40 | HPMCP HP55 750 mg | Soluplus 715 mg | 136.8 | 88.8 | 41.2 |
| 149 | I/P + S | Nilotinib base 500 mg | 40 | PVAP 750 mg | Soluplus 715 mg | 20.7 | 115.9 | 60.4 |

TABLE 29

Percentage solubilized nilotinib base after 40 minutes dissolution, the Area Under the Curve (AUC - mg/min/L) during 80 minutes dissolution and the AUC increase with stable, amorphous hybrid nanoparticles of the invention, compared to non-formulated nilotinib base added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 146 | I/P | Nilotinib base 500 mg | 40 | HPMCP HP55 750 mg | — | 1.1 | 242 | 8.3 |
| 147 | I/P | Nilotinib base 500 mg | 40 | PVAP 750 mg | — | 1.7 | 328 | 11.2 |
| 148 | I/P + S | Nilotinib base 500 mg | 40 | HPMCP HP55 750 mg | Soluplus 715 mg | 17.8 | 3529 | 120.9 |
| 149 | I/P + S | Nilotinib base 500 mg | 40 | PVAP 750 mg | Soluplus 715 mg | 23.2 | 3544 | 121.4 |

Example 10

Compositions with Stable, Amorphous Hybrid Nanoparticles with Crizotinib—Solubility at pH 6.5

A number of experiments were carried out, wherein crizotinib represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above. Representative results in FaSSIF solution are provided below in Table 30 and 31, where Table 30 provides data of concentration of crizotinib (mg/L) after 3, 40 and 80 minutes dissolution, whereas Table 31 provides data of % solubilized crizotinib after 40 minutes dissolution, the Area Under the Curve (AUC—mg/min/L) during 80 minutes dissolution and the AUC increase with stable, amorphous hybrid nanoparticles of the invention, compared to non-formulated crizotinib added to the solution (experiments 150-156).

TABLE 30

Crizotinib - concentration of crizotinib (mg/L) after 3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 150 | I | Crizotinib (raw) 1000 mg | 100 | — | — | 89.3 | 226.5 | 295.6 |
| 151 | I + P + S | Crizotinib (raw) 1000 mg | 25 | PVP30K 3000 mg | Soluplus 715 mg | 176.2 | 368.5 | 414.6 |
| 152 | I + P + S | Crizotinib (raw) 1000 mg | 25 | PVP30K 3000 mg | Cremophor RH40 715 mg | 161.2 | 428.4 | 497.7 |
| 153 | I/P | Crizotinib 1000 mg | 25 | PVP30K 3000 mg | — | 325.9 | 390.4 | 398.8 |
| 154 | I/P | Crizotinib 1000 mg | 25 | Kollidon VA64 3000 mg | — | 297.5 | 447.6 | 449.9 |
| 155 | I/P + S | Crizotinib 1000 mg | 25 | PVP30K 3000 mg | Soluplus 715 mg | 457.6 | 581.4 | 578.9 |
| 156 | I/P + S | Crizotinib 1000 mg | 25 | PVP30K 3000 mg | Cremophor RH40 715 mg | 573.9 | 855.1 | 867.2 |

TABLE 31

Percentage solubilized crizotinib after 40 minutes dissolution, the Area Under the Curve (AUC - mg/min/L) during 80 minutes dissolution and the AUC increase with stable, amorphous hybrid nanoparticles of the invention, compared to non-formulated crizotinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 150 | I | Crizotinib (raw) 1000 mg | 100 | — | — | 22.7 | 16773 | |

TABLE 31-continued

Percentage solubilized crizotinib after 40 minutes dissolution, the Area Under the Curve (AUC - mg/min/L) during 80 minutes dissolution and the AUC increase with stable, amorphous hybrid nanoparticles of the invention, compared to non-formulated crizotinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 151 | I + P + S | Crizotinib (raw) 1000 mg | 25 | PVP30K 3000 mg | Soluplus 715 mg | 36.8 | 27185 | 1.6 |
| 152 | I + P + S | Crizotinib (raw) 1000 mg | 25 | PVP30K 3000 mg | Cremophor RH40 715 mg | 42.8 | 30423 | 1.8 |
| 153 | I/P | Crizotinib 1000 mg | 25 | PVP30K 3000 mg | — | 39.1 | 29958 | 1.8 |
| 154 | I/P | Crizotinib 1000 mg | 25 | Kollidon VA64 3000 mg | — | 44.8 | 33611 | 2.0 |
| 155 | I/P + S | Crizotinib 1000 mg | 25 | PVP30K 3000 mg | Soluplus 715 mg | 58.1 | 44862 | 2.7 |
| 156 | I/P + S | Crizotinib 1000 mg | 25 | PVP30K 3000 mg | Cremophor RH40 715 mg | 85.5 | 64338 | 3.8 |

Experiments 150-156 show that a solubility increase is obtained with compositions comprising stable, amorphous hybrid nanoparticles of the invention, with crizotinib, in particular crizotinib and a polymeric stabilizing and matrix-forming component, wherein a separate solubilizer is added to the composition. Particular improvements are achieved with the polymeric stabilizing and matrix-forming component polyvinylpyrrolidone K-30 (PVP 30K) and copolyvidone (Kollidon VA64). Further, improvements are achieved by the addition of a separate solubilizer added, wherein said solubilizer is selected from polyvinyl caprolactam-polyvinyl acetate-polyethylene glycol copolymer (Soluplus) and PEG-40 hydrogenated castor oil (Cremophor RH40).

Example 11

Compositions with Stable, Amorphous Hybrid Nanoparticles with Axitinib—Solubility at pH 6.5

A number of experiments were carried out, wherein axitinib represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above.

Representative results in FaSSIF solution are provided below in Table 32 and 33, where Table 32 provides data of concentration of axitinib (mg/L) after 3, 40 and 80 minutes dissolution, whereas Table 33 provides data of % solubilized axitinib after 40 minutes dissolution, the Area Under the Curve (AUC—mg/min/L) during 80 minutes dissolution and the AUC increase with stable, amorphous hybrid nanoparticles of the invention, compared to non-formulated axitinib added to the solution (experiments 157-163).

TABLE 32

Axitinib - concentration of axitinib (mg/L) after 3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 157 | I | Axitinib (raw) 500 mg | 100 | — | — | 0.6 | 0.6 | 0.6 |
| 158 | I + P + S | Axitinib (raw) 500 mg | 25 | Kollidon VA64 1500 mg | Soluplus 715 mg | 0.2 | 0.8 | 4.3 |
| 159 | I + P + S | Axitinib (raw) 500 mg | 25 | HPMC AS 1500 mg | Soluplus 715 mg | 0.2 | 3.0 | 3.1 |
| 160 | I/P | Axitinib 500 mg | 25 | Kollidon VA64 1500 mg | — | 71.1 | 25.9 | 9.1 |
| 161 | I/P | Axitinib 500 mg | 25 | HPMC AS 1500 mg | — | 17.6 | 21.0 | 16.4 |
| 162 | I/P + S | Axitinib 500 mg | 25 | Kollidon VA64 1500 mg | Soluplus 715 mg | 77.6 | 223.6 | 266.1 |
| 163 | I/P + S | Axitinib 500 mg | 25 | HPMC AS 1500 mg | Soluplus 715 mg | 40.3 | 110.3 | 129.9 |

TABLE 33

Percentage solubilized axitinib after 40 minutes dissolution, the Area Under the Curve (AUC - mg/min/L) during 80 minutes dissolution and the AUC increase with stable, amorphous hybrid nanoparticles of the invention, compared to non-formulated axitinib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 157 | I | Axitinib (raw) 500 mg | 100 | — | — | 0.1 | 47 | |
| 158 | I + P + S | Axitinib (raw) 500 mg | 25 | Kollidon VA64 1500 mg | Soluplus 715 mg | 0.2 | 126 | 2.7 |
| 159 | I + P + S | Axitinib (raw) 500 mg | 25 | HPMC AS 1500 mg | Soluplus 715 mg | 0.6 | 193 | 4.1 |
| 160 | I/P | Axitinib 500 mg | 25 | Kollidon VA64 1500 mg | — | 5.2 | 3255 | 69.0 |
| 161 | I/P | Axitinib 500 mg | 25 | HPMC AS 1500 mg | — | 4.2 | 1571 | 33.0 |
| 162 | I/P + S | Axitinib 500 mg | 25 | Kollidon VA64 1500 mg | Soluplus 715 mg | 44.7 | 16070 | 341.0 |
| 163 | I/P + S | Axitinib 500 mg | 25 | HPMC AS 1500 mg | Soluplus 715 mg | 22.1 | 7954 | 169.0 |

Experiments 157-163 show that a solubility increase is obtained with compositions comprising stable, amorphous hybrid nanoparticles of the invention, with axitinib, in particular axitinib and a polymeric stabilizing and matrix-forming component, wherein a separate solubilizer is added to the composition. Particular improvements are achieved with the polymeric stabilizing and matrix-forming component copolyvidone (Kollidon VA64) and hydroxypropyl methylcellulose acetate succinate (HPMC AS). Further, improvements are achieved by the addition of a separate solubilizer added, wherein said solubilizer is polyvinyl caprolactam-polyvinyl acetate-polyethylene glycol copolymer (Soluplus).

Example 12

Compositions with Stable, Amorphous Hybrid Nanoparticles with Vemurafenib—Solubility at pH 6.5

A number of experiments were carried out, wherein vemurafenib represented the PKI. The experiments were carried out by measuring concentration of PKI (mg/L) after 3, 40 and 80 minutes dissolution in a solution at about pH 6.5, namely FaSSIF (Fasted State Simulated Intestinal Fluid). Samples of the solution were taken at various time intervals and the amount of PKI was measured by the dissolution measurement assay described above Representative results in FaSSIF solution are provided below in Table 34 and 35, where Table 34 provides data of concentration of vemurafenib (mg/L) after 3, 40 and 80 minutes dissolution, whereas Table 35 provides data of % solubilized vemurafenib after 40 minutes dissolution, the Area Under the Curve (AUC—mg/min/L) during 80 minutes dissolution and the AUC increase with stable, amorphous hybrid nanoparticles of the invention, compared to non-formulated vemurafenib added to the solution (experiments 164-170).

TABLE 34

Vemurafenib - concentration of vemurafenib (mg/L) after 3, 40 and 80 minutes dissolution in FaSSIF solution (pH 6.5).

| Exp | Comp. | Inhibitor (I) | Drug load ratio (%) | Polymeric stab. matrix. Component (P) | Solubilizer (S) | Conc (mg/L) 3 min | Conc (mg/L) 40 min | Conc (mg/L) 80 min |
|---|---|---|---|---|---|---|---|---|
| 164 | I | Vemurafenib (raw) 500 mg | 100 | — | — | 0.3 | 0.3 | 0.4 |
| 165 | I + P + S | Vemurafenib (raw) 500 mg | 25 | Kollidon VA64 1500 mg | Soluplus 715 mg | 0.2 | 0.2 | 0.4 |
| 166 | I + P + S | Vemurafenib (raw) 500 mg | 25 | CAP 1500 mg | Soluplus 715 mg | 0.1 | 0.2 | 0.4 |
| 167 | I/P | Vemurafenib 500 mg | 25 | Kollidon VA64 1500 mg | — | 35.5 | 107.6 | 122.9 |
| 168 | I/P | Vemurafenib 500 mg | 25 | CAP 1500 mg | — | 75.1 | 47.5 | 11.8 |
| 169 | I/P + S | Vemurafenib 500 mg | 25 | Kollidon VA64 1500 mg | Soluplus 715 mg | 27.4 | 111.3 | 172.3 |
| 170 | I/P + S | Vemurafenib 500 mg | 25 | CAP 1500 mg | Soluplus 715 mg | 55.4 | 105.7 | 118.9 |

TABLE 35

Percentage solubilized vemurafenib after 40 minutes dissolution, the Area Under the Curve (AUC - mg/min/L) during 80 minutes dissolution and the AUC increase with stable, amorphous hybrid nanoparticles of the invention, compared to non-formulated vemurafenib added to the FaSSIF solution (pH 6.5).

| Exp | Comp. | Inhibitor (I) | Drug load ratio (%) | Polymeric stab. matrix. Component (P) | Solubilizer (S) | % solubilized 40 min. | AUC/ 80 min Mg/min/L | AUC increase |
|---|---|---|---|---|---|---|---|---|
| 164 | I | Vemurafenib (raw) 500 mg | 100 | — | — | 0.1 | 27 | |
| 165 | I + P + S | Vemurafenib (raw) 500 mg | 25 | Kollidon VA64 1500 mg | Soluplus 715 mg | 0.1 | 21 | 0.8 |
| 166 | I + P + S | Vemurafenib (raw) 500 mg | 25 | CAP 1500 mg | Soluplus 715 mg | 0.0 | 18 | 0.7 |
| 167 | I/P | Vemurafenib 500 mg | 25 | Kollidon VA64 1500 mg | — | 21.5 | 7669 | 288.0 |
| 168 | I/P | Vemurafenib 500 mg | 25 | CAP 1500 mg | — | 9.5 | 3761 | 141.0 |
| 169 | I/P + S | Vemurafenib 500 mg | 25 | Kollidon VA64 1500 mg | Soluplus 715 mg | 22.3 | 8564 | 322.0 |
| 170 | I/P + S | Vemurafenib 500 mg | 25 | CAP 1500 mg | Soluplus 715 mg | 21.1 | 7899 | 297.0 |

Experiments 164-170 show that a solubility increase is obtained with compositions comprising stable, amorphous hybrid nanoparticles of the invention, with vemurafenib, in particular vemurafenib and a polymeric stabilizing and matrix-forming component, wherein a separate solubilizer is added to the composition. Particular improvements are achieved with the polymeric stabilizing and matrix-forming component copolyvidone (Kollidon VA64) and cellulose acetate phthalate (CAP). Further, improvements are achieved by the addition of a separate solubilizer added, wherein said solubilizer is polyvinyl caprolactam-polyvinyl acetate-polyethylene glycol copolymer (Soluplus).

Example 13

Dissolution Rate Measurement in Sink Conditions of Compositions of the Invention Dissolution measurement in sink conditions of compositions of the invention were measured in a method consisting of adding the wished amount of powder into a flow through cell system (SOTAX, Allschwill, Switzerland), mounting the cell onto its apparatus and then pumping the appropriate medium (typically FaSSIF, FeSSIF, SGF) through the powder. The temperature of the apparatus was set to 37° C. The amount of powder added into the cell depends on drug load of the powder: The exact amount of powder was calculated from results obtained from drug load analysis of the powders.

Typically, 3.5 to 7 mg PKI was added into the flow through cell and a flow rate between 8 and 16 ml medium/min (preferably about 8 ml medium/min) was pumped through the powder. One ml samples of the medium passing through the cell were collected at predetermined times. These samples were analyzed by HPLC (e.g. C18 column Eclipse, 4.6 mm×15 cm, 1 ml/min, detection 254-400 nm). Samples were taken after 0, 0.5, 1, 1.5, 2, 3, 4, 5, 6, 7, 8, 9, 10, 15, 20, 25, 30, 35 and 40 min from the moment the medium comes out from the flow through cell. The accumulated % solubilized of the amount of active substance added into the flow through cell was calculated and plotted against time (min). The initial slope ("initial dissolution rate") of the graph was estimated, as measured during 0 to 10 minutes, and taken as the dissolution rate of the material in sink condition at 37° C. in the given dissolution medium.

Each experiment comprises a comparison between the PKI in raw form with compositions comprising stable, amorphous hybrid particles of the invention with the inhibitor and a representative polymeric stabilizing and matrix-forming component.

Example 13.1

Dissolution Rate Measurement in Sink Conditions of Compositions of the Invention, Comprising Nilotinib HCl In experiments with nilotinib HCl, 4 mg was weighed in the flow through cell (experiment 500) and compared with stable, amorphous hybrid nanoparticles of the invention with nilotinib base and the polymeric stabilizing and matrix-forming component HPMCP HP55 (experiment 501). The results are depicted in Table 36 below.

TABLE 36

| Nilotinib HCl sink condition in FaSSIF. | | |
|---|---|---|
| | Experiment 500 | Experiment 501 |
| Composition type | I | I/P |
| Inhibitor (I) | nilotinib HCl (raw) | nilotinib base |
| Polymeric stab. matrix. Component (P) | — | HPMCP HP55 |
| Drug load % | — | 40% |
| Accumulated % of solubilized of remaining active substance at a given time (min) | | |
| Min. | % | % |
| 0 | 0.13 | 3.07 |
| 0.5 | 0.33 | 7.96 |
| 1 | 0.49 | 12.23 |
| 1.5 | 0.63 | 15.22 |
| 2 | 0.76 | 17.91 |
| 3 | 1.02 | 23.25 |
| 4 | 1.24 | 28.03 |
| 5 | 1.48 | 32.70 |
| 6 | 1.71 | 37.32 |

TABLE 36-continued

Nilotinib HCl sink condition in FaSSIF.

| | | |
|---|---|---|
| 7 | 1.92 | 42.04 |
| 8 | 2.13 | 45.78 |
| 9 | 2.34 | 49.52 |
| 10 | 2.56 | 52.34 |
| 15 | 3.51 | 59.66 |
| 20 | 4.31 | 66.28 |
| 25 | 5.04 | 70.92 |
| 30 | 5.7 | 74.38 |
| 35 | 6.4 | 76.25 |
| 40 | 7.0 | 80.33 |

| | Initial Dissolution Rate |
|---|---|
| EXP 500 | 0.27 |
| EXP 501 | 6.58 |
| Ratio 501/500 | 24.0 |

Experiments 500-501 show that the initial dissolution rate of the stable, amorphous hybrid nanoparticles of the invention, with nilotinib base, is superior to the initial dissolution rate of nilotinib HCl in raw, crystalline form.

Example 13.2

Dissolution Rate Measurement in Sink Conditions of Compositions of the Invention Comprising Erlotinib HCl In experiments with erlotinib HCl, 3.5 mg was weighed in the flow through cell (experiment 510) and compared with stable, amorphous hybrid nanoparticles of the invention with erlotinib HCl and the polymeric stabilizing and matrix-forming component HPMC AS (experiment 511). The results are depicted in Table 37 below.

TABLE 37

Erlotinib HCl sink condition in FaSSIF.

| | Experiment 510 | Experiment 511 |
|---|---|---|
| Composition type | I | I/P |
| Inhibitor (I) | erlotinib HCl (raw) | erlotinib HCl |
| Polymeric stab. matrix. Component (P) | — | HPMC AS |
| Drug load % | — | 35% |

Accumulated % of solubilized of remaining active substance at a given time (min)

| Min. | % | % |
|---|---|---|
| 0 | 0.26 | 2.3 |
| 0.5 | 0.49 | 3.9 |
| 1 | 0.63 | 5.4 |
| 1.5 | 0.71 | 6.4 |
| 2 | 0.77 | 7.2 |
| 3 | 0.85 | 8.5 |
| 4 | 0.91 | 9.5 |
| 5 | 0.96 | 10.3 |
| 6 | 1.01 | 11.1 |
| 7 | 1.06 | 11.8 |
| 8 | 1.10 | 12.5 |
| 9 | 1.13 | 13.1 |
| 10 | 1.17 | 13.8 |
| 20 | 1.58 | 19.3 |
| 30 | 1.93 | 22.0 |
| 40 | 2.24 | 24.6 |

TABLE 37-continued

Erlotinib HCl sink condition in FaSSIF.

| | Initial Dissolution Rate |
|---|---|
| EXP 510 | 0.303 |
| EXP 511 | 2.754 |
| Ratio 511/510 | 9.1 |

Experiments 510-511 show that the initial dissolution rate of the compositions comprising stable, amorphous hybrid nanoparticles of the invention, with erlotinib HCl and the polymeric stabilizing and matrix-forming component HPMC AS, is superior to the initial dissolution rate of erlotinib HCl in raw, crystalline form.

Example 13.3

Dissolution Rate Measurement in Sink Conditions of Compositions of the Invention Comprising Pazopanib HCl In experiments with pazopanib HCl, 3.5 mg was weighed in the flow through cell (experiment 520) and compared with stable, amorphous hybrid nanoparticles of the invention with pazopanib HCl and the polymeric stabilizing and matrix-forming component PVP90K (experiment 521). The results are depicted in Table 38 below.

TABLE 38

Pazopanib HCl sink condition in FaSSIF.

| | Experiment 520 | Experiment 521 |
|---|---|---|
| Composition type | I | I/P |
| Inhibitor (I) | pazopanib HCl (raw) | pazopanib HCl |
| Polymeric stab. matrix. Component (P) | — | PVP90K |
| Drug load % | — | 35% |

Accumulated % of solubilized of remaining active substance at a given time (min)

| Min. | % | % |
|---|---|---|
| 0 | 1.6 | 1.9 |
| 0.5 | 4.7 | 4.6 |
| 1 | 7.7 | 6.8 |
| 1.5 | 9.6 | 8.8 |
| 2 | 11.2 | 10.6 |
| 3 | 13.4 | 15.2 |
| 4 | 14.7 | 19.7 |
| 5 | 15.4 | 22.7 |
| 6 | 16.0 | 26.2 |
| 7 | 16.4 | 30.1 |
| 8 | 16.9 | 33.8 |
| 9 | 17.2 | 38.2 |
| 10 | 17.6 | 41.7 |
| 20 | 19.2 | 73.2 |
| 30 | 20.5 | 91.3 |
| 40 | 21.6 | 97.1 |

| | Initial Dissolution Rate | Dissolution Rate (5-10 min) |
|---|---|---|
| EXP 520 | 4.8 | 0.428 |
| EXP 521 | 4.33 | 3.85 |
| Ratio 521/520 | 0.9 | 9.0 |

Experiments 520-521 show that the initial dissolution rate of the compositions comprising stable, amorphous hybrid nanoparticles of the invention, with pazopanib HCl and the polymeric stabilizing and matrix-forming component PVP90K, is superior to the initial dissolution rate of pazopanib HCl in raw, crystalline form.

Example 13.4

Dissolution Rate Measurement in Sink Conditions of Compositions of the Invention Comprising Lapatinib Ditosylate In experiments with lapatinib ditosylate, 4 mg was weighed in the flow through cell (experiment 530) and compared with stable, amorphous hybrid nanoparticles of the invention with lapatinib base and the polymeric stabilizing and matrix-forming component HPC lf (experiment 531). The results are depicted in Table 39 below.

TABLE 39

Lapatinib ditosylate sink condition in FaSSIF.

|  | Experiment 530 | Experiment 531 |
| --- | --- | --- |
| Composition type | I | I/P |
| Inhibitor (I) | Lapatinib ditosylate (raw) | Lapatinib base |
| Polymeric stab. matrix. Component (P) | — | HPC lf |
| Drug load % | — | 66% |

Accumulated % of solubilized of remaining active substance at a given time (min)

| Min. | % | % |
| --- | --- | --- |
| 0 | 0.032 | 0.442 |
| 0.5 | 0.088 | 1.736 |
| 1 | 0.141 | 3.053 |
| 1.5 | 0.190 | 4.448 |
| 2 | 0.238 | 5.771 |
| 3 | 0.332 | 7.504 |
| 4 | 0.422 | 8.783 |
| 5 | 0.505 | 9.736 |
| 6 | 0.582 | 10.573 |
| 7 | 0.655 | 11.209 |
| 8 | 0.725 | 11.732 |
| 9 | 0.790 | 12.179 |
| 10 | 0.851 | 12.576 |
| 20 | 1.272 | 14.128 |
| 30 | 1.607 | 15.168 |
| 40 | 1.944 | 15.802 |

|  | Initial Dissolution Rate |
| --- | --- |
| EXP 530 | 0.103 |
| EXP 531 | 2.674 |
| Ratio 531/530 | 25.9 |

Experiments 530-531 show that the initial dissolution rate of the compositions comprising stable, amorphous hybrid nanoparticles of the invention, with lapatinib base and the polymeric stabilizing and matrix-forming component HPC lf, is superior to the initial dissolution rate of lapatinib ditosylate in raw, crystalline form.

Example 13.5

Dissolution Rate Measurement in Sink Conditions of Compositions of the Invention Comprising Gefitinib In experiments with gefitinib, 3.5 mg was weighed in the flow through cell (experiment 540) and compared with stable, amorphous hybrid nanoparticles of the invention with gefitinib and the polymeric stabilizing and matrix-forming component HPMCP HP55 (experiment 541). The results are depicted in Table 40 below.

TABLE 40

Gefitinib sink condition in FaSSIF.

|  | Experiment 540 | Experiment 541 |
| --- | --- | --- |
| Composition type | I | I/P |
| Inhibitor (I) | Gefitinib (raw) | Gefitinib |
| Polymeric stab. matrix. Component (P) | — | HPMCP HP55 |
| Drug load % | — | 35% |

Accumulated % of solubilized of remaining active substance at a given time (min)

| Min. | % | % |
| --- | --- | --- |
| 0 | 0.1 | 1.8 |
| 0.5 | 0.9 | 6.7 |
| 1 | 1.9 | 11.3 |
| 1.5 | 3.2 | 15.4 |
| 2 | 4.5 | 19.0 |
| 3 | 7.0 | 23.6 |
| 4 | 9.5 | 27.4 |
| 5 | 11.9 | 30.5 |
| 6 | 14.3 | 33.5 |
| 7 | 16.6 | 36.0 |
| 8 | 18.8 | 37.8 |
| 9 | 20.7 | 39.9 |
| 10 | 22.7 | 42.6 |
| 20 | 29.9 | 50.6 |
| 30 | 34.1 | 56.7 |
| 40 | 36.7 | 61.8 |

|  | Initial Dissolution Rate |
| --- | --- |
| EXP 540 | 2.2 |
| EXP 541 | 8.6 |
| Ratio 541/540 | 3.9 |

Experiments 540-541 show that the initial dissolution rate of the compositions comprising stable, amorphous hybrid nanoparticles of the invention, with gefitinib and the polymeric stabilizing and matrix-forming component HPMCP HP55, is superior to the initial dissolution rate of the gefinib in raw, crystalline form.

Example 13.6

Dissolution Rate Measurement in Sink Conditions of Compositions of the Invention Comprising Dasatinib In experiments with dasatinib, 3.5 mg was weighed in the flow through cell (experiment 550) and compared with stable, amorphous hybrid nanoparticles of the invention with dasatinib and the polymeric stabilizing and matrix-forming component copolyvidon—Kollidon VA64 (experiment 551). The results are depicted in Table 41 below.

TABLE 41

Dasatinib sink condition in FaSSIF.

| | Experiment 550 | Experiment 551 |
|---|---|---|
| Composition type | I | I/P |
| Inhibitor (I) | Dasatinib (raw) | Dasatinib |
| Polymeric stab. matrix. Component (P) | — | Kollidon VA64 |
| Drug load % | — | 35% |

Accumulated % of solubilized of remaining active substance at a given time (min)

| Min. | % | % |
|---|---|---|
| 0 | 0.3 | 0.4 |
| 0.5 | 0.7 | 1.0 |
| 1 | 1.2 | 1.7 |
| 1.5 | 1.6 | 2.3 |
| 2 | 2.0 | 2.9 |
| 3 | 2.8 | 4.2 |
| 4 | 3.7 | 5.5 |
| 5 | 4.4 | 6.8 |
| 6 | 5.2 | 8.2 |
| 7 | 6.0 | 9.5 |
| 8 | 6.8 | 10.8 |
| 9 | 7.6 | 12.1 |
| 10 | 8.3 | 13.4 |
| 20 | 15.9 | 25.9 |
| 30 | 22.1 | 40.9 |
| 40 | 26.4 | 54.9 |

| | Initial Dissolution Rate |
|---|---|
| EXP 550 | 0.8 |
| EXP 551 | 1.3 |
| Ratio 551/550 | 1.6 |

Experiments 550-551 show that the initial dissolution rate of the compositions comprising stable, amorphous hybrid of the invention, with dasatinib and the polymeric stabilizing and matrix-forming component copolyvidon (Kollidon VA64), is superior to the initial dissolution rate of the dasatinib raw, crystalline form.

Example 13.7

Dissolution Rate Measurement in Sink Conditions of Compositions the Invention Comprising Sorafenib Tosylate In experiments with sorafenib tosylate, 3.5 mg was weighed in the flow through cell (experiment 560) and compared with stable, amorphous hybrid nanoparticles of the invention with sorafenib tosylate and the polymeric stabilizing and matrix-forming component HPMCP HP55 (experiment 561). The results are depicted in Table 42 below.

TABLE 42

Sorafenib tosylate sink condition in FaSSIF.

| | Experiment 560 | Experiment 561 |
|---|---|---|
| Composition type | I | I/P |
| Inhibitor (I) | Sorafenib tosylate (raw) | Sorafenib tosylate |
| Polymeric stab. matrix. Component (P) | — | HPMCP HP55 |
| Drug load % | — | 35% |

TABLE 42-continued

Sorafenib tosylate sink condition in FaSSIF.

Accumulated % of solubilized of remaining active substance at a given time (min)

| Min. | % | % |
|---|---|---|
| 0 | 0.2 | 0.8 |
| 0.5 | 0.4 | 1.7 |
| 1 | 0.7 | 2.4 |
| 1.5 | 1.0 | 3.1 |
| 2 | 1.3 | 3.7 |
| 3 | 1.8 | 4.8 |
| 4 | 2.2 | 5.8 |
| 5 | 2.6 | 6.9 |
| 6 | 3.0 | 8.1 |
| 7 | 3.4 | 9.7 |
| 8 | 3.8 | 11.3 |
| 9 | 4.2 | 13.3 |
| 10 | 4.6 | 15.6 |
| 20 | 8.8 | 32.7 |
| 30 | 12.6 | 61.5 |
| 40 | 16.4 | 96.1 |

| | Initial Dissolution Rate |
|---|---|
| EXP 560 | 0.47 |
| EXP 561 | 1.17 |
| Ratio 561/560 | 2.5 |

Experiments 560-561 show that the initial dissolution rate of the compositions comprising stable, amorphous hybrid nanoparticles of the invention, with sorafenib tosylate and the polymeric stabilizing and matrix-forming component HPMCP HP55, is superior to the initial dissolution rate of sorafenib tosylate in raw, crystalline form.

Example 13.8

Dissolution Rate Measurement in Sink Conditions of Compositions of the Invention Comprising Crizotinib In experiments with crizotinib, 3.5 mg was weighed in the flow through cell (experiment 570) and compared with stable, amorphous hybrid nanoparticles of the invention with crizotinib and the polymeric stabilizing and matrix-forming component PVP 30K (experiment 571). The results are depicted in Table 43 below.

TABLE 43

Crizotinib sink condition in FaSSIF.

| | Experiment 570 | Experiment 571 |
|---|---|---|
| Composition type | I | I/P |
| Inhibitor (I) | Crizotinib (raw) | Crizotinib |
| Polymeric stab. matrix. Component (P) | — | PVP 30K |
| Drug load % | — | 25% |

Accumulated % of solubilized of remaining active substance at a given time (min)

| Min. | % | % |
|---|---|---|
| 0 | 2.0 | 8.8 |
| 0.5 | 5.7 | 30.3 |
| 1 | 8.9 | 47.9 |
| 1.5 | 11.9 | 58.3 |
| 2 | 14.6 | 67.5 |
| 4 | 23.1 | 81.7 |
| 6 | 30.1 | 83.8 |

TABLE 43-continued

| Crizotinib sink condition in FaSSIF. | | |
|---|---|---|
| 8 | 36.0 | 84.2 |
| 10 | 41.0 | 84.4 |
| 20 | 58.9 | 85.1 |
| 30 | 73.1 | 85.3 |
| 40 | 86.3 | 85.5 |

| | Initial Dissolution Rate |
|---|---|
| EXP 570 | 6.6 |
| EXP 571 | 33.3 |
| Ratio 571/570 | 5.0 |

Experiments 570-571 show that the initial dissolution rate of the compositions comprising stable, amorphous hybrid nanoparticles of the invention, with crizotinib and the polymeric stabilizing and matrix-forming component PVP 30K, is superior to the initial dissolution rate of crizotinib in raw, crystalline form.

Example 13.9

Dissolution Rate Measurement in Sink Conditions of Compositions of the Invention Comprising Axitinib In experiments with axitinib, 3.5 mg was weighed in the flow through cell (experiment 580) and compared with stable, amorphous hybrid nanoparticles of the invention with axitinib and the polymeric stabilizing and matrix-forming component Kollidon VA64 (experiment 581) or HPMC AS (experiment 582). The results are depicted in Table 44 below.

TABLE 44

| Axitinib sink condition in FaSSIF. | | | |
|---|---|---|---|
| | Experiment 580 | Experiment 581 | Experiment 582 |
| Composition type | I | I/P | I/P |
| Inhibitor (I) | Axitinib (raw) | Axitinib | Axitinib |
| Polymeric stab. matrix. Component (P) | — | Kollidon VA64 | HPMC AS |
| Drug load % | — | 25% | 25% |

| Accumulated % of solubilized of remaining active substance at a given time (min) | | | |
|---|---|---|---|
| Min. | % | % | % |
| 0 | 0.03 | 0.75 | 0.22 |
| 0.5 | 0.06 | 1.60 | 0.59 |
| 1 | 0.08 | 2.33 | 1.04 |
| 1.5 | 0.11 | 2.97 | 1.50 |
| 2 | 0.13 | 3.56 | 1.92 |
| 4 | 0.23 | 6.03 | 3.25 |
| 6 | 0.31 | 7.76 | 4.39 |
| 8 | 0.40 | 9.74 | 5.34 |
| 10 | 0.49 | 11.81 | 6.17 |
| 20 | 0.97 | 22.04 | 9.03 |
| 30 | 1.46 | 27.42 | 11.43 |
| 40 | 1.96 | 30.53 | 13.52 |

| | Initial Dissolution Rate | |
|---|---|---|
| EXP 580 | 0.051 | |
| EXP 581 & 582 | 1.396 | 0.865 |
| Ratio 581/580 & 582/580 | 27.5 | 17.1 |

Experiments 580-582 show that the initial dissolution rate of the compositions comprising stable, amorphous hybrid nanoparticles of the invention, with axitinib and the polymeric stabilizing and matrix-forming component Kollidon VA64 or HPMC AS, is superior to the initial dissolution rate of axitinib in raw, crystalline form.

Example 13.10

Dissolution Rate Measurement in Sink Conditions of Compositions of the Invention Comprising Vemurafenib In experiments with vemurafenib, 3.5 mg was weighed in the flow through cell (experiment 590) and compared with stable, amorphous hybrid nanoparticles of the invention with vemurafenib and the polymeric stabilizing and matrix-forming component Kollidon VA64 (experiment 591) or CAP (experiment 592). The results are depicted in Table 45 below.

TABLE 45

| Vemurafenib sink condition in FaSSIF. | | | |
|---|---|---|---|
| | Experiment 590 | Experiment 591 | Experiment 592 |
| Composition type | I | I/P | I/P |
| Inhibitor (I) | Vemurafenib (raw) | Vemurafenib | Vemurafenib |
| Polymeric stab. matrix. Component (P) | — | Kollidon VA64 | CAP |
| Drug load % | — | 25% | 25% |

| Accumulated % of solubilized of remaining active substance at a given time (min) | | | |
|---|---|---|---|
| Min. | % | % | % |
| 0 | 0.0 | 0.1 | 0.4 |
| 0.5 | 0.0 | 0.2 | 1.1 |
| 1 | 0.0 | 0.3 | 1.8 |
| 1.5 | 0.0 | 0.4 | 2.4 |
| 2 | 0.0 | 0.5 | 3.1 |
| 4 | 0.0 | 1.2 | 6.3 |
| 6 | 0.0 | 1.9 | 9.4 |
| 8 | 0.0 | 2.4 | 11.0 |
| 10 | 0.0 | 2.9 | 12.1 |
| 20 | 0.0 | 4.7 | 14.9 |
| 30 | 0.1 | 5.9 | 16.8 |
| 40 | 0.1 | 7.1 | 18.3 |

| | Initial Dissolution Rate | |
|---|---|---|
| EXP 590 | 0.002 | |
| EXP 591 & 592 | 0.209 | 1.346 |
| Ratio 591/590 & 592/590 | 104 | 673 |

Experiments 590-592 clearly shows that the initial dissolution rate of the compositions comprising stable, amorphous hybrid nanoparticles of the invention, with vemurafenib and the polymeric stabilizing and matrix-forming component Kollidon VA64 or CAP, is superior to the initial dissolution rate of vemurafenib in raw, crystalline form.

Example 14

In Vivo Measurement of Plasma Levels after Oral Administration of Compositions of the Invention Groups of four beagle dogs received single oral doses (5 mg/kg) of capsule compositions comprising stable, amorphous hybrid nanoparticles of the invention with nilotinib base and either of the polymeric stabilizing and matrix-forming components PVAP or HPMCP HP55, optionally with addition of the solubilizer polyvinyl caprolactam-polyvinyl acetate-polyethylene glycol copolymer, and compared with a marketed formulation comprising nilotinib HCl. The stable, amorphous hybrid nanoparticles tested are as set out in experiments 146-149, in Example 9. The stomach contents of the dogs were either neutralized with a sodium bicarbonate solution 5 min prior to capsule dosing or acidified with an HCl-KCl buffer 10 min prior to dose. One group of dogs also received a single iv dose (1 mg/kg) of nilotinib. Plasma levels of nilotinib were determined with a selective LC-MS/MS method. There were no side-effects observed in any animal studied.

Results and Conclusions

Mean±SEM plasma concentration-time profiles of nilotinib base are shown in FIGS. 22-25, and pharmacokinetic parameters and results are displayed in Tables 46A and 46B.

Outliers were calculated and excluded based on if one value is a significant outlier from the rest at 95% confidence intervals (alpha=5%) according to Grubb's test. The critical Z value for the Grubb's test at the 95% confidence interval with n=4 is 1.48. Z=(Mean −Questionable value)/SD Values are Given as Mean±SD Intravenous (IV) data were obtained by constant rate IV infusion of 1 mg/kg, of a solution of Nilotinib at 0.2 mg/mL, in a 10% HPβCD, pH adjustment to pH 3.3 to 3.5. Co: 511±46 ng/mL, T½: 3.3±1.8 hr; AUC0-24 hr: 1000±300 ng*hr/mL.

The marketed nilotinib formulation administrated to an acidified stomach showed plasma levels about 2 times higher than those after the same formulation administered to a neutralized stomach. Both formulations comprising stable, amorphous hybrid nanoparticles of the invention with nilotinib base with PVAP and HPMCP HP55 as polymeric stabilizing and matrix-forming components showed significant improvements in plasma exposure, with plasma levels about 2-fold higher than those of the marketed formulation given to an acidified stomach. In addition, combining stable, amorphous hybrid nanoparticles produced by the methods of the invention could give a plasma exposure that is be more or less independent of stomach pH.

Further improvements in oral availability were observed when formulations with stable, amorphous hybrid nanopar-

TABLE 46A

Pharmacokinetic data following single oral administration of different nilotinib compositions of the invention, in dogs.

|  | Marketed nilotinib formulation Acidic Stomach | Marketed nilotinib formulation Neutral Stomach | I/P Nilotinib base/PVAP Exp 147 Acidic Stomach | I/P + S Nilotinib base/PVAP + Soluplus Exp 149 Acidic Stomach | I/P Nilotinib base/ PVAP Exp 147 Neutral Stomach |
|---|---|---|---|---|---|
| Cmax, ng/mL | 86 ± 52 | 73 ± 26 | 240 ± 87 | 360 ± 89 | 490 ± 350 |
| Tmax, hr | 7.6 ± 11 | 1.3 ± 0.3 | 1.3 ± 0.3 | 1.3 ± 0.3 | 1.4 ± 0.5 |
| T½, hr | 9.9; 10.7 | 1.9 ± 0.3 | 4.3 ± 3.0 | 3.3 ± 2.0 | 3.4 ± 1.2 |
| AUC 0-24 h, ng * hr/mL | 400 ± 140 | 220 ± 90 | 650 ± 240 | 1260 ± 70 | 1820 ± 1200 |
| F (%) | 7.9 ± 2.9 | 4.4 ± 1.8 | 13 ± 5 | 25 ± 1 | 36 ± 24 |

Values are given as Mean±SD, except for T ½ of the Marketed nilotinib formulation given too acid stomach where only two values were obtained.

Intravenous (IV) data were obtained by constant rate IV infusion of 1 mg/kg, of a solution of Nilotinib at 0.2 mg/mL, in a 10% HPβCD, pH adjustment to pH 3.3 to 3.5. Co: 511±46 ng/mL; T½: 3.3±1.8 hr; AUC0-24 hr: 1000±300 ng*hr/mL ticles of the invention were combined with the solubilizer polyvinyl caprolactam-polyvinyl acetate-polyethylene glycol copolymer. Thus, compositions of the invention with nilotinib base with PVAP and HPMCP HP55 as polymeric stabilizing and matrix-forming components, where the solubilizer polyvinyl caprolactam-polyvinyl acetate-polyethylene glycol copolymer was added and administered to an acidified stomach resulted in plasma levels 2.3- to 3.1-fold

TABLE 46B

Pharmacokinetic data following single oral administration of different nilotinib formulations of the invention, in dogs.

|  | I/P Nilotinib base/ HPMCP HP55 Exp 146 Neutral Stomach | I/P Nilotinib base/ HPMCP HP55 + Soluplus Exp 148 Neutral Stomach | I/P Nilotinib base/ HPMCP HP55 Exp 146 Acidic Stomach | I/P Nilotinib base/ HPMCP HP55 + Soluplus Exp 148 Acidic Stomach |
|---|---|---|---|---|
| Cmax, ng/mL | 210 ± 97 | 560 ± 220 | 380 ± 90 | 270 ± 130 |
| Tmax, hr | 1.1 ± 0.5 | 1.3 ± 0.29 | 1.2 ± 0.3 | 1.0 ± 0.0 |
| T½, hr | 1.9 ± 0.2 | 3.0 ± 1.4 | 3.3 ± 1.3 | 3.8 ± 0.8 |
| AUC 0-24 h, ng * hr/mL | 730 ± 390 | 1600 ± 580 | 1230 ± 110 | 910 ± 630 |
| F (%) | 15 ± 8 | 32 ± 12 | 24 ± 2 | 18 ± 13 | higher than those of the marketed formulation. In this study, high oral bioavailability was achieved with stable, amorphous hybrid nanoparticles of the invention with nilotinib base with HPMCP HP55 as polymeric stabilizing and matrix-forming components, where the solubilizer polyvinyl caprolactam-polyvinyl acetate-polyethylene glycol copolymer was added (I/P+S) and administrated to neutralized stomach contents. In this case the exposure increased about 7-fold over that of the marketed oral formulation administered under the same neutralized conditions. Highest bioavalability, 36±24%, in this study was achieved when stable, amorphous hybrid nanoparticles of the invention with nilotinib base with PVAP as polymeric stabilizing and matrix-forming component was administered to a neutralized stomach. However, this study leg was also accompanied with the highest standard deviation in the study.

There was an improvement in the in vivo performance of the compositions of the present invention with of nilotinib stable, amorphous hybrid nanoparticles, that are based on improving absorption and bioavailability by optimization of the solid state properties of the dosage form. The results of the in vivo study in dogs may predict similar absorption properties of stable, amorphous hybrid nanoparticles of the invention, in patients, as there appears to be a close correlation in dog-human gastrointestinal drug absorption processes (Persson, E. M. et al. Pharm. Res. 2005, 22, 2141-2151). The stable, amorphous hybrid nanoparticles of the invention, with advantageous absorption properties, also predict that the oral doses used in clinical practice today may be lowered. Furthermore, the stable, amorphous hybrid nanoparticles of the invention may cause less pH-dependency in the absorption and bioavailability of PKIs.

Example 15

Measurement of Degree/Level of Stability of Compositions with Hybrid Nanoparticles of the Invention In stability tests of compositions comprising hybrid nanoparticles of the invention, it was shown that particles were stable over at least 11 months at room temperature (18-25° C.), as measured by X-Ray powder diffraction and dissolution rate by measurement of AUC.

In series of experiments with stable, amorphous hybrid nanoparticles comprising nilotinib and HPMCP HP55 produced by the methods of the invention, the resulting particles provided stable, amorphous hybrid nanoparticles at 40% drug load (I/P nilotinib base/HPMCP HP55: exp 146), as measured by XRPD as well as dissolution rate by measurement of AUC. The material showed one glass transition temperature at ca 127° C., which indicate a single amorphous phase with inherent stability. Partially crystalline batches also processed similar inherent stability. 6 months storage at room temperature (18-25° C.) of partly crystalline hybrid nanoparticles at 40% drug load, I/P nilotinib base/HPMCP HP55, did not show any signs of physical instability.

Thermalgravimetric analysis provided a mass loss of 1.7% from ambient temperature to 120° C.

Dynamic vapor absorption analysis at 25° C. gave a relative mass increase of ca 7% from 0 to 90% RH (Three cycles from 0 to 90% RH, did not induce a phase change).

The high glass transition temperature, 1.7% mass loss from ambient temperature to 120° C. and moderate hygrospopicity propose an inherent stability. This is supported by stability testing of several batches at various conditions. The longest stability point is 12 months at room temperature (18-25° C.). No batches or conditions have shown any signs of physical instability (FIG. 27).

Modulated Differential Scanning Calorimetry (mDSC)

Modulated Differential Scanning calorimetry (mDSC) analysis was run on a TA Instruments Model Q200 (New Castle, USA), equipped with a RC90 refrigerated cooling system (Home Automation, New Orleans, USA). Samples were weighed to 7±2 mg in Tzero Low-mass aluminum pans and sealed with Tzero lids. They were then heated at a heating rate of 3° C./min from 0 to 170° C. with conventional modulation temperature amplitude of 1° C. and a modulation period of 40 seconds. Ultra-high purity nitrogen was used as purge gas at a flow rate of 50 mL/min. All data analyses were performed using TA Universal Analysis software, version 4.7A. Cell constant and temperature calibrations were conducted with the use of an indium standard prior to instrument operation. DSC results were evaluated in terms of both forward and reverse components of heat flow.

Thermogravimetry (TG) was performed on a Seiko TG/DTA 6200 and open 90 µl Pt-pans with ca 10 to 20 mg of sample and a nitrogen flow of 200 mL/min. The temperature program was ambient (20° C.) to 400° C. with a heating rate of 10° C./min. A blank was subtracted and the TG data was normalized with respect to sample size and analyzed using the Muse Standard Analysis software, version 6.1 U.

Dynamic Vapour Sorption (DVS)

The hygroscopicity of the samples was studied by Dynamic Vapor Sorption Gravimetry (DVS), using a DVS-1 (Surface Measurement Ltd., UK). Approximately 10 mg of the substance was weighed into a glass cup. The relative weight was recorded at 20 second interval when the target relative humidity (RH) over the sample was increased stepwise from 0% to 90%, and then similarly decreased back to 0% RH, with 10% RH per step. Each sample was run in three consecutive full cycles. The condition to proceed to the next level of RH was a weight change below or equal to 0.002% within 15 minutes, with a maximum total time per step of 24 hours. Due to slow equilibration in experiments of this type, the numbers obtained should be regarded as lower estimates of water uptake. The temperature was kept at 25° C.

X-Ray Powder Diffraction (XRPD)

XRD experiments were run on an X'Pert Pro diffractometer (PANanalytical, Almelo, Netherlands) set in Bragg-Brentano geometry. The diffractometer was equipped with 20 µm nickel filter and an X'Celerator RTMS detector with an active length of 2.122° 2θ. A representative sample was placed on a zero background quarts single crystal specimen support (Siltronix, Archamps, France). Experiments were run using Cu $K_\alpha$ radiation (45 kV and 40 mA) at ambient temperature and humidity. Scans were run in continuous mode in the range 4.5-40° 2θ using automatic divergence and anti-scatter slits with observed length of 10 mm, a common counting time of 299.72 seconds, and step size of 0.0167° 2θ. Data collection was done using the application software X'Pert Data Collector V.2.2j and instrument control software V.2.1E, while pattern analysis was done using X'Pert Data Viewer V.1.2c (all software being from PANanalytical, Almelo, Netherlands).

Dissolution Rate by Measurement of AUC

The stable hybrid nanoparticles described in Exp 171 & Exp172 (I/P) as set out below, were produced according to Exp 148, with nilotinib base, HPMCP HP55 and stored at room temperature for 11 months. The non-sink dissolution rate was tested at different time points and the results are presented in Table 47 and FIG. 26. Polyvinyl caprolactam-polyvinyl acetate-polyethylene glycol copolymer was added to enhance solubility. A comparison of the AUC over 80 minutes show clearly that the dissolution rate profile of the particles is practically unchanged after 11 months storage, e.g. the ratio between the AUC of particles produced and tested, compared to particles produced, tested and stored for 11 months is over 97%.

propyl methylcellulose phthalate, polyvinylpyrrolidone, polyvinyl acetate phthalate, copolyvidone, crospovidone, methacrylic acid and ethylacrylate copolymer, methacrylate acid and methyl methacrylate copolymer, polyethylene glycol, DL lactide/glycolide copolymer, poly DL-lactide, cellulose acetate phthalate, carbomer homopolymer Type A, carbomer homopolymer Type B, aminoalkyl methacrylate copolymers, and poloxamers.

TABLE 47

|  | 0 | 1 min | 5 min | 10 min | 20 min | 40 min | 80 min | AUC | Ratio (%) |
|---|---|---|---|---|---|---|---|---|---|
| Exp 171 (t = 0, n = 1) | 0 | 70.5 | 144.8 | 172.8 | 155.8 | 67.7 | 46.0 | 7411.9 |  |
| Exp 171 (t = 11 months, n = 3) | 0 | 20.2 | 110.7 | 149.5 | 158.5 | 83.6 | 34.0 | 7234.5 | 97.6 |
| Standard deviation | 0 | 5.8 | 14.3 | 19.6 | 19.6 | 3.5 | 1.5 |  |  |

The invention claimed is:
1. A pharmaceutical composition, comprising:
(a) amorphous solid dispersion particles having a degree of amorphicity of 100% wherein the particles consist of
(i) a protein kinase inhibitor in an amount of from about 10% by weight to about 70% by weight of the particles; and
(ii) at least one polymeric stabilizing and matrix-forming component;
wherein the amorphous solid dispersion particles are obtained by mixing i) a pressurized solution comprised of the protein kinase inhibitor and a solvent and ii) a pressurized antisolvent;
and
(b) optionally at least one pharmaceutically acceptable solubilizer selected from the group consisting of a d-α-tocopherol acid polyethylene glycol 1000 succinate, a PEG-40 hydrogenated castor oil, a PEG-35 castor oil, a PEG-40 stearate, a hard fat, a polyoxylglyceride, a PEG-8 caprylic/capric glyceride, and a poloxamer;
wherein the protein kinase inhibitor is dasatinib, dasatinib hydrate, dasatinib solvate, or combinations thereof; and
wherein the at least one pharmaceutically acceptable solubilizer, when present, is a physical mixture with the amorphous solid dispersion particles.

2. The composition of claim 1, wherein the amount of the protein kinase inhibitor is from about 10% by weight to about 50% by weight of the particles.

3. The composition of claim 1, wherein the amount of the protein kinase inhibitor is from about 10% by weight to about 40% by weight of the particles.

4. The composition of claim 1, wherein the amount of the protein kinase inhibitor is from about 10% by weight to about 30% by weight of the particles.

5. The composition of claim 1, wherein the protein kinase inhibitor is dasatinib.

6. The composition of claim 1, wherein the protein kinase inhibitor is dasatinib hydrate.

7. The composition of claim 1, wherein the protein kinase inhibitor is dasatinib solvate.

8. The composition of claim 1, wherein the at least one polymeric stabilizing and matrix-forming component is selected from methyl cellulose, hydroxyethyl cellulose, hydroxypropyl cellulose, hydroxypropyl methylcellulose, hydroxypropyl methylcellulose acetate succinate, hydroxypropyl methylcellulose phthalate, polyvinylpyrrolidone, polyvinyl acetate phthalate, copolyvidone, crospovidone, methacrylic acid and ethylacrylate copolymer, methacrylate acid and methyl methacrylate copolymer, polyethylene glycol, DL lactide/glycolide copolymer, poly DL-lactide, cellulose acetate phthalate, carbomer homopolymer Type A, carbomer homopolymer Type B, aminoalkyl methacrylate copolymers, and poloxamers.

9. The composition of claim 1, wherein the at least one polymeric stabilizing and matrix-forming component is selected from the group consisting of hydroxypropyl methylcellulose phthalate, hydroxypropyl cellulose, copolyvidone, hydroxypropyl methylcellulose acetate succinate, polyvinyl acetate phthalate, cellulose acetate phthalate and polyvinylpyrrolidone.

10. The composition of claim 1, wherein the composition further comprises the at least one pharmaceutically acceptable solubilizer.

11. The composition of claim 10, wherein the solubilizer is selected from the group consisting of d-α-tocopherol acid polyethylene glycol 1000 succinate and a hydrogenated castor oil.

12. The composition of claim 10, wherein the solubilizer is distributed to the surface of the particles.

13. The composition of claim 1, wherein the particles have an average particle diameter size of less than: (i) about 1000 nm, (ii) about 500 nm, or (iii) about 250 nm.

14. The pharmaceutical composition of claim 1, wherein the pressurized antisolvent comprises carbon dioxide.

15. A pharmaceutical composition, consisting of:
(a) amorphous solid dispersion particles having a degree of amorphicity of 100%, wherein the particles consist of consisting of
i) dasatinib in an amount of from about 10% by weight to about 70% by weight of the particles; and
ii) copolyvidone;
wherein the amorphous solid dispersion particles are obtained by mixing i) a pressurized solution comprised of dasatinib and a solvent and ii) a pressurized anti solvent;
and
(b) an excipient.

16. The pharmaceutical composition of claim 15, wherein the amount of dasatinib, based on the total weight of particles, is from (i) about 10% by weight to about 40% by weight.

17. The pharmaceutical composition of claim 15, wherein the particles have an average particle size of less than: (i) about 1000 nm, (ii) about 500 nm, or (iii) about 250 nm.

18. The pharmaceutical composition of claim 15, wherein the pressurized antisolvent comprises carbon dioxide.

19. The pharmaceutical composition of claim 15, wherein the amount of dasatinib, based on the total weight of particles, is from about 10% by weight to about 30% by weight.

20. A method of treating a proliferative disorder in a patient in need thereof, comprising administering a therapeutically effective amount of the pharmaceutical composition of claim 1.

21. The method of claim 20, wherein the proliferative disorder is selected from tumours and cancers.

22. The method of claim 20, wherein the proliferative disorder is selected from neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer , ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

23. A method of treating proliferative disorder in a patient in need thereof, comprising administering a therapeutically effective amount of the pharmaceutical composition of claim 15.

* * * * *

UNITED STATES PATENT AND TRADEMARK OFFICE
CERTIFICATE OF CORRECTION

PATENT NO. : 9,827,230 B2
APPLICATION NO. : 15/248107
DATED : November 28, 2017
INVENTOR(S) : Magnus Brisander et al.

Page 1 of 1

It is certified that error appears in the above-identified patent and that said Letters Patent is hereby corrected as shown below:

In the Claims

Column 80, Lines 44-45, Claim 15: "consist of consisting of" should read --consist of--

Column 80, Line 52, Claim 15: "anti solvent" should read --antisolvent;--

Signed and Sealed this
Ninth Day of January, 2018

Joseph Matal
*Performing the Functions and Duties of the*
*Under Secretary of Commerce for Intellectual Property and*
*Director of the United States Patent and Trademark Office*